US010292625B2

(12) United States Patent
Shinar et al.

(10) Patent No.: US 10,292,625 B2
(45) Date of Patent: May 21, 2019

(54) MONITORING A SLEEPING SUBJECT

(71) Applicant: EARLYSENSE LTD., Ramat Gan (IL)

(72) Inventors: Zvika Shinar, Binyamina (IL); Maayan Davidovich, Haifa (IL); Tal Klap, Ramat Gan (IL); Smadar Hoffert, Givat Shmuel (IL); Guy Meger, Haifa (IL)

(73) Assignee: EARLYSENSE LTD., Ramat Gan (IL)

(*) Notice: Subject to any disclaimer, the term of this patent is extended or adjusted under 35 U.S.C. 154(b) by 811 days.

(21) Appl. No.: 14/474,357

(22) Filed: Sep. 2, 2014

(65) Prior Publication Data
US 2014/0371635 A1   Dec. 18, 2014

Related U.S. Application Data

(63) Continuation-in-part of application No. PCT/IL2014/050644, filed on Jul. 17, 2014, which is
(Continued)

(51) Int. Cl.
*A61B 5/00* (2006.01)
*A61B 5/11* (2006.01)
(Continued)

(52) U.S. Cl.
CPC .......... *A61B 5/1102* (2013.01); *A61B 5/002* (2013.01); *A61B 5/02055* (2013.01); *A61B 5/11* (2013.01);
(Continued)

(58) Field of Classification Search
USPC ........................................................ 600/595
See application file for complete search history.

(56) References Cited

U.S. PATENT DOCUMENTS 3,890,958 A   6/1975   Fister
4,033,332 A   7/1977   Hardway, Jr.
(Continued)

FOREIGN PATENT DOCUMENTS

EP   0853918   7/1998
EP   0860803   8/1998
(Continued)

OTHER PUBLICATIONS

English translation of notice of reasons for rejection of Japanese application No. 2013-542667 dated Jul. 14, 2015.
(Continued)

*Primary Examiner* — Sean P Dougherty
(74) *Attorney, Agent, or Firm* — Roach Brown McCarthy & Gruber, P.C.; Kevin D. McCarthy

(57) ABSTRACT

Apparatus and methods are described, including apparatus for use with a subject who shares a bed with a second person. A motion sensor detects motion of the subject and motion of the second person, and generates a motion signal in response thereto. A control unit identifies components of the motion signal that were generated in response to motion of the subject, by distinguishing between components of the motion signal that were generated in response to motion of the subject, and components of the motion signal that were generated in response to motion of the second person. The control unit analyzes the components of the motion signal that were generated in response to motion of the subject and generates an output in response thereto. Other applications are also described.

28 Claims, 33 Drawing Sheets

Related U.S. Application Data a continuation-in-part of application No. 13/906,325, filed on May 30, 2013, now Pat. No. 8,882,684, which is a continuation-in-part of application No. PCT/IL2013/050283, filed on Mar. 24, 2013, which is a continuation-in-part of application No. 13/389,200, filed as application No. PCT/IL2011/050045 on Dec. 7, 2011, now abandoned.

(60) Provisional application No. 61/926,499, filed on Jan. 13, 2014, provisional application No. 61/847,579, filed on Jul. 18, 2013, provisional application No. 61/772,553, filed on Mar. 5, 2013, provisional application No. 61/764,541, filed on Feb. 14, 2013, provisional application No. 61/757,739, filed on Jan. 29, 2013, provisional application No. 61/756,003, filed on Jan. 24, 2013, provisional application No. 61/748,081, filed on Jan. 1, 2013, provisional application No. 61/739,033, filed on Dec. 19, 2012, provisional application No. 61/725,513, filed on Nov. 13, 2012, provisional application No. 61/722,810, filed on Nov. 6, 2012, provisional application No. 61/698,736, filed on Sep. 10, 2012, provisional application No. 61/696,326, filed on Sep. 4, 2012, provisional application No. 61/618,792, filed on Apr. 1, 2012, provisional application No. 61/561,962, filed on Nov. 21, 2011, provisional application No. 61/439,971, filed on Feb. 7, 2011, provisional application No. 61/420,402, filed on Dec. 7, 2010.

(51) Int. Cl.
*G08B 21/02* (2006.01)
*G08B 21/04* (2006.01)
*G08B 25/00* (2006.01)
*A61B 5/0205* (2006.01)

(52) U.S. Cl.
CPC .......... *A61B 5/4815* (2013.01); *A61B 5/6891* (2013.01); *A61B 5/6892* (2013.01); *A61B 5/746* (2013.01); *G08B 21/0211* (2013.01); *G08B 21/0461* (2013.01); *G08B 25/006* (2013.01); *A61B 5/1115* (2013.01); *A61B 5/4809* (2013.01); *A61G 2203/36* (2013.01)

(56) References Cited

U.S. PATENT DOCUMENTS

| | | | |
|---|---|---|---|
| 4,122,838 A | 10/1978 | Leonard | |
| 4,301,879 A | 11/1981 | Dubow | |
| 4,338,950 A | 7/1982 | Barlow, Jr. | |
| 4,494,553 A | 1/1985 | Sciarra | |
| 4,657,025 A | 4/1987 | Orlando | |
| 4,657,026 A | 4/1987 | Tagg | |
| 4,686,999 A | 8/1987 | Snyder | |
| 4,738,264 A | 4/1988 | Orlando | |
| 4,757,825 A | 7/1988 | Diamond | |
| 4,817,610 A | 4/1989 | Lee | |
| 4,832,038 A | 5/1989 | Arai | |
| 4,926,866 A | 5/1990 | Lee | |
| 5,002,060 A | 3/1991 | Nedivi | |
| 5,010,772 A | 4/1991 | Bourland | |
| 5,025,791 A | 6/1991 | Niwa | |
| 5,076,281 A | 12/1991 | Gavish | |
| 5,107,845 A | 4/1992 | Guern | |
| 5,111,826 A | 5/1992 | Nasiff | |
| 5,137,033 A | 8/1992 | Norton | |
| 5,235,989 A | 8/1993 | Zomer | |
| 5,253,656 A | 10/1993 | Rincoe | |
| 5,276,432 A | 1/1994 | Travis | |
| 5,309,921 A | 5/1994 | Kisner | |
| 5,309,922 A | 5/1994 | Schechter | |
| 5,319,363 A | 6/1994 | Welch | |
| 5,368,026 A | 11/1994 | Swedlow | |
| 5,393,935 A | 2/1995 | Hasty | |
| 5,448,996 A | 9/1995 | Bellin | |
| 5,479,939 A | 1/1996 | Ogino | |
| 5,515,865 A | 5/1996 | Scanlon | |
| 5,520,176 A | 5/1996 | Cohen | |
| 5,522,382 A | 6/1996 | Sullivan | |
| 5,540,734 A | 7/1996 | Zabara | |
| 5,590,650 A | 1/1997 | Genova | |
| 5,620,003 A | 4/1997 | Sepponen | |
| 5,662,106 A | 9/1997 | Swedlow | |
| 5,684,460 A | 11/1997 | Scanlon | |
| 5,687,734 A | 11/1997 | Dempsey | |
| 5,699,038 A | 12/1997 | Ulrich | |
| 5,730,140 A | 3/1998 | Fitch | |
| 5,738,102 A | 4/1998 | Lemelson | |
| 5,743,263 A | 4/1998 | Baker, Jr. | |
| 5,797,852 A | 8/1998 | Karakasoglu | |
| 5,800,337 A | 9/1998 | Gavish | |
| 5,800,360 A | 9/1998 | Kisner | |
| 5,853,005 A | 12/1998 | Scanlon | |
| 5,879,313 A | 3/1999 | Raviv | |
| 5,902,250 A | 5/1999 | Verrier | |
| 5,944,680 A | 8/1999 | Christopherson | |
| 5,957,861 A | 9/1999 | Combs | |
| 5,964,720 A | 10/1999 | Pelz | |
| 5,989,193 A | 11/1999 | Sullivan | |
| 6,014,346 A | 1/2000 | Malone | |
| 6,015,388 A | 1/2000 | Sackner | |
| 6,033,370 A | 3/2000 | Reinbold | |
| 6,036,660 A | 3/2000 | Toms | |
| 6,047,203 A | 4/2000 | Sackner | |
| 6,062,216 A | 5/2000 | Corn | |
| 6,064,910 A | 5/2000 | Andersson | |
| 6,080,106 A | 6/2000 | Lloyd | |
| 6,090,037 A | 7/2000 | Gavish | |
| 6,093,146 A | 7/2000 | Filangeri | |
| 6,104,949 A | 8/2000 | Pitts Crick | |
| 6,126,595 A | 10/2000 | Amano | |
| 6,134,970 A | 10/2000 | Kumakawa | |
| 6,135,970 A | 10/2000 | Kadhiresan | |
| 6,157,850 A | 12/2000 | Diab | |
| 6,166,644 A * | 12/2000 | Stroda ............... A61B 5/1113 340/521 |
| 6,168,568 B1 | 1/2001 | Gavriely | |
| 6,198,394 B1 | 3/2001 | Jacobsen | |
| 6,223,064 B1 | 4/2001 | Lynn | |
| 6,239,706 B1 | 5/2001 | Yoshiike | |
| 6,259,355 B1 | 7/2001 | Chaco | |
| 6,261,238 B1 | 7/2001 | Gavriely | |
| 6,290,654 B1 | 9/2001 | Karakasoglu | |
| 6,325,761 B1 | 12/2001 | Jay | |
| 6,352,517 B1 | 3/2002 | Flock | |
| 6,368,287 B1 | 4/2002 | Hadas | |
| 6,375,621 B1 | 4/2002 | Sullivan | |
| 6,375,623 B1 | 4/2002 | Gavriely | |
| 6,383,142 B1 | 5/2002 | Gavriely | |
| 6,402,691 B1 | 6/2002 | Peddicord | |
| 6,409,661 B1 | 6/2002 | Murphy | |
| 6,436,057 B1 | 8/2002 | Goldsmith | |
| 6,450,957 B1 | 9/2002 | Yoshimi | |
| 6,454,719 B1 | 9/2002 | Greenhut | |
| 6,468,234 B1 | 10/2002 | Van der Loos | |
| 6,485,441 B2 | 11/2002 | Woodward | |
| 6,498,652 B1 | 12/2002 | Varshneya | |
| 6,512,949 B1 | 1/2003 | Combs | |
| 6,517,497 B2 | 2/2003 | Rymut | |
| 6,527,729 B1 | 3/2003 | Turcott | |
| 6,544,173 B2 | 4/2003 | West | |
| 6,544,174 B2 | 4/2003 | West | |
| 6,547,743 B2 | 4/2003 | Brydon | |
| 6,551,252 B2 | 4/2003 | Sackner | |
| 6,561,978 B1 | 5/2003 | Conn | |
| 6,579,232 B2 | 6/2003 | Sakamaki | |
| 6,585,645 B2 | 7/2003 | Hutchinson | |
| 6,589,188 B1 | 7/2003 | Street | |
| 6,599,251 B2 | 7/2003 | Chen | |

(56) References Cited

U.S. PATENT DOCUMENTS

| | | |
|---|---|---|
| 6,600,949 B1 | 7/2003 | Turcott |
| 6,616,606 B1 | 9/2003 | Petersen |
| 6,630,568 B1 | 10/2003 | Johnson |
| 6,631,281 B1 | 10/2003 | Kastle |
| 6,641,542 B2 | 11/2003 | Cho |
| 6,646,556 B1 | 11/2003 | Smith |
| 6,662,032 B1 | 12/2003 | Gavish |
| 6,666,830 B1 | 12/2003 | Lehrman |
| 6,719,708 B1 | 4/2004 | Jansen |
| 6,725,074 B1 | 4/2004 | Kastle |
| 6,731,311 B2 | 5/2004 | Bufe |
| 6,745,060 B2 | 6/2004 | Diab |
| 6,751,498 B1 | 6/2004 | Greenberg |
| 6,752,766 B2 | 6/2004 | Kowallik |
| 6,754,516 B2 | 6/2004 | Mannheimer |
| 6,790,183 B2 | 9/2004 | Murphy |
| 6,792,819 B2 | 9/2004 | Gladney |
| 6,821,258 B2 | 11/2004 | Reed |
| 6,822,564 B2 | 11/2004 | Al-Ali |
| 6,827,670 B1 | 12/2004 | Stark |
| 6,830,548 B2 | 12/2004 | Bonnet |
| 6,840,907 B1 | 1/2005 | Brydon |
| 6,856,141 B2 | 2/2005 | Ariav |
| 6,878,121 B2 | 4/2005 | Krausman |
| 6,893,404 B2 | 5/2005 | Ragnarsdottir |
| 6,955,647 B2 | 10/2005 | Rice |
| 6,980,679 B2 | 12/2005 | Jeung |
| 6,984,207 B1 | 1/2006 | Sullivan |
| 6,984,993 B2 | 1/2006 | Ariav |
| 6,988,989 B2 | 1/2006 | Weiner |
| 7,022,072 B2 | 4/2006 | Fox |
| 7,025,729 B2 | 4/2006 | de Chazal |
| 7,077,810 B2 | 7/2006 | Lange |
| 7,079,035 B2 | 7/2006 | Bock |
| 7,283,161 B2 | 10/2007 | Someya |
| 7,294,112 B1 | 11/2007 | Dunlop |
| 7,304,580 B2 | 12/2007 | Sullivan |
| 7,314,451 B2 | 1/2008 | Halperin |
| 7,390,299 B2 | 6/2008 | Weiner |
| 7,396,331 B2 | 7/2008 | Mack |
| 7,396,333 B2 | 7/2008 | Stahmann |
| 7,415,297 B2 | 8/2008 | Al-Ali |
| 7,428,468 B2 | 9/2008 | Takemura |
| 7,431,700 B2 | 10/2008 | Aoki |
| 7,433,827 B2 | 10/2008 | Rosenfeld |
| 7,439,856 B2 | 10/2008 | Weiner |
| 7,454,359 B2 | 11/2008 | Rosenfeld |
| 7,508,307 B2 | 3/2009 | Albert |
| 7,572,225 B2 | 8/2009 | Stahmann |
| 7,610,094 B2 | 10/2009 | Stahmann |
| 7,629,890 B2 | 12/2009 | Sullivan |
| 7,666,151 B2 | 2/2010 | Sullivan |
| 7,689,440 B2 | 3/2010 | Brown |
| 7,704,215 B2 | 4/2010 | Lewicke |
| 7,778,851 B2 | 8/2010 | Schoenberg |
| 7,860,583 B2 | 12/2010 | Condurso |
| 7,862,523 B2* | 1/2011 | Ruotoistenmaki ... A61B 5/1102 600/484 |
| 7,880,606 B2 | 2/2011 | Al-Ali |
| 7,896,813 B2 | 3/2011 | Sowelam |
| 7,938,782 B2 | 5/2011 | Stahmann |
| 7,952,475 B2 | 5/2011 | Ivanov |
| 7,959,574 B2 | 6/2011 | Bardy |
| 8,376,954 B2 | 2/2013 | Lange |
| 8,403,865 B2 | 3/2013 | Halperin |
| 8,491,492 B2 | 7/2013 | Shinar |
| 8,517,953 B2 | 8/2013 | Lange |
| 8,585,607 B2 | 11/2013 | Klap |
| 8,603,010 B2 | 12/2013 | Lange |
| 8,679,030 B2 | 3/2014 | Shinar |
| 8,679,034 B2 | 3/2014 | Halperin |
| 8,731,646 B2 | 5/2014 | Halperin |
| 8,734,360 B2 | 5/2014 | Klap |
| 2001/0005773 A1 | 6/2001 | Larsen |
| 2002/0058155 A1 | 5/2002 | Guofang |
| 2002/0077554 A1 | 6/2002 | Schwartz |
| 2002/0082486 A1 | 6/2002 | Lavery |
| 2002/0086870 A1 | 7/2002 | Radulovacki |
| 2002/0097155 A1 | 7/2002 | Cassel |
| 2002/0099303 A1 | 7/2002 | Bardy |
| 2002/0106709 A1 | 8/2002 | Potts |
| 2002/0150957 A1 | 10/2002 | Slotman |
| 2002/0196148 A1 | 12/2002 | Nunome |
| 2003/0004403 A1 | 1/2003 | Drinan |
| 2003/0004423 A1 | 1/2003 | Lavie |
| 2003/0018276 A1 | 1/2003 | Mansy |
| 2003/0045806 A1 | 3/2003 | Brydon |
| 2003/0100839 A1 | 5/2003 | Cohen |
| 2003/0100930 A1 | 5/2003 | Cohen |
| 2003/0125612 A1 | 7/2003 | Fox |
| 2003/0135127 A1 | 7/2003 | Sackner |
| 2003/0139678 A1 | 7/2003 | Hoium |
| 2003/0144829 A1 | 7/2003 | Geatz |
| 2003/0153831 A1 | 8/2003 | Zumeris |
| 2003/0199945 A1 | 10/2003 | Ciulla |
| 2004/0010202 A1 | 1/2004 | Nakatani |
| 2004/0046668 A1 | 3/2004 | Smith |
| 2004/0073098 A1 | 4/2004 | Geva |
| 2004/0082874 A1 | 4/2004 | Aoki |
| 2004/0111040 A1 | 6/2004 | Ni |
| 2004/0111045 A1 | 6/2004 | Sullivan |
| 2004/0116784 A1 | 6/2004 | Gavish |
| 2004/0133079 A1 | 7/2004 | Mazar |
| 2004/0152999 A1 | 8/2004 | Cohen |
| 2004/0166541 A1 | 8/2004 | Guo |
| 2004/0210155 A1 | 10/2004 | Takemura |
| 2004/0225226 A1 | 11/2004 | Lehrman |
| 2004/0230105 A1 | 11/2004 | Geva |
| 2005/0027216 A1 | 2/2005 | Guillemaud |
| 2005/0043644 A1 | 2/2005 | Stahmann |
| 2005/0049648 A1 | 3/2005 | Cohen |
| 2005/0061315 A1 | 3/2005 | Lee |
| 2005/0074361 A1 | 4/2005 | Tanoshima |
| 2005/0080349 A1 | 4/2005 | Okada |
| 2005/0085734 A1 | 4/2005 | Tehrani |
| 2005/0085866 A1 | 4/2005 | Tehrani |
| 2005/0096557 A1 | 5/2005 | Vosburgh |
| 2005/0102165 A1 | 5/2005 | Oshita |
| 2005/0119586 A1 | 6/2005 | Coyle |
| 2005/0124864 A1* | 6/2005 | Mack ................. A61B 5/024 600/300 |
| 2005/0165284 A1 | 7/2005 | Gefen |
| 2005/0168341 A1 | 8/2005 | Reeder |
| 2005/0192508 A1 | 9/2005 | Lange |
| 2005/0201970 A1 | 9/2005 | Hu |
| 2005/0240091 A1 | 10/2005 | Lynn |
| 2006/0020295 A1 | 1/2006 | Brockway |
| 2006/0028350 A1 | 2/2006 | Bhai |
| 2006/0063982 A1 | 3/2006 | Sullivan |
| 2006/0084848 A1 | 4/2006 | Mitchnick |
| 2006/0089856 A1 | 4/2006 | Kadhiresan |
| 2006/0129047 A1 | 6/2006 | Ruotoistenmaki |
| 2006/0152378 A1 | 7/2006 | Lokhorst |
| 2006/0155167 A1 | 7/2006 | Elliott |
| 2006/0181424 A1 | 8/2006 | Graves |
| 2006/0195025 A1 | 8/2006 | Ali |
| 2006/0220885 A1 | 10/2006 | Bock |
| 2006/0258952 A1 | 11/2006 | Stahmann |
| 2007/0024451 A1 | 2/2007 | Albert |
| 2007/0032733 A1 | 2/2007 | Burton |
| 2007/0118054 A1 | 5/2007 | Pinhas |
| 2007/0139678 A1 | 6/2007 | Horita |
| 2007/0156031 A1 | 7/2007 | Sullivan |
| 2007/0177785 A1 | 8/2007 | Raffy |
| 2007/0249952 A1 | 10/2007 | Rubin |
| 2007/0257564 A1 | 11/2007 | Kitade |
| 2007/0276202 A1 | 11/2007 | Raisanen |
| 2008/0004904 A1 | 1/2008 | Tran |
| 2008/0005838 A1 | 1/2008 | Wan Fong |
| 2008/0033304 A1 | 2/2008 | Dalal |
| 2008/0042835 A1 | 2/2008 | Russell |
| 2008/0114260 A1 | 5/2008 | Lange |
| 2008/0275349 A1 | 11/2008 | Halperin |

(56) References Cited

U.S. PATENT DOCUMENTS

| | | | |
|---|---|---|---|
| 2009/0099480 A1* | 4/2009 | Salgo | A61B 5/103 600/595 |
| 2009/0164239 A1 | 6/2009 | Hayter | |
| 2009/0299229 A1 | 12/2009 | Johnson | |
| 2010/0094108 A1 | 4/2010 | Rojas Ojeda | |
| 2010/0215074 A1 | 8/2010 | Lozinski | |
| 2010/0217618 A1 | 8/2010 | Piccirillo | |
| 2010/0234705 A1 | 9/2010 | Lynn | |
| 2011/0046498 A1 | 2/2011 | Klap | |
| 2011/0112442 A1 | 5/2011 | Meger | |
| 2011/0282216 A1 | 11/2011 | Shinar | |
| 2012/0132211 A1 | 5/2012 | Halperin | |
| 2012/0253142 A1 | 10/2012 | Meger | |
| 2013/0144178 A1 | 6/2013 | Halperin | |
| 2013/0174345 A1 | 7/2013 | Leu | |
| 2013/0245502 A1 | 9/2013 | Lange | |
| 2013/0267791 A1 | 10/2013 | Halperin | |
| 2013/0281866 A1 | 10/2013 | Shinar | |
| 2014/0005502 A1 | 1/2014 | Klap et al. | |
| 2014/0171816 A1 | 6/2014 | Pinhas | |
| 2014/0207204 A1 | 7/2014 | Halperin | |
| 2015/0164433 A1 | 6/2015 | Halperin | |
| 2015/0164438 A1 | 6/2015 | Halperin | |
| 2015/0190087 A1 | 7/2015 | Shinar | |
| 2016/0058428 A1 | 3/2016 | Shinar | |
| 2016/0058429 A1 | 3/2016 | Shinar | |

FOREIGN PATENT DOCUMENTS

| | | |
|---|---|---|
| EP | 1350466 | 10/2003 |
| GB | 2329966 | 4/1999 |
| JP | 3-258246 | 11/1991 |
| JP | 4-28352 | 1/1992 |
| JP | 5323635 | 12/1993 |
| JP | 08-080285 | 3/1996 |
| JP | 08-225210 | 9/1996 |
| JP | 10-229973 | 9/1998 |
| JP | 2001-037739 | 2/2001 |
| JP | 2001-145605 | 5/2001 |
| JP | 2001-327549 | 11/2001 |
| JP | 2002-224053 | 8/2002 |
| JP | 2002-336207 | 11/2002 |
| JP | 2003-225210 | 8/2003 |
| JP | 2004-049388 | 2/2004 |
| JP | 2004-049389 | 2/2004 |
| JP | 2004-049838 | 2/2004 |
| JP | 2004-154310 | 6/2004 |
| JP | 2005-021450 | 1/2005 |
| JP | 2005-095307 | 4/2005 |
| JP | 2005-143661 | 6/2005 |
| JP | 2005-160876 | 6/2005 |
| JP | 2005-237479 | 9/2005 |
| JP | 2005-279113 | 10/2005 |
| WO | 86/05965 | 10/1986 |
| WO | 96/08197 | 3/1996 |
| WO | 97/40748 | 11/1997 |
| WO | 99/04691 | 2/1999 |
| WO | 99/32537 | 7/1999 |
| WO | 01/73718 | 10/2001 |
| WO | 01/80727 | 11/2001 |
| WO | 03/013355 | 2/2003 |
| WO | 03/057025 | 7/2003 |
| WO | 2004/006768 | 1/2004 |
| WO | 2004/091378 | 10/2004 |
| WO | 2004/114193 | 12/2004 |
| WO | 2005/028029 | 3/2005 |
| WO | 2005/037077 | 4/2005 |
| WO | 2005/037366 | 4/2005 |
| WO | 2005/055824 | 6/2005 |
| WO | 2005/074361 | 8/2005 |
| WO | 2006/008743 | 1/2006 |
| WO | 2006/054306 | 5/2006 |
| WO | 2006/082589 | 8/2006 |
| WO | 2006/137067 | 12/2006 |
| WO | 2007/052108 | 5/2007 |
| WO | 2007/081629 | 7/2007 |
| WO | 2008/135985 | 11/2008 |
| WO | 2009/076298 | 6/2009 |
| WO | 2009/138976 | 11/2009 |
| WO | 2010/080794 A2 | 7/2010 |
| WO | 2010/133996 A1 | 11/2010 |
| WO | 2012/077113 | 6/2012 |
| WO | 2013/150523 | 10/2013 |

OTHER PUBLICATIONS

"Breathing easier with astma", pp. 1-46, http://www.ihc.com/xp/ihc/documents/clinical/101/3/1/asthma_breathe.;pdf. (2004).

"British guidelines on management of asthma: a national clinical guidline", British Thoracic Society, Scottish Intercollegiate Guidelines Network, Revised edition, Apr. 2004, pp. 1-92.

"Does my child have asthma?" Solano Asthma Coalition, American Lung Association of the East Bay (http://www.alaebay.org/misc_pdf/solano_asthnna_coalition_child_asthma.pdf) (2001).

"InTouch Critical Care Bed", Jan. 1, 2008(Jan. 1, 2008), XP055109799, Retrieved from the Internet: URL:http://www.stryker.com/intouch/intouchspec.pdf (retrieved on Mar. 25, 2014).

"Managing asthma", http://kidshealth.org/pageManager.jsp?dn=KidsHealth&lic=1&ps=107&cat_id=143&article_set=2 (2011).

"Medical Mutual clinical practice guidelines for asthma: 2004, "Medical Mutual (Cleveland, OH), (http://www.medmutual.com/provider/pdf/resources/asthma4.pdf).

"Non-invasive fiber-optic sensor technology for monitoring sleep apnea and SIDS", http://www.kidsource.com/products/fiber.optic.SIDS.html (2000).

"Peak flow learning center", http://www.njc.org/disease-info/diseases/asthma/living/tools/peak/index/aspx (2007—according to the publication).

"Signs and symptoms of asthma", http://www.indianchestsociety.org/symptomsofasthma.htm (2007—according to the publication).

Alihanka, J. et al., "A new method for long-term monitoring ballistocardiogram, heart rate, and respiration", AM J Physiol Regul Integ Comp Physiol 1981; 240: 384-92.

Alihanka, J. et al., "A static charge sensitive bed. A new method for recording body movement during sleep", Electroencephalography and Clinical Neurophysiology 1979; 46(6): 731-4.

Ancoli-Israel S. et al., (2003) The role of actigraphy in the study of sleep and circadian rhythms. Sleep. 26(3):342-92.

Baren, Jill M. et al., "Current Concepts in the ED treatment of pediatric Asthma", Respiratory Medicine Consensus Reports (Thomson American Health Consultants, Dec. 28, 2003), pp. 1-12.

Bentur, L. et al., "Wheeze monitoring in children for assessment of nocturnal asthma and response to therapy", Eur respire J 2003; 21: 621-6.

Bilmes et al., (1998) A gentle tutorial of the EM algorithm and its application to parameter estimation for caussian mixture and hidden markov models. Internation Computer Science Institut, pp. 1-13.

Brenner, Barry E. et al., "The clinical presentation of acute ashma in adults and children", In Brenner, BE, ed. Emergency Asthma (New York: Marcel Dekker 1994; pp. 201-32).

Butter CD. et al., (1978) Fiber optics strain gauge. Appl Opt. 17(18): 2867-9.

Chaboyer W et al., (2008) Predictors of adverse events in patients after discharge from the intensive care unit. Am J Crit Care.17:255-63.

Chan et al., Prosafe a multisensory remote monitoring system for the elderly or the handicapped, Independent Living for Persons with Disabilities and Elderly People: ICOST, 2003 1st International Conference on Smart Homes and Health Telematics.

Chang, A.B. et al., "Cough, airway inflammation, and mild asthma exacerbation", Archives of disease in childhood 2002; 86:270-5.

Dekker et al., (2000) Low heart rate variability in a 2-minute rhythm strip predicts risk of coronary heart disease and mortality from several causes: the ARIC study. Circulation 102: 1239-44.

Delmore G. et al., (1977) The role of augmented breaths (sighs) in bronchial asthma attacks. Pflugers Arch. 372(1):1-6.

(56) References Cited

OTHER PUBLICATIONS

Dempster AP. et al., (1977) Maximum likelihood from incomplete data via the EM algorithm. Ournal of the Royal statistical Society 39(1):1-38.
E. Campo, M. Chan, Detecting abnormal behaviour by real-time monitoring of patients, AAAI Technical Report WS-02-02. Compilation copyright © 2002.
Fieselmann JF et al., (1993) Respiratory rate predicts cardiopulmonary arrest for internal medicine inpatients. J Gen Intern Med 8(7):354-60.
Fitzpatrick MF. et al., (1991) Morbidity in nocturnal asthma: sleep quality and daytime cognitive performance. Thorax. 46(8):569-73.
Fitzpatrick, MF. et al.,(1993) "Snoring, asthma and sleep disturbances in Britain: a community based survey", ERS Journal Ltd., pp. 531-535.
Hark et al., (2005) Spontaneous sigh rates during sedentary activity: watching television vs reading. Ann Allergy Asthma Immunol. 94(2):247-50.
Hogan J., (2006) Why don't nurses monitor the respiratory rates of patients? Br J Nurs 15(9):489-92.
Hod et al., (2001) Proposed supplements and amendments to 'A Manual of Standardized Terminology, Techniques and Scoring System for Sleep Stages of Human Subjects', the Rechtschaffen & Kales (1968) standard. Psychiatry Clin Neurosci. 55(3):305-10.
Hsu, J.Y. et al., "Coughing frequency in patients with persistent cough; Assessment using a 24 hour ambulatory recorder", Eur Repir J 1994; 7: 1246-53.
Hudgel et al., (1984) Mechanics of the respiratory system and breathing pattern during sleep in normal humans. J Appl Physiol. 56(1): 133-7.
Jobanputra et al., (1991) Management of acute asthma attacks in general practice. Br J Gen Pract. Oct. 1991;41 (351):410-3.
Kandtelhardt, J.W., T. Penzel, S. Rostig, H. F. Becker, S. Halvin, and A. Bunde, Breathing during REM and non-REM sleep: correlated versus uncorrelated behavior, 25 Physica. A., vol. 319, pp. 447-457, 2003.
Kap-Ho Seo et al., "Bed-type robotic system for the bedridden", advanced Intelligent Mechatronics, Proceedings, 2005 IEE/ASME International Conference on Monterey, CA Jul. 24-28, 2005. Piscataway, NK, USA pp. 1170-1175.
Kapsali et al., (2000) Potent bronchoprotective effect of deep inspiration and its absence in asthma. J Appl Physiol. 89 (2):711-20.
Katz et al., (1986) Detection of preterm labor by ambulatory monitoring of uterine activity: a preliminary report. Obstet Gynecol. 1986; 68(6): 773-8.
Korpas, J. et al., "Analysis of the cough sound: an overview", Pulmonary Pharmacology 1996; 9: 261-8.
Li, Q. and A. Barron, "Mixture density estimation," Advances in neural information processing systems, vol. 12, pp. 279-285, MIT press, 2000.
Lim TO. et al., (1992) Morbidity associated with asthma and audit of asthma treatment in out-patient clinics. Singapore Med J. 33(2):174-6.
Mack, David et al., "Non-invasive analysis of physiological signals: NAPS: A low cost, passive monitoring for sleep quality and related applications", University of Virginia Health System. pp. 1-9 2008.
Madge PJ et al., (1995) Home nebuliser use in children with asthma in two Scottish Health Board Areas. Scott Med J. 40(5):141-3.
Mintzer, Rich, "What the teacher should know about asthma attacks", http://www.familyeducation.com/article/print/0,1303,65-415,00.html?obj_gra (2007—according to the publication).
O'Connor CJ et al, (2007) "Identification of endotracheal tube malpositions using computerized analysis of breath sounds via electronic stethoscopes," Anesth Analg 2005;101:735-9.
Oppenheim, AN., and R.W. Schafer, Discrete-Time Signal Processing, Prentice' Hall, 1989, pp. 311-312.

Pirrila, P. et al., "Objective assessment of cough", Eur respire J 1995; 8: 1949-56.
Plaut, Thomas F., "Tracking and treating asthma in young children", J Respir Dis Pediatrician 2003; 5(2): 67-72.
Pomeranz et al., (1985) Assessment of autonomic function in humans by heart rate spectral analysis. Am J Physiol 248(1 Pt 2): H151-3.
Poteet, Jackie, (2012) "Asthma". http://www.nku.edu/~rad350/asthmajp.html.
Salmi et al., (1986) "Automatic analysis of sleep records with static charge sensitive bed", Electroencephalography and Clinical Neurophysiology, pp. 84-87.
Salmi, Tapani et al., "Long-term recording and automatic analysis of cough using filtered acoustic signals and movements on static charge sensitive bed", Chest 1988; 94: 970-5.
Schwartz, (1978) Estimating the dimension of a model. The Annals of Statistics 6(2):461-4.
Shinar et al., (1998) Identification of arousals using heart rate beat-to-beat variability. Sleep 21(3 Suppl): 294.
Shinar Z. et al., (2001) Automatoc detection of flow-wave-sleep using heart rate variability. Computers in cardiology 28:593-6.
Shochat, Michael et al., "PedemaTOR: Innovative method for detecting pulmonary edema at the pre-clinical stage", http://www.isramed.info/rsnm_rabinovich/pedernator.htm (2005).
Sorvoja, H. and Myllyla, R., "Noninvasive blood pressure measurement methods," Molecular and Quantum Acoustics. vol. 27, 2006. 239-64.
Staderini, Enrico M., (2002) UWB Radars in Medicine, IEEE Aerospace and Electronic Systems Magazine, 17(1):13-18.
Stegmaier-Stracca, Peter A. et al., Cough detection using fuzzy classification, Proceeding of the 1995 ACM Symposium on Applied Computing, Nashville, TN: 440-4.
Tamura T. et al., "A system for monitoring temperature distribution in bed and its application to the assessment of body movement", Physiological Measurement, Institute of Physics Publishing, Bristol, GB 1993; 14(1): 33-41.
Thorpe C.W. et al., (1992) "Towards a quantitative description of asthmatic cough sounds", Eur Respir J 5(6):685-92.
Van Der Loos, H.F. Michiel et al., "Unobstrusive vital signs monitoring from a multisensory bed sheet", RESNA 2001, Reno, NV, Jun. 22-26, 2001, pp. 218-220.
Van Der Loos, H.F.M. et al., "Development of sensate and robotic bed technologies for vital signs monitoring and sleep quality improvement", Abstract, Autonomous Robots, 2003;15(1) http://www.ingenta.com/isi/searching/Expand/ingenta?pub=infobike://klu/auro/2003/00000015/00000001/05126829.
Van Hirtum A. et al., (2002) Autoregressive acoustical modeling of free field cough sound, Proc Int Conference on Acoustics, Speech and Signal Processing, col. 1, pp. 493-496, Orlando, USA.
Waris, M. et al., "A new method for automatic wheeze detection", Technology and Health Care 1998; 6:33-40.
Watanabe et al., (2004) "Noncontact method for sleep stage estimation", IEEE transactions on Biomedical Engineering 10(51):1735-48.
Whitney, C.W., Gottlieb DJ, Redline S, Norman RG, Dodge RR, Shahar E, Surovec S and Nieto FJ, "Reliability of scoring respiratory disturbance indices and sleep staging," Sleep, Nov. 2, 1998; 21(7): 749-757.
Yien HW et al., (1997) Spectral analysis of systemic arterial pressure and heart rate signals as a prognostic tool for the prediction of patient outcome in the intensive care unit. Crit Care Med. 25(2):258-66.
Yongjoon et al., (2005) "Air matters sensor system with balancing tube for unconstrained measurement of respiration and heart beat movements", Physiol Meas, pp. 413-422.

\* cited by examiner

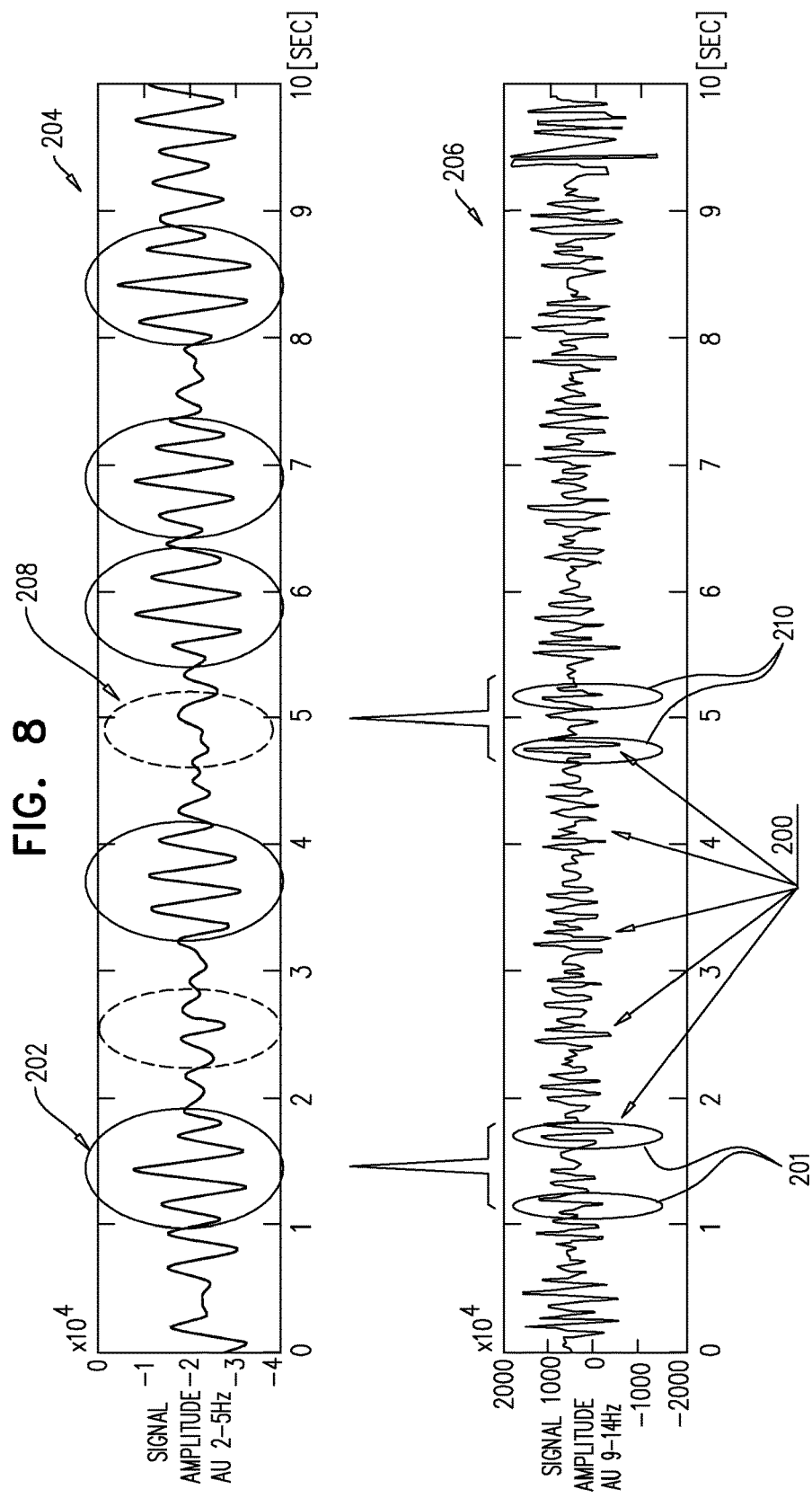

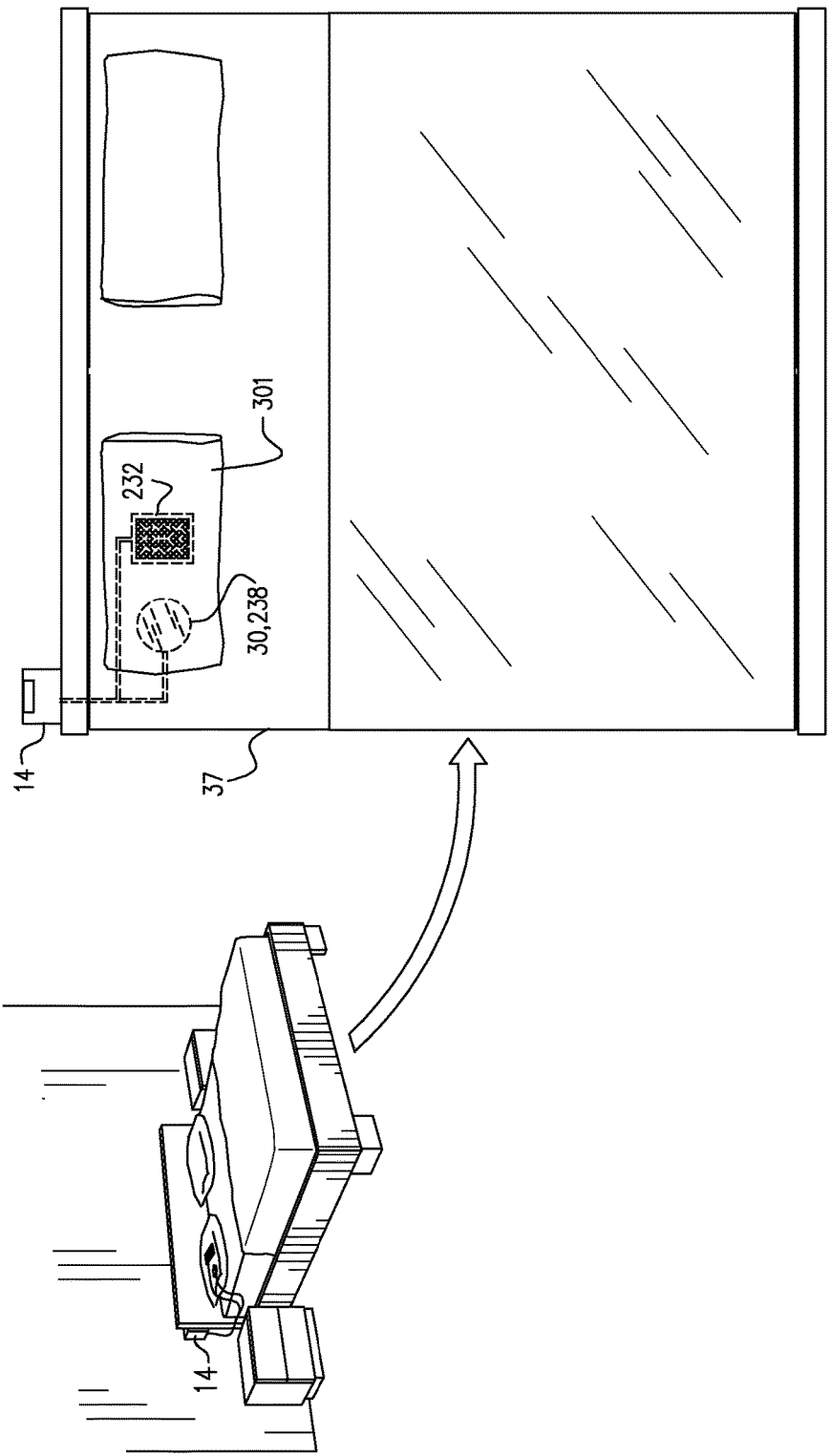

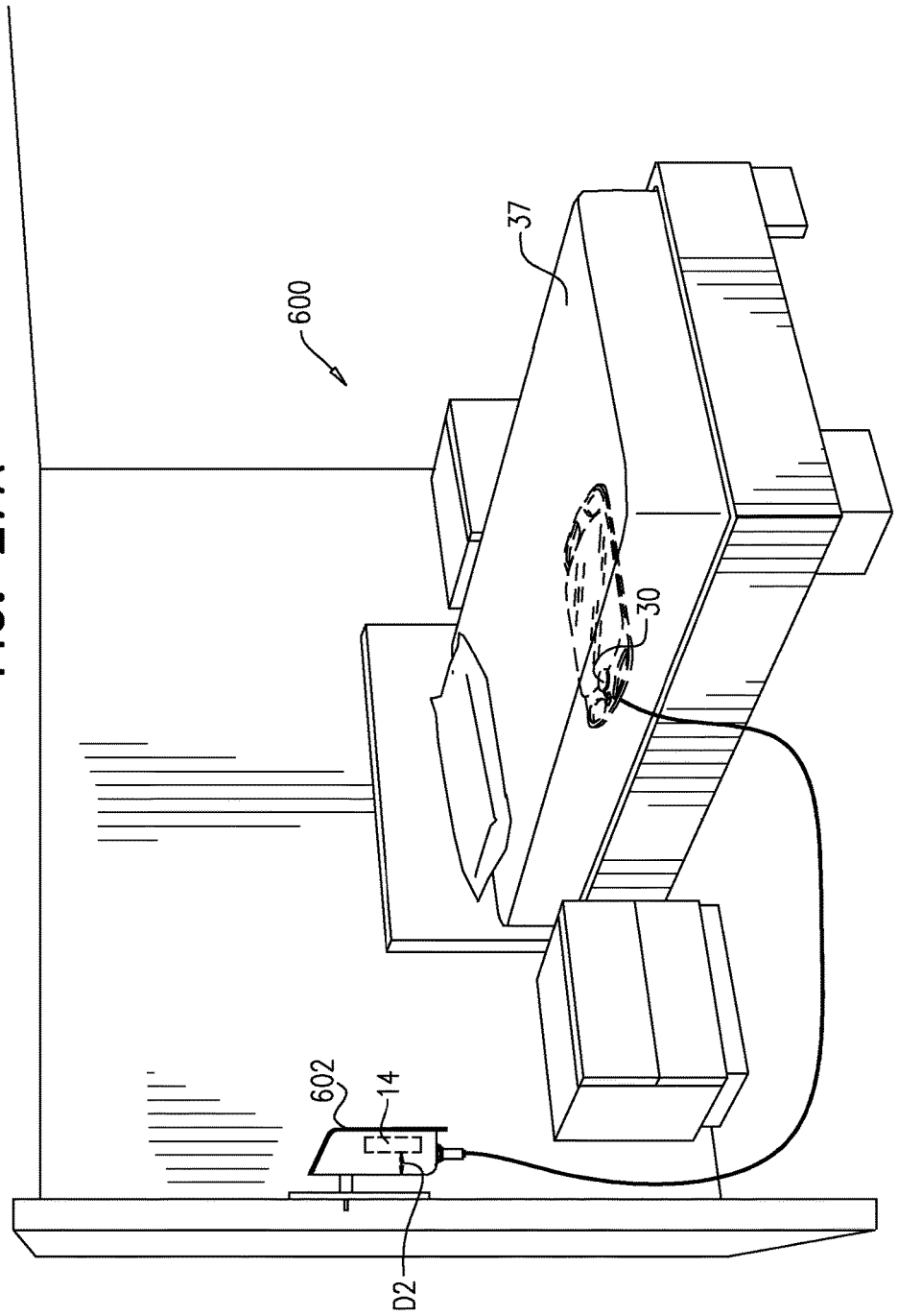

MONITORING A SLEEPING SUBJECT

CROSS-REFERENCE TO RELATED APPLICATIONS

The present application is a continuation-in-part of:
(a) U.S. application Ser. No. 13/906,325 to Halperin, issued as U.S. Pat. No. 8,882,684, filed May 30, 2013, which is a continuation-in-part of:
  (i) U S patent application Ser. No. 13/389,200, filed Jun. 13, 2012 (published as US 2012/0253142, now abandoned), which is a US national phase of International Application PCT/IL2011/050045 (published as WO 12/077113), filed Dec. 07, 2011, which claims the benefit of the following U.S. provisional patent applications:
    U.S. Provisional Application 61/420,402, filed Dec. 07, 2010;
    U.S. Provisional Application 61/439,971, filed Feb. 07, 2011; and
    U.S. Provisional Application 61/561,962, filed Nov. 21, 2011; and
  (ii) International Application PCT/IL2013/050283 (published as WO 13/150523), filed Mar. 24, 2013, which claims priority from the following U.S. provisional patent applications:
    U.S. Provisional Patent Application No. 61/618,792, filed Apr. 01, 2012;
    U.S. Provisional Patent Application No. 61/696,326, filed Sep. 04, 2012;
    U.S. Provisional Patent Application No. 61/698,736, filed Sep. 10, 2012;
    U.S. Provisional Patent Application No. 61/722,810, filed Nov. 06, 2012;
    U.S. Provisional Patent Application No. 61/725,513, filed Nov. 13, 2012;
    U.S. Provisional Patent Application No. 61/739,033, filed Dec. 19, 2012;
    U.S. Provisional Patent Application No. 61/748,081, filed Jan. 01, 2013;
    U.S. Provisional Patent Application No. 61/756,003, filed Jan. 24, 2013;
    U.S. Provisional Patent Application No. 61/757,739, filed Jan. 29, 2013;
    U.S. Provisional Patent Application No. 61/764,541, filed Feb. 14, 2013; and
    U.S. Provisional Patent Application No. 61/772,553, filed Mar. 05, 2013; and
(b) International Application PCT/IL2014/050644 (published as WO 15/008285), filed Jul. 17, 2014, which claims the benefit of (i) U.S. Provisional Application 61/847,579, filed Jul. 18, 2013, and (ii) U.S. Provisional Application 61/926,499, filed Jan. 13, 2014.

Each of the above-referenced applications is assigned to the assignee of the present application and is incorporated herein by reference.

FIELD OF THE INVENTION

The present invention relates generally to monitoring subjects and predicting and monitoring abnormal physiological conditions and treating those conditions, and specifically to methods and apparatus for predicting and monitoring abnormal physiological conditions by non-contact measurement and analysis of characteristics of physiological and/or physical parameters.

BACKGROUND

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), sleep apnea and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiology's related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

SUMMARY OF THE INVENTION

Some applications of the present invention provide methods and systems for monitoring subjects for the occurrence or recurrence of a physiological event, for example, a chronic illness or ailment. This monitoring assists the subject or healthcare provider in treating the ailment or mitigating the effects of the ailment. Some applications of the present invention provide techniques for monitoring vital and non-vital signs using automated sensors and electronic signal processing, in order to detect and characterize the onset of a physiological event, and, for some applications, to treat the event, such as with therapy or medication.

In some cases, a subject is monitored not to predict or track disease situations, but rather, in order to allow the subject to optimize long term health and fitness as part of a 'wellness' approach, and/or in order to control household devices (e.g., bedside lamps, mobile phones, alarm clocks, etc.) in a manner that increases their usefulness and/or minimizes the disturbances causes by these devices.

There is therefore provided, in accordance with some applications of the present invention, apparatus for use with a subject who shares a bed with a second person, the apparatus including:

a motion sensor configured to:
   detect motion of the subject without contacting the subject, without contacting clothes the subject is wearing, without viewing the subject, and without viewing clothes the subject is wearing,
   detect motion of the second person without contacting the second person, without contacting clothes the second person is wearing, without viewing the second person, and without viewing clothes the second person is wearing, and
   generate a motion signal in response to detecting motion of the subject and motion of the second person; and a control unit configured to:
   identify components of the motion signal that were generated in response to motion of the subject, by distinguishing between components of the motion signal that were generated in response to motion of the subject, and components of the motion signal that were generated in response to motion of the second person,
   analyze the components of the motion signal that were generated in response to motion of the subject, and generate an output in response thereto.

In some applications, the control unit is configured to identify components of the motion signal that were generated in response to motion of the subject, by identifying components of the motion signal that have a signal strength that is a characteristic signal strength of a motion signal of the subject.

In some applications, the control unit is configured to identify components of the motion signal that were generated in response to motion of the subject by identifying components of the motion signal that have a pattern that is a characteristic pattern of motion of the subject.

In some applications, the apparatus further includes a weight sensor that is configured to detect when the subject is lying above the motion sensor, and the control unit is configured to identify the components of the motion signal that were generated in response to motion of the subject, in response to a signal that is generated by the weight sensor.

In some applications, the motion sensor is configured to facilitate the identification of components of the motion signal that were generated in response to motion of the subject, by strengthening a signal strength of the components of the motion signal that are generated in response to motion of the subject.

In some applications, the apparatus is for use with a subject who lies on a mattress, and the sensor is configured to be placed at a position selected from the group consisting of: underneath the mattress at a position that is higher than a head of the subject is typically placed, and adjacent to and in contact with a side of the mattress.

In some applications, the sensor is configured such as to facilitate identification, by the control unit, of components of the motion signal that were generated in response to a longitudinal cardio-ballistic effect of the subject.

In some applications, the control unit is configured to identify components of the motion signal that were generated in response to respiratory motion of the subject.

In some applications, the control unit is configured to identify components of the motion signal that were generated in response to cardiac motion of the subject.

In some applications, the control unit is configured to identify components of the motion signal that were generated in response to large body-movement of the subject.

In some applications, the control unit is further configured to:
   analyze the motion signal,
   in response thereto, identify an effect of large body-movement of the second person on sleep of the subject, and
   in response thereto, generate a sleep-disturbance output.

In some applications, the sleep-disturbance output includes an assessment of an effectiveness of a parameter at reducing the effect of the large body-movement of the second person on the sleep of the subject, the control unit being configured to generate the assessment of the effectiveness of the parameter.

In some applications, the parameter is selected from the group consisting of: a parameter of a mattress on which the subject is sleeping, a parameter of the bed, a sleeping arrangement of the subject and the second person, and a room-environment parameter, the control unit being configured to generate the assessment of the effectiveness of the selected parameter.

In some applications, the sleep-disturbance output includes a recommendation to reduce the effect of the large body-movement of the second person on the sleep of the subject by adjusting an adjustable parameter, the control unit being configured to generate the recommendation.

In some applications, the adjustable parameter is selected from the group consisting of: a parameter of a mattress on which the subject is sleeping, a parameter of the bed, a sleeping arrangement of the subject and the second person, and a room-environment parameter, the control unit being configured to generate the recommendation to adjust the selected parameter.

In some applications, the sleep-disturbance output includes instructions to a device to adjust an adjustable parameter, the control unit being configured to generate the instructions.

In some applications, the adjustable parameter is selected from the group consisting of: a parameter of a mattress on which the subject is sleeping, a parameter of the bed, a sleeping arrangement of the subject and the second person, and a room-environment parameter, the control unit being configured to generate the instructions to the device to adjust the selected parameter.

In some applications,
   the motion sensor includes a mechanical-filtering element configured to reduce a response of the motion sensor to motion of the second person, relative to motion of the subject, and
   the control unit is further configured to:
      by analyzing the motion signal, assess an effectiveness of the mechanical-filtering element at reducing the response of the motion sensor to motion of the second person, and
      generate an output in response thereto.

In some applications, the control unit is configured to identify that a portion of the motion signal was generated in response to motion of the second person, and not in response to motion of the subject, by identifying that the portion exhibits ringing.

In some applications, the motion sensor consists of a single motion sensor.

The present invention will be more fully understood from the following detailed description of embodiments thereof, taken together with the drawings, in which:

BRIEF DESCRIPTION OF THE DRAWINGS

FIG. 8 is a schematic illustration of a method for detecting ectopic heartbeats, in accordance with some applications of the present invention;

FIG. 11 is a schematic illustration of apparatus comprising a motion sensor, control unit, and speaker, in accordance with some applications of the present invention;

FIG. 27A is a schematic illustration of apparatus comprising a motion sensor, a mains-power-connection device, and a control unit, in accordance with some applications of the present invention;

DETAILED DESCRIPTION OF APPLICATIONS

Figure 1:
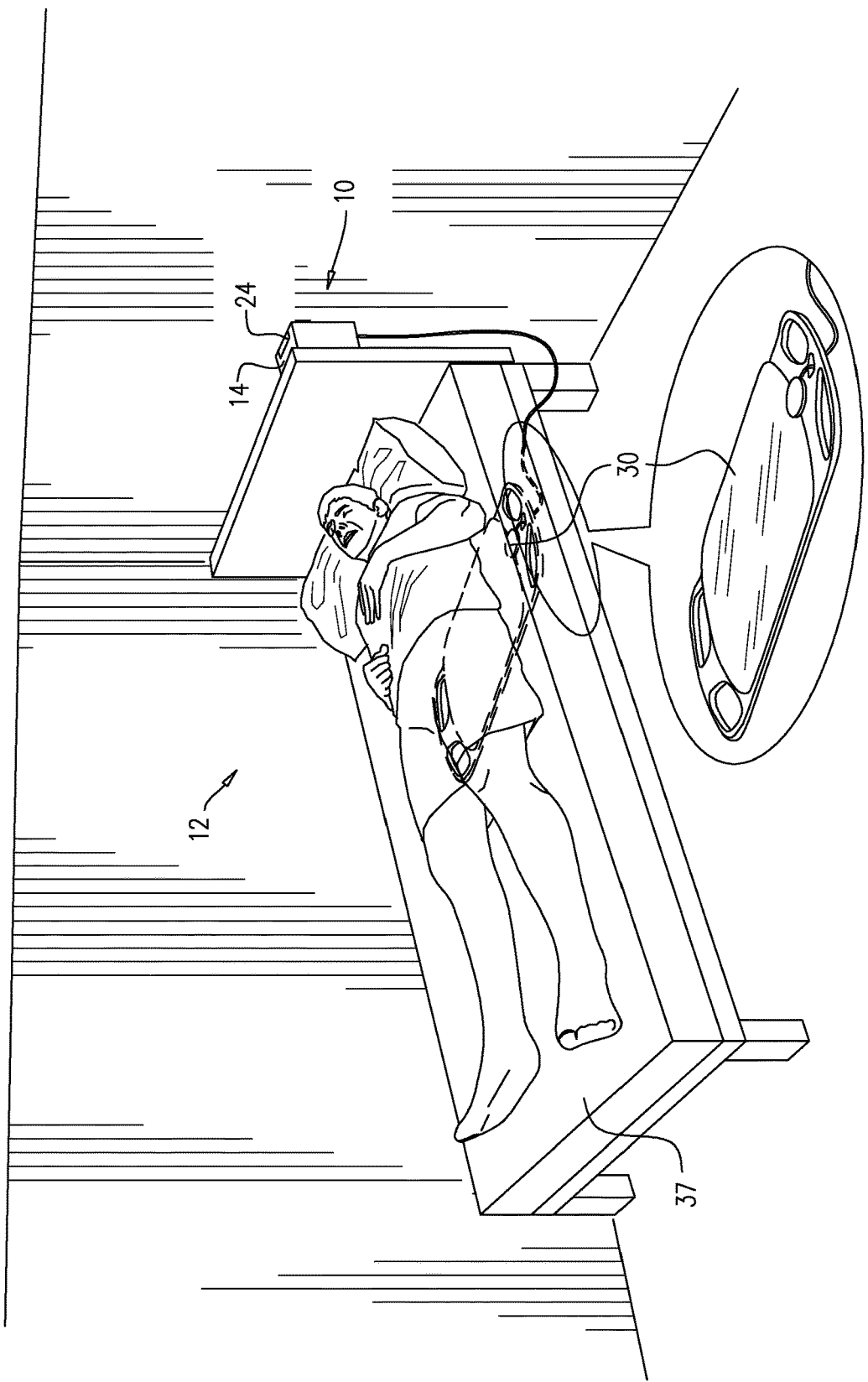
FIG. 1 is a schematic illustration of a system for monitoring a chronic medical condition of a subject, in accordance with some applications of the present invention.

FIG. 1 is a schematic illustration of a system 10 for monitoring a chronic medical condition of a subject 12, in accordance with some applications of the present invention. System 10 typically comprises a motion sensor 30, a control unit 14, and a user interface (U/I) 24. System 10 is generally similar to system 10 described in US 2011/0112442 to Meger and in US 2012/0253142 to Meger, both of which applications are incorporated herein by reference, except for differences described herein. For some applications, user interface 24 is integrated into control unit 14, as shown in the figure, while for other applications, the user interface and the control unit are separate units. Typically, user interface 24 includes a display. For some applications, motion sensor 30 is integrated into control unit 14, in which case user interface 24 is either also integrated into control unit 14 or remote from control unit 14. For some applications, control unit 14 and/or user interface 24 of system 10 are implemented in a mobile device (such as a cellular phone, a pager, and/or a tablet computer).

In some applications of the present invention, motion sensor 30 is a "non-contact sensor," that is, a sensor that does not contact the body of subject 12 or clothes subject 12 is wearing. In other applications, motion sensor 30 does contact the body of subject 12 or clothes subject 12 is wearing. In the former applications, because motion sensor 30 does not come in contact with subject 12, motion sensor 30 detects motion of subject 12 without discomforting or inconveniencing subject 12. For some applications, motion sensor 30 performs sensing without the knowledge of subject 12, and even, for some applications, without the consent of subject 12. For some applications, motion sensor 30 does not have a direct line of sight with subject 12 or the clothes subject 12 is wearing.

(It is noted that generally, in the present description, the term "motion sensor 30" is used to refer to a sensor that does not contact or view the subject or clothes the subject is wearing, while the term "sensor 316" refers more generally to any type of sensor, e.g., a sensor that includes an electromyographic sensor and/or an imaging sensor. Thus, a phrase such as "sensor 316 (e.g., motion sensor 30)" should be construed to mean that the scope of the described invention includes the use of any type of sensor, but specifically, a non-contact and non-viewing sensor may be used.)

Motion sensor 30 may comprise a ceramic piezoelectric sensor, vibration sensor, pressure sensor, or strain sensor, for example, a strain gauge, configured to be installed under a resting surface 37, and to sense motion of subject 12. The motion of subject 12 sensed by sensor 30, during sleep, for example, may include regular breathing movement, heartbeat-related movement, and other, unrelated body movements, as discussed below, or combinations thereof. For some applications, sensor 30 comprises a standard communication interface (e.g. USB), which enables connection to standard monitoring equipment.

Figure 2:
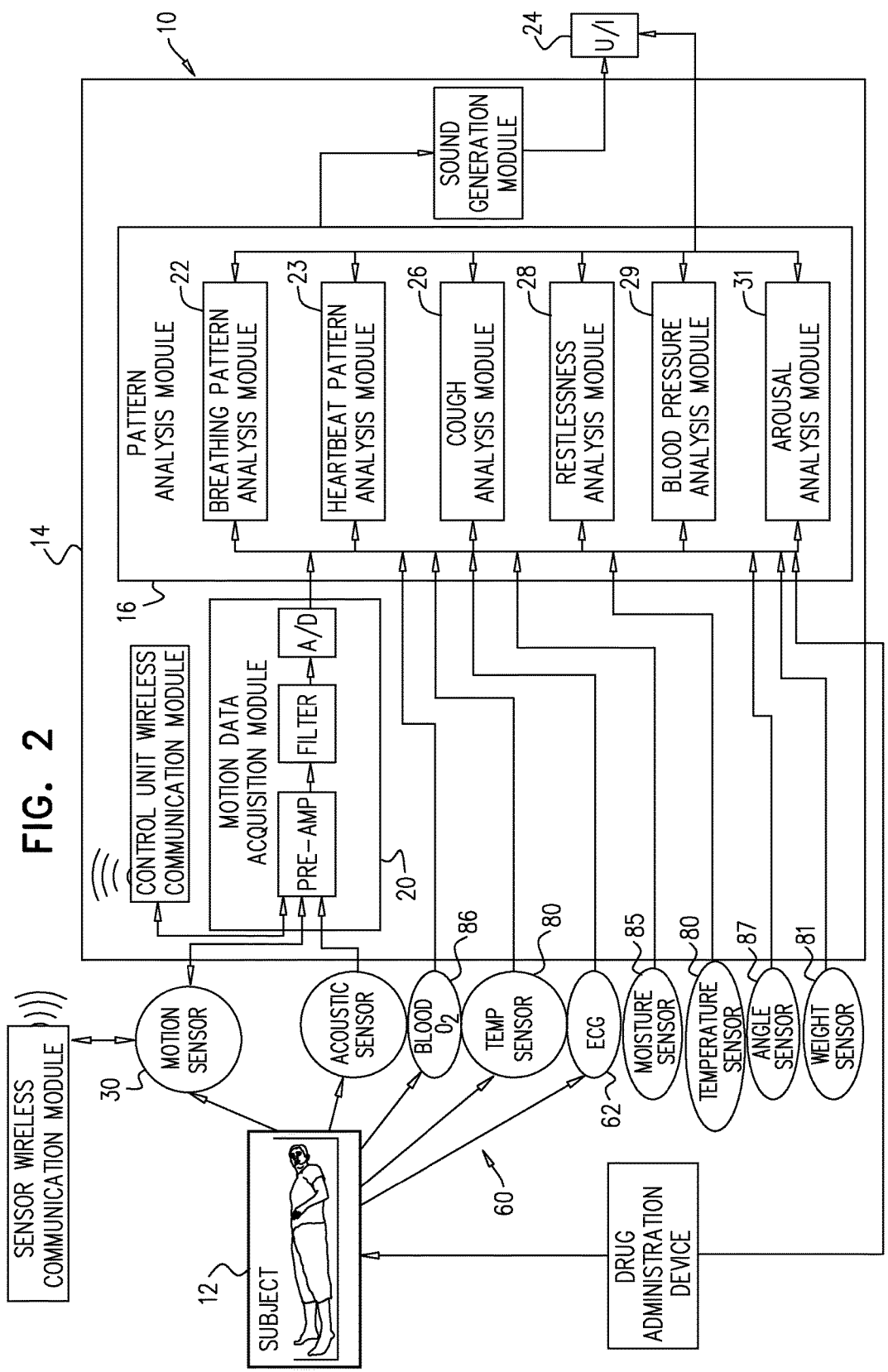
FIG. 2 is a schematic block diagram illustrating components of a control unit of the system of FIG. 1, in accordance with some applications of the present invention.

As shown in FIG. 2 (described herein below), for some applications, in addition to wirelessly-enabled motion sensor 30, control unit 14 is coupled to one or more additional sensors 60 applied to subject 12, such as a blood oxygen monitor 86 (e.g., a pulse oximeter/photoplethysmograph), an ECG monitor 62, weight sensor 81 (e.g. a weight sensor embedded into a bed as manufactured by Stryker Inc. of Kalamazoo, Mich.), a moisture sensor 85, an angle sensor 87, and/or a temperature sensor 80. In accordance with respective applications, one or more of sensors 60 is a contact sensor or a contact-less sensor.

Most of the experimental results presented in the present application were measured using one or more piezoelectric sensors. Nevertheless, the scope of the present invention includes performing measurements with other motion sensors 30, such as other pressure gauges or accelerometers.

Figure 6B:
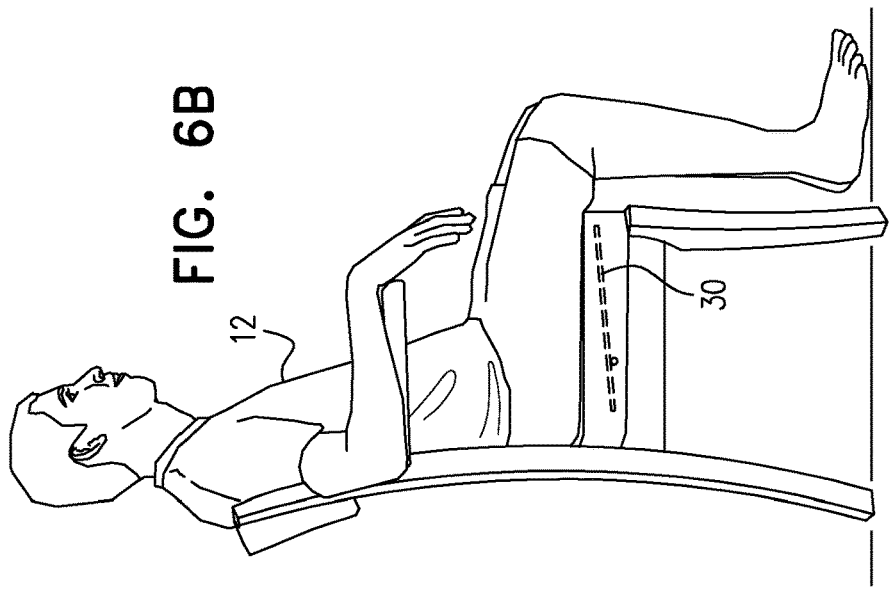
FIGS. 6A-B are schematic illustrations of a motion sensor coupled to a chair, in accordance with some applications of the present invention.
Figure 6A:
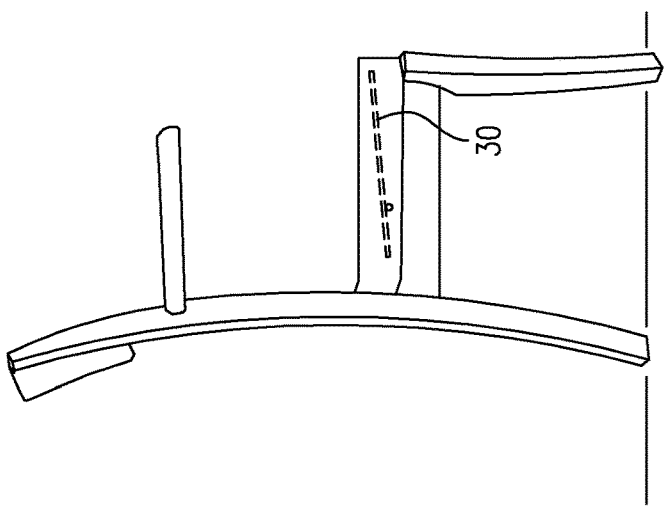

Motion sensor 30 is typically coupled to a resting surface 37 upon which the subject rests. For example, as shown in FIG. 1, motion sensor 30 may be placed under a mattress of a bed, and may sense motion of the subject while the subject is in the bed, and generate a motion sensor signal in response thereto. Alternatively or additionally, as shown in FIGS. 6A-B and as described in further detail in US 2013/0267791 to Halperin, which is incorporated herein by reference, motion sensor 30 may be coupled to a chair (e.g., a wheelchair) upon which the subject sits, and may sense motion of the subject while the subject is sitting in the chair, and generate a motion sensor signal in response thereto. For some applications, system 10 includes a first motion sensor which is under the mattress of the subject's bed, and a second motion sensor 30, which is coupled to a chair in the subject's room. The first sensor senses motion of the subject while the subject is in the bed, and the second motion sensor senses motion of the subject while the subject is in the chair. System 10 monitors the subject responsively to both the first and the second sensor signals, as described in US 2013/0267791 to Halperin, which is incorporated herein by reference. For some applications, a plurality of motion sensors are coupled to a single resting surface, and are used as motion sensor 30. For example, two or more motion sensors that are disposed under the subject's mattress may be used as motion sensor 30. Alternatively, only a single sensor is coupled to a given resting surface.

FIG. 2 is a schematic block diagram illustrating components of control unit 14 in accordance with some applications of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, pattern analysis module includes additional modules and/or functionalities to those shown in FIG. 2. For example, pattern analysis module 16 may include one or more of the additional modules and/or functionalities shown in FIG. 4. For some applications, two or more of analysis modules 20, 22, 23, 26, 28, 29, and 31 (and/or the additional modules and/or functionalities) are packaged in a single housing. For other applications, the modules are packaged separately (for example, so as to enable remote analysis, by one or more of the pattern analysis modules, of breathing signals acquired locally by data acquisition module 20).

User interface 24 typically comprises a dedicated display unit, such as an LCD or CRT monitor. Alternatively or additionally, the user interface 24 comprises a wireless or wired communication port for relaying the acquired raw data and/or processed data to a remote site for further analysis, interpretation, expert review, and/or clinical follow-up. For example, the data may be transferred over a telephone line, and/or over the Internet or another wide-area network, either wirelessly or via wires.

Breathing pattern analysis module 22 is configured to extract breathing patterns from the motion data, as described herein below with reference to FIG. 3, and heartbeat pattern analysis module 23 is configured to extract heartbeat patterns from the motion data. Alternatively or additionally, system 10 comprises another type of sensor, such as an acoustic or air-flow sensor attached or directed at the subject's face, neck, chest, and/or back, or placed under the mattress.

Figure 3:
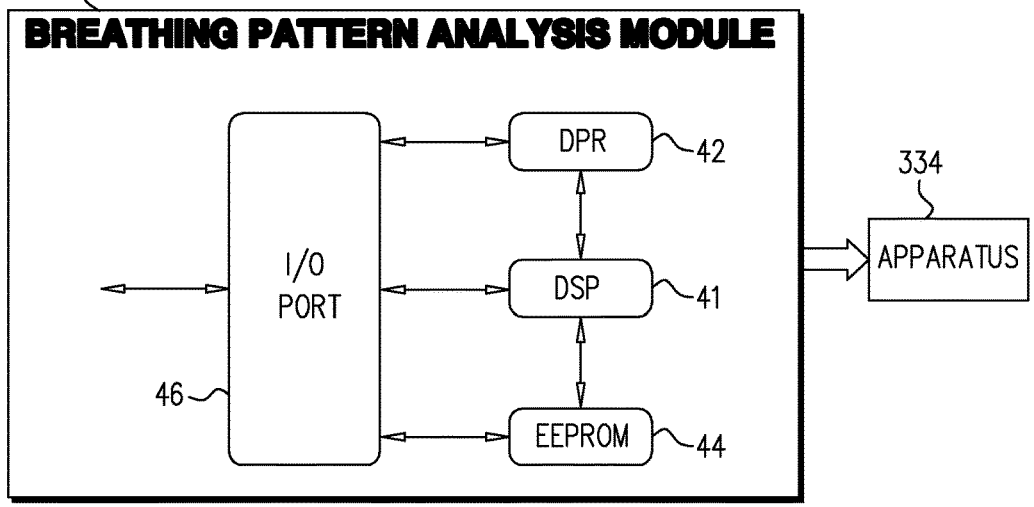
FIG. 3 is a schematic block diagram illustrating a breathing pattern analysis module of the control unit of FIG. 2, in accordance with some applications of the present invention.

FIG. 3 is a schematic block diagram illustrating components of breathing pattern analysis module 22, in accordance with some applications of the present invention. Breathing pattern analysis module 22 analyzes changes in breathing patterns, typically during sleep. Breathing pattern analysis module 22 typically comprises a digital signal processor (DSP) 41, a dual port RAM (DPR) 42, an EEPROM 44, and an I/O port 46. Modules 23, 26, 28, 29, and 31 may be similar to module 22 shown in FIG. 3. For example, modules 23, 26, 28, 29, and 31 may include a digital signal processor, a dual port RAM, an EEPROM, and an I/O port similar to digital signal processor 41, dual port RAM 42, EEPROM 44, and I/O port 46. Breathing pattern analysis module 22 may be used (e.g., to facilitate ascertaining a sleep stage of a subject) with various apparatus and methods described herein, such as, for example, apparatus 334, described herein below with reference to FIGS. 19-20.

In some applications of the present invention, data acquisition module 20 is configured to non-invasively monitor breathing and heartbeat patterns of subject 12. Breathing pattern analysis module 22 and heartbeat pattern analysis module 23 are configured to extract breathing patterns and heartbeat patterns respectively from the raw data generated by data acquisition module 20, and to perform processing and classification of the breathing patterns and the heartbeat patterns, respectively. Breathing pattern analysis module 22 and heartbeat pattern analysis module 23 are configured to analyze the respective patterns in order to (a) predict an approaching clinical episode, such as an asthma attack, heart condition-related lung fluid buildup, sepsis, cardiac arrest, or respiratory depression, and/or (b) monitor the severity and progression of a clinical episode as it occurs. User interface 24 is configured to notify subject 12 and/or a clinician of the predicted or occurring episode. Prediction of an approaching clinical episode facilitates early preventive treatment, which generally improves outcomes, e.g., by lowering required dosages of medication, and/or lowering mortality and morbidity. When treating a hospitalized subject in a general care ward, for example, an earlier identification of subject deterioration may prevent the need to admit the subject to the ICU, shorten his length of stay, and increase the likelihood for successful recovery to discharge.

Breathing pattern analysis module 22 and heartbeat pattern analysis module typically derive breathing patterns and heartbeat patterns from the raw data in accordance with the techniques described in US 2011/0112442 to Meger and in US 2012/0253142 to Meger, both of which applications are incorporated herein by reference. In general, system 10 is configured to monitor clinical parameters of the subject, and to generate alerts and/or reports in response thereto, in a generally similar manner to system 10 described US 2011/0112442 to Meger and in US 2012/0253142 to Meger, both of which applications are incorporated herein by reference.

Figure 4:
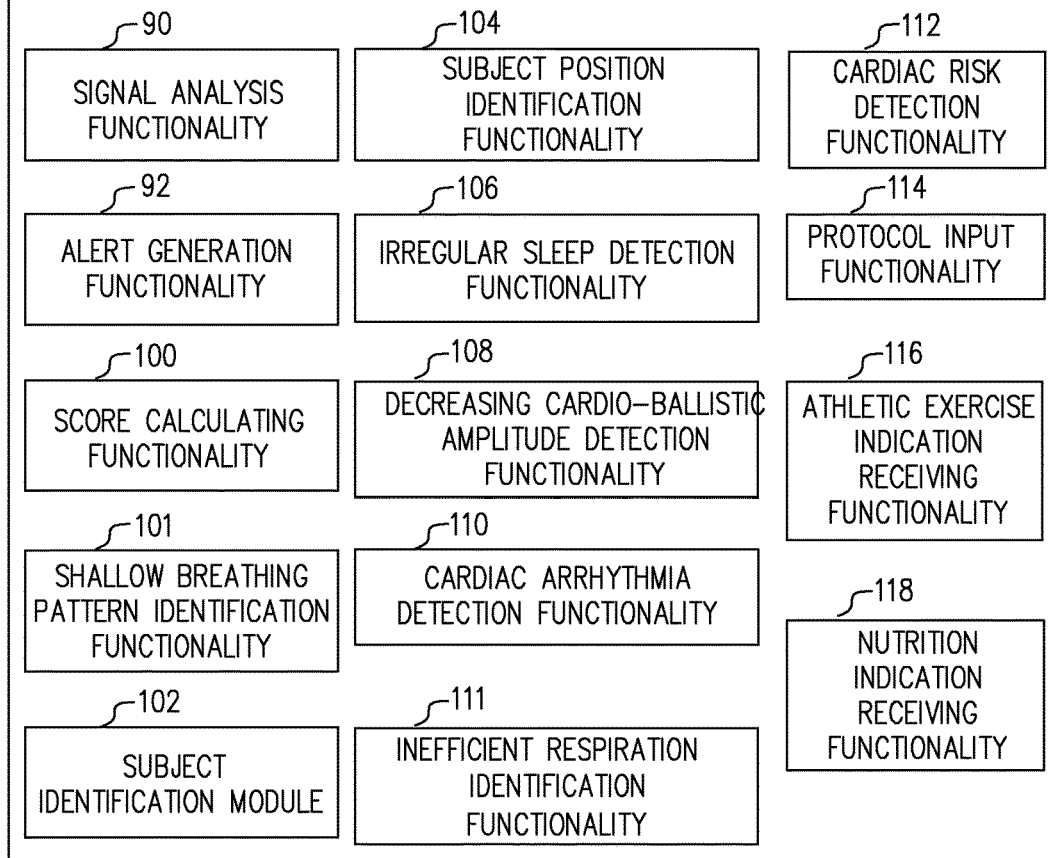
FIG. 4 is a schematic block diagram illustrating additional components of a pattern analysis module of the control unit of FIG. 2, in accordance with some applications of the present invention.

Reference is now made to FIG. 4, which is a schematic illustration of functionalities and/or modules that are included in pattern analysis module 16, in addition to the modules of the pattern analysis module that are shown in FIG. 2, in accordance with some applications of the present invention. Typically, pattern analysis module includes signal analysis functionality 90. The signal analysis functionality is configured to analyze the signals received from the sensors that provide input to control unit 14 and to determine a condition of the subject and/or generate an output (e.g., an alert), in response thereto. Many of the functionalities of control unit 14 that are described herein as being performed by pattern analysis module 16 are performed by the signal analysis functionality of the pattern analysis module. Pattern analysis module typically further includes alert-generation-functionality 92 that is configured to generate an alert in response to the signal analysis that is performed by the signal analysis functionality. For example, alerts may be generated on pagers of clinicians, at user interface (e.g., display) 24, and/or at a central monitoring system user interface (e.g., display). For some applications, pattern analysis module includes score calculating functionality 100 configured to calculate a score in response to the signal analysis that is performed by the signal analysis functionality. In accordance with some applications, pattern analysis module includes additional functionalities and/or modules, such as a shallow-breathing-pattern-identification functionality 101, a subject identification module 102, a subject-position-identification functionality 104, an irregular-sleep-detection functionality 106, a decreasing-cardioballistic-amplitude-detection functionality 108, a cardiac-arrhythmia-detection functionality 110, an inefficient respiration identification functionality 111, a cardiac-risk-detection functionality 112, protocol input functionality 114, athletic-exercise-receiving functionality 116, and/or nutrition-receiving functionality 118. The functions of at least some of the additional functionalities and/or modules are described in further detail herein below.

For some applications, the pattern analysis module includes subject identification module 102. The subject identification module is configured to determine which motion signals detected by motion sensor 30 were generated by the subject. For example, in cases in which the subject who is being monitored is sharing a bed with a second person (e.g., the subject's partner), the subject identification module determines which components of the motion signal detected by the motion sensor were generated by the subject and which were generated by the second person. The pattern analysis module then analyzes the components of the signal that were generated by the subject, and generates outputs (such as alerts), as described herein, in response thereto. For some applications, the subject identification module is configured to determine when the subject is out of bed by determining that the motion signal detected by the motion detector is being generated by the second person. For some applications, the subject identification module is configured to determine which components of the motion signal detected by the motion sensor were generated by the subject even when the subject is smaller than the second person.

For some applications, subject identification module 102 is configured to determine which components of the motion signal detected by motion sensor 30 were generated by the subject using one or more of the following techniques:

a. The subject identification module identifies patterns (e.g., a respiratory pattern, a heart rate pattern, and/or a motion pattern, e.g., a large body-movement pattern) that are characteristic of, respectively, the subject and the second person. The subject identification module then determines that components of the signal that correspond to the characteristic patterns of the subject have been generated by the subject. For some applications, the subject identification module learns characteristic patterns of the subject by utilizing a weight sensor (e.g., as described herein below), and/or or utilizing long term average patterns of the subject. For some applications, in response to an input to system 10, the pattern identification module operates in a learning mode, in which the module learns characteristic patterns of the subject.

b. The subject identification module identifies characteristic signal strengths generated, respectively, by the subject and by the second person. For example, the sensor may be disposed underneath the subject who lies on a first side of the bed and the second person may typically lie on the second side of the bed. In such cases, signals generated by the subject are typically characterized as being of greater strength than those generated by the second person. Alternatively, the subject may be smaller than the second person, and may therefore generate signals that are characterized as being weaker than signals generated by the second person.

Figure 33A:
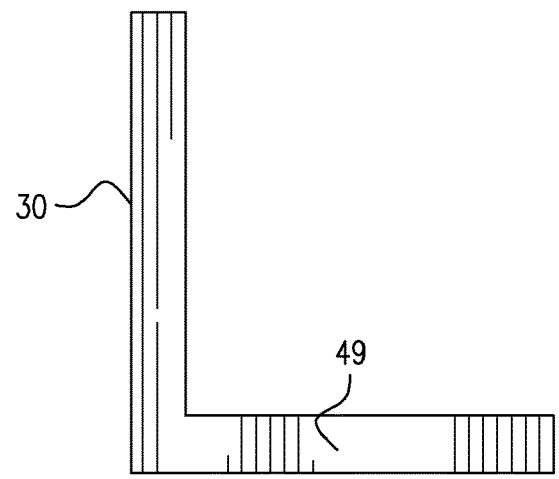
FIGS. 33A-B are schematic illustrations of respective views of a motion sensor, in accordance with some applications of the present invention.
Figure 33B:
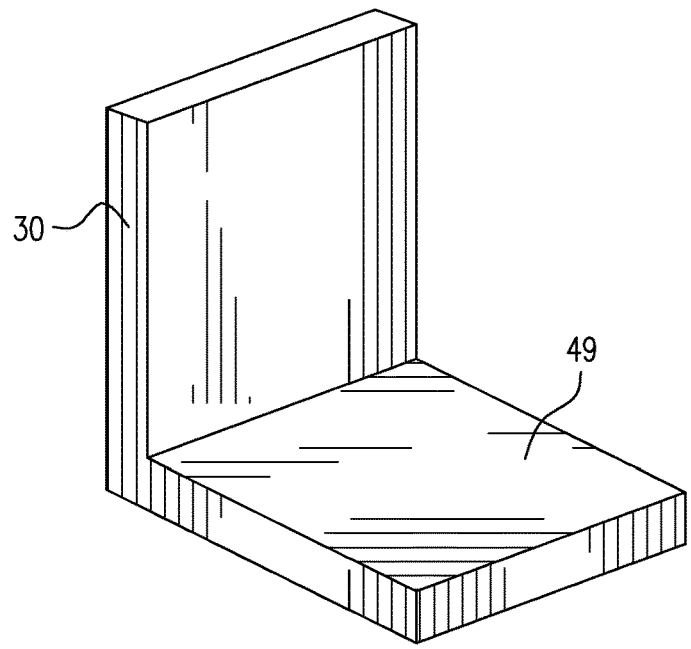

Reference is now made to FIGS. 33A-B, which are schematic illustrations of respective views of motion sensor 30, in accordance with some applications of the present invention. For some applications, motion sensor 30 is configured to facilitate determination by subject identification module 102 of which components of the motion signal were generated by the subject. For example, the sensor may be placed in a position, and/or shaped, such as to strengthen the signal that is received from the subject. For some applications, the sensor is placed underneath the subject's mattress at a position higher than where the subject rests his/her head, such that the strongest signals that the sensor receives are those generated by the longitudinal cardio-ballistic effect of the subject. Alternatively or additionally, at least a portion of the sensor is placed adjacent to and in contact with a side of the subject's mattress (e.g., the head of the subject's mattress), and not underneath the mattress. For some applications, the motion sensor comprises at least a portion of an L-shaped structure, as shown in FIGS. 33A-B. The structure is shaped to define horizontal and vertical portions that form approximately (or precisely) a right angle with one another. The horizontal portion of the structure is placed underneath the subject's mattress, and the vertical portion of the structure is placed adjacent to and in contact with a side of the subject's mattress (e.g., the head of the subject's mattress). For some applications, the horizontal portion of the structure does not perform any sensing functionalities but acts as a support element 49 for supporting the vertical portion adjacent to and in contact with a side of the subject's mattress (e.g., the head of the subject's mattress), the vertical portion acting as sensor 30.

Alternatively or additionally, a different support element is used to support sensor 30 at a position adjacent to and in contact with a side of the subject's mattress (e.g., the head of the subject's mattress). For example, a compressible member (such as a cushion) may be placed between the side of the mattress and a surface (e.g., a wall or a headboard) that is adjacent to the side of the mattress, and may be configured to hold the sensor against the head of the mattress, by expanding against the side of the mattress. For some applications, the sensor is disposed on a stretchable band (e.g., an elastic band). The band is stretched in order to facilitate placement of the band around the sides of the subject's mattress, and the band then shrinks, such as to maintain the sensor adjacent to and in contact with a side of the subject's mattress (e.g., the head of the subject's mattress). For some applications, the sensor is not disposed on a stretchable band, but the sensor is maintained adjacent to and in contact with a side of the subject's mattress (e.g., the head of the subject's mattress), using a stretchable band.

For some applications, the motion sensor includes a weight sensor that is configured to measure a weight that is placed on top of the weight sensor, and to identify that the subject is lying above the motion sensor in response thereto. The subject identification module identifies signals from the motion sensor as having been generated by the subject, in response to the signal generated by the weight sensor. For some applications, the weight sensor is used to determine when the subject is directly on top of the weight sensor. In response to determining that the subject is directly on top of the weight sensor, the pattern identification module operates in a learning mode, in which the module learns characteristic patterns of the subject, as described hereinabove. For some applications, respective first and second motion sensors are placed underneath the subject and the second person who uses the bed. Subject identification module 102 determines which components of the motion signal were generated by the subject in response to the signals from both the first and the second motion sensors.

The above-described apparatus and techniques for subject identification may be utilized in combination with other apparatus and techniques described herein, such as, for example, apparatus and techniques described with reference to FIG. 32.

Figure 7:
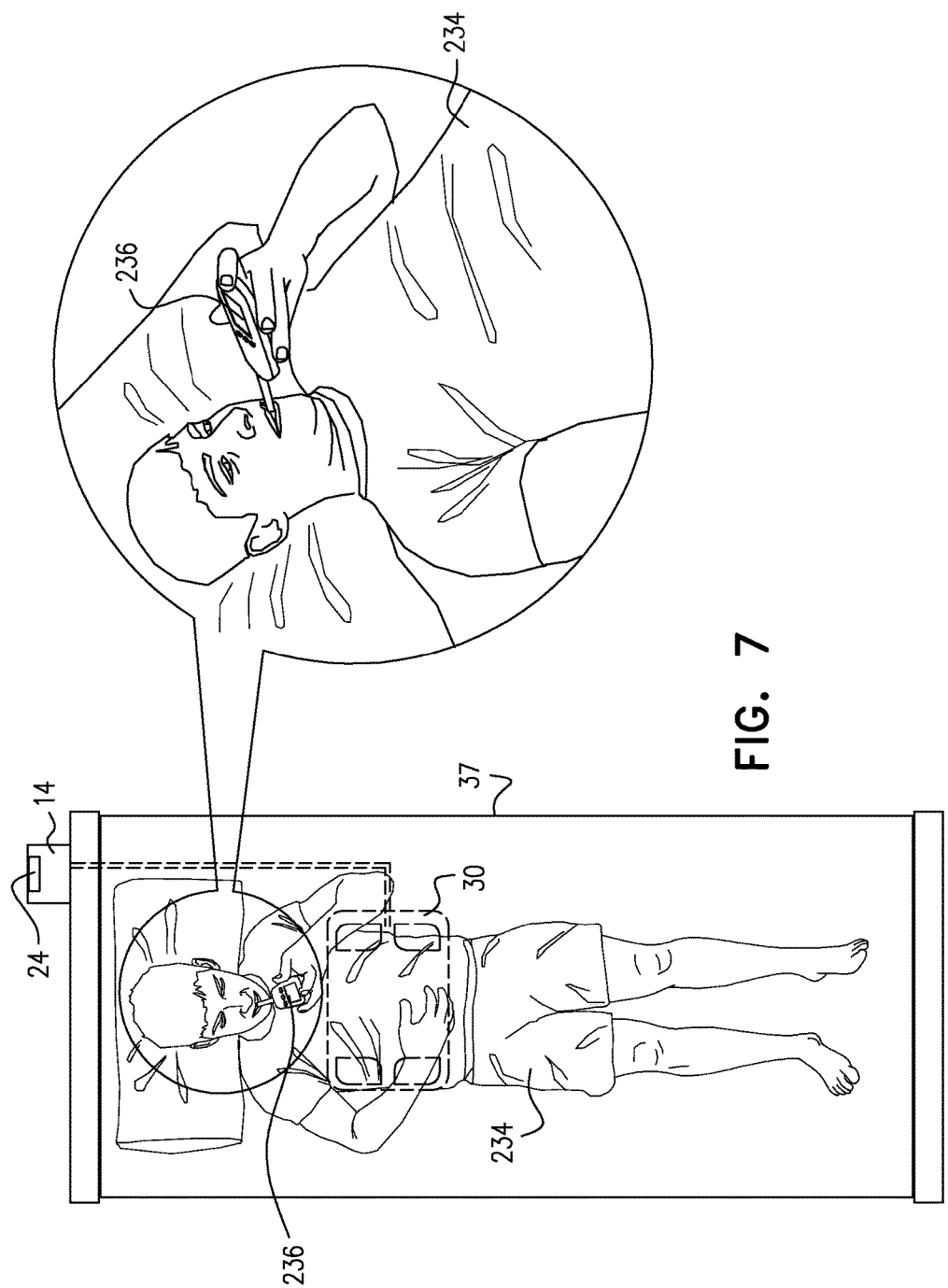
FIG. 7 is a schematic illustration of apparatus for identifying inefficient respiration of a subject, in accordance with some applications of the present invention.

Reference is now made to FIG. 7, which is a schematic illustration of apparatus for identifying inefficient respiration of a subject 234, in accordance with some applications of the present invention. Inefficient respiration may be indicative of a clinical episode related to a respiratory disorder such as obstructive apnea or asthma. Inefficient respiration corresponds to a situation in which the respiration movements are large relative to the volume of respiration flow. This phenomenon may occur in one of the two following ways:

1) Respiration movements are normal, but the volume of respiration flow is abnormally low.

2) The volume of respiration flow is normal, but respiration movements are abnormally large, such as where the subject needs to use upper-body muscles that are normally not used for respiration.

Reference is now made to FIGS. 4 and 7. In some applications, pattern analysis module 16 of control unit 14 comprises inefficient respiration identification functionality 111, as described hereinabove with respect to FIG. 4. The identification of inefficient respiration typically proceeds according to the following steps:

1. A respiration-related motion signal is identified in the mechanical sensor signal that is detected by sensor 30. The amplitude of this signal corresponds to the respiration movements of the subject.

2. The volume of respiration flow is measured, e.g., using a respiration flow meter 236 or sensor 30. (Respiration flow meter 236 may be handled by the subject, or alternatively, by a caregiver, e.g., a physician or nurse.)

3. The inefficient respiration identification functionality calculates a relationship of the amplitude of the respiration-related motion signal to the volume of respiration flow, and inefficient respiration is identified in response to this relationship. For example, the relationship may comprise the quotient of the quantities, e.g., Amplitude of Signal/Volume of Flow. The quotient is compared to a baseline value, and inefficient respiration is identified in response to this comparison. For example, inefficient respiration may be identified if the quotient of Amplitude/Volume is increased by a factor of at least 1.5 relative to the baseline value (e.g., the factor may be 2).

Identifying the inefficient respiration in response to a relationship between the quantities, rather than based on the absolute values of the quantities, helps facilitate the identification of inefficient respiration even if one of the quantities is normal, as described hereinabove.

Reference is now made to FIG. 8, which is a schematic illustration of a method for detecting ectopic heartbeats, e.g., premature ventricular contractions, in accordance with some applications of the present invention. For some applications, heartbeat pattern analysis module 23 (FIG. 2) is configured to detect ectopic beats of a subject. The cardiac signal component of the sensor signal generated by sensor 30 is filtered into a high-frequency component 206 and a low-frequency component 204. (Components 204 and 206 are shown plotted in arbitrary units in FIG. 8.) Since both normal and ectopic beats exhibit high-frequency characteristics indicative of ventricular contraction, the high frequency component indicates both normal and ectopic beats. On the other hand, ectopic beats lack some low-frequency characteristics indicative of blood flow; consequently, the low frequency component generally indicates normal (but not ectopic) beats. Portions 200 of the high-frequency component, corresponding to ventricular contractions of the subject, are identified by heartbeat pattern analysis module 23; a pair of such portions typically indicates a single heartbeat. For each pair of portions 200, a corresponding portion of the low-frequency component is analyzed. If this corresponding portion is indicative of blood flow, e.g., as shown in portions 202 (solid line), the heartbeat is determined to be a normal beat. Conversely, if the corresponding portion is not indicative of blood flow, e.g., as shown in portions 208 (dashed line), the heartbeat is determined to be an ectopic beat. For example, as shown in FIG. 8, a pair 201 of portions 200 corresponds to a portion 202 indicative of blood flow, while a pair 210 of portions 200 corresponds to a portion 208 which is not indicative of blood flow.

In some applications, the time between the two elements of a pair of portions 200 is used to diagnose cardiac conditions such as early heartbeats, missing heartbeats, and low stroke volume.

Filtering of the signal into high-frequency and low-frequency components is typically done using band-pass filters. In some applications, the lower cutoff frequency for the low-frequency band-pass filter may be, for example, at least 1.5 and/or less than 4 Hz (e.g., 2 Hz), while the higher cutoff frequency may be, for example, at least 4.1 and/or less than 7.5 Hz (e.g., 5 Hz). The lower cutoff frequency for the high-frequency band-pass filter may be, for example, at least 6.5 and/or less than 11.5 Hz (e.g., 9 Hz), while the higher cutoff frequency may be, for example, at least 11.6 and/or less than 16.5 Hz (e.g., 14 Hz). In other applications, the lower cutoff frequency for the low-frequency band-pass filter may be, for example, at least 2.5 and/or less than 3.5 Hz, while the higher cutoff frequency may be, for example, at least 4.5 and/or less than 5.5 Hz. The lower cutoff frequency for the high-frequency band-pass filter may be, for example, at least 8.5 and/or less than 9.5 Hz, while the higher cutoff frequency may be, for example, at least 13.5 and/or less than 14.5 Hz.

Figure 5:
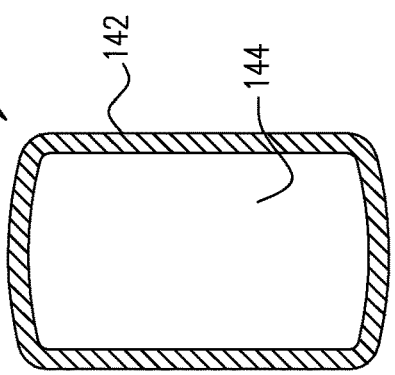
FIG. 5 is a schematic illustration of a semi-rigid sensor plate that is used as a motion sensor, in accordance with some applications of the present invention.

Reference is now made to FIG. 5, which is a schematic illustration of a semi-rigid sensor plate 140 that is used as motion sensor 30, in accordance with some applications of the present invention. For some applications, the sensor is designed and/or placed under the subject's bed such as to detect only motion of the subject who is lying on the side closer to the sensor. The sensor mechanical properties are designed to collect the vibration mechanical signal only locally from the subject lying directly on top or very close to the sensor. This allows mechanical filtering of signals coming from the partner, and detection of only the signal of the subject on top of the sensor. For some applications, edges 142 of the sensor plate are hardened with respect to a central portion 144 of the sensor plate. Typically, this prevents torque from the side of the sensor plate from bending the sensor plate, and allows only direct forces generated from on top of the sensor to affect the plate such as to generate a sensor signal. In some applications, the sensor hardening on the circumference is achieved by mechanically preventing a 2-5 mm rim of the semi-rigid sensing plate from vibrating. This typically substantially reduces the signal generated by the second person as compared to that generated by the subject.

Figure 9A:
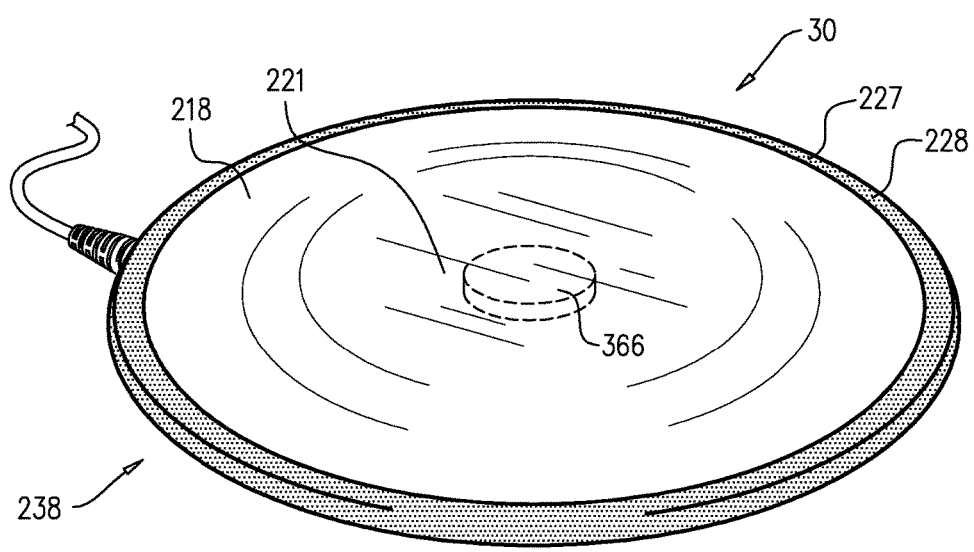
FIGS. 9A-B are schematic illustrations of a motion sensor comprising a sensor plate, in accordance with some applications of the present invention.
Figure 9B:
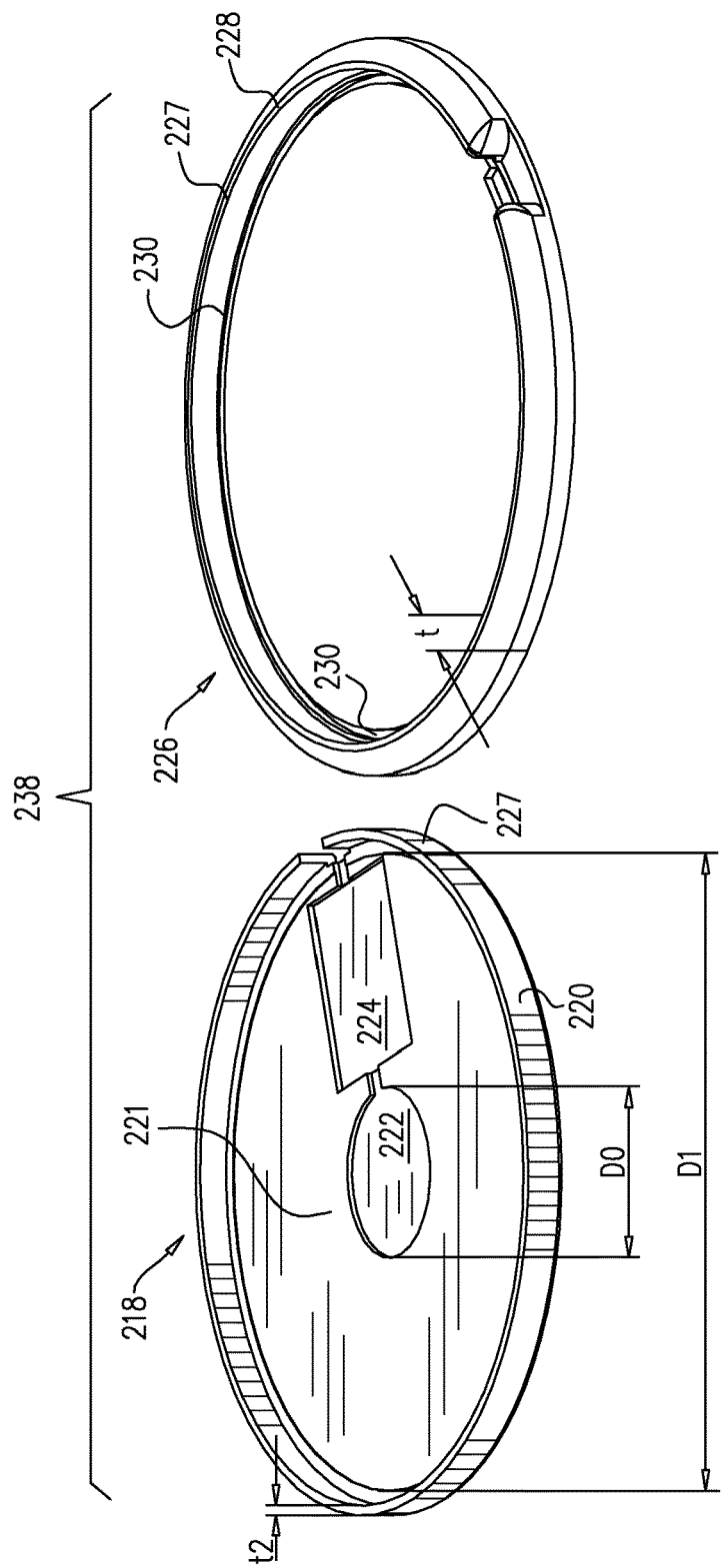
Figure 21:
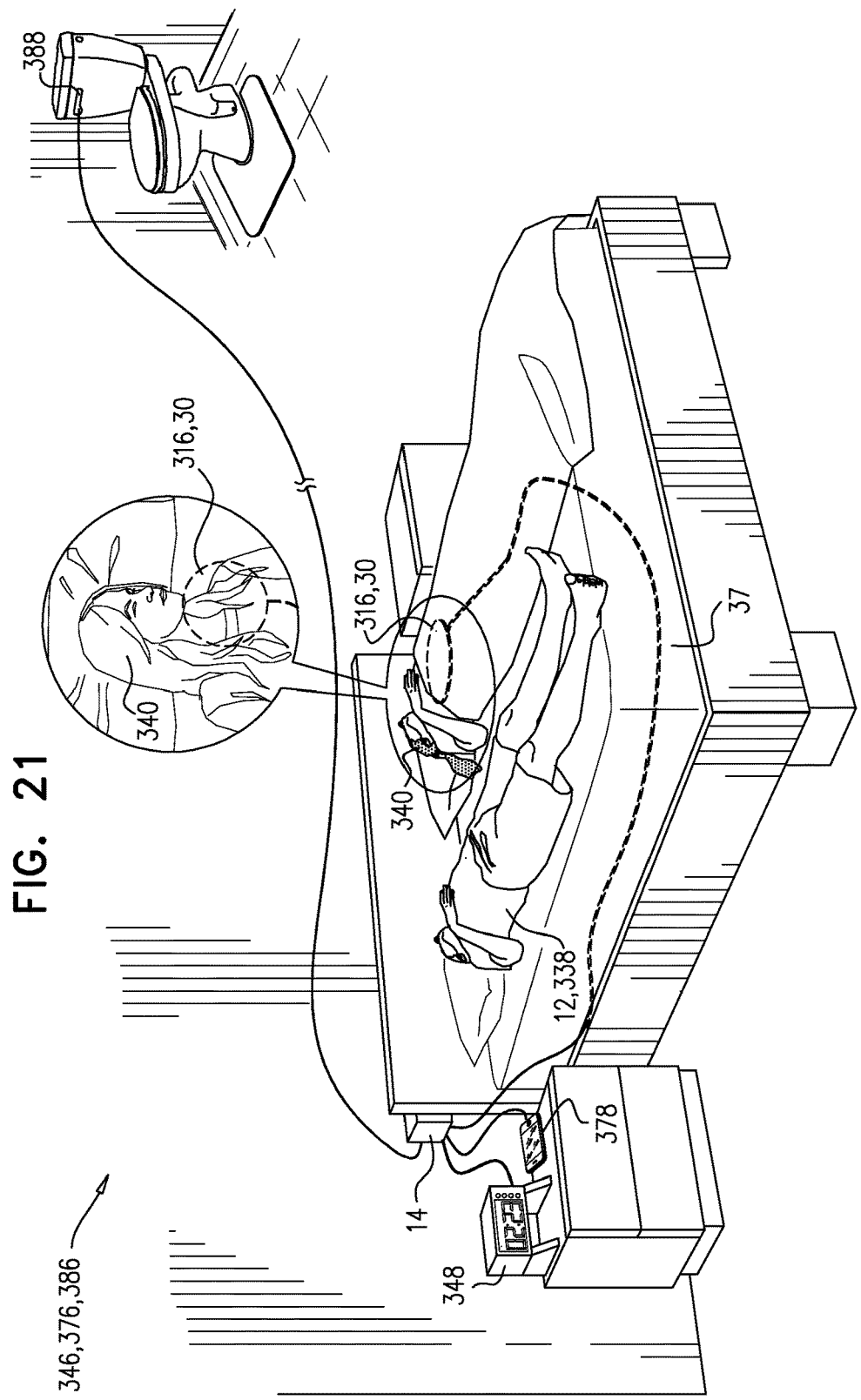
FIG. 21 is a schematic illustration of apparatus for use with a waking mechanism that executes a waking routine to wake a subject who is sleeping near a second person, in accordance with some applications of the present invention.

Reference is now made to FIGS. 9A-B, which are schematic illustrations of motion sensor 30 comprising a sensor plate 238, in accordance with some applications of the present invention. Sensor plate 238 is typically for use with a subject who shares a bed with a second person, e.g., as shown in FIG. 21. As shown in FIG. 9A, sensor plate 238 comprises an edge region 227 that is more rigid than a central portion 221 of the sensor plate, such as to reduce movement of the plate in response to motion of the second person, relative to if edge region 227 of the sensor plate were not more rigid than central portion 221. As described hereinbelow, edge region 227 may take the form of a rigid noise filter rim 228, and/or a rigid sensor-holding-plate rim 220.

Motion sensor 30 is configured to be placed on the bed such that when the subject and the second person are on the bed (e.g., as in FIG. 21), sensor plate 238 is disposed underneath the subject and not disposed underneath the second person. When a sensor element 366 (e.g., a piezo-electric sensor element) is being held by a sensor-holding plate 218 of sensor plate 238, motion sensor 30 detects motion of the subject, by sensor-holding plate 218 moving in response to motion of the subject. (The motion signal generated by motion sensor 30 is then analyzed by control unit 14, as described throughout the present application.) The relative rigidity of edge region 227 generally reduces the extent to which motion of the second person is detected by motion sensor 30, relative to motion of the subject. (In the present description, the word "sensor" may sometimes be used to refer to sensor element 366.)

In some applications, a thickness of the edge region (e.g., thickness t described hereinbelow), measured between an inner perimeter of the edge region and an outer perimeter of the edge region, is at least 2 mm and/or less than 20 mm, e.g., less than 8 mm.

In some applications, as shown in FIG. 9B, sensor plate 238 comprises sensor-holding plate 218 and a noise filter plate 226 that is distinct from sensor-holding plate 218. In such applications, noise filter plate 226 is typically shaped to define a noise filter rim 228. Noise filter rim 228 is more rigid than central portion 221 of the sensor-holding plate, such as to reduce movement of the sensor-holding plate in response to motion of the second person, relative to if the noise filter rim were not more rigid than the central portion of the sensor-holding plate. Thus, noise filter rim 228 allows for mechanical filtering of signals coming from the partner, in a manner generally described hereinabove with respect to edges 142 of sensor plate 140 (FIG. 5). Alternatively or additionally, sensor-holding plate 218 may be shaped to define a rigid sensor-holding-plate rim 220 (which is more rigid than central portion 221), the function of which is generally similar to that of noise filter rim 228. Typically, a thickness t2 of the sensor-holding-plate rim, measured between an inner perimeter of the sensor-holding-plate rim and an outer perimeter of the sensor-holding-plate rim, is at least 2 mm and/or less than 8 mm, or alternatively, at least 8 mm and/or less than 20 mm.

In some applications, the top of noise filter rim 228 is generally level with the top of sensor-holding plate 218, while in other applications, the top of noise filter rim 228 is higher, e.g., it is greater than 1 and/or less than 5 mm higher. In some applications, a thickness t of noise filter rim 228, measured between an inner perimeter of the noise filter rim and an outer perimeter of the noise filter rim, is at least 2 mm and/or less than 8 mm, e.g., 5 mm.

Typically, sensor-holding plate 218 is shaped to hold sensor element 366, e.g., via a sensor receptacle 222, thus allowing for the sensor element to be coupled to the sensor plate. In some applications, the sensor-holding plate further comprises an electronics receptacle 224, configured to hold electronic circuitry which may include, for example, an amplifier, analog to digital converter, and/or a communication element. In other applications, the sensor-holding plate does not comprise electronics receptacle 224, and the circuitry is disposed outside of the sensor-holding plate.

In some applications, sensor-holding plate 218 is reversibly culpable to noise filter plate 226. The coupling may be effected, for example, by means of sensor-holding-plate rim 220, which is disposed along the perimeter of sensor-holding plate 218 and is configured to fit into a groove 230 disposed along the inside perimeter of noise filter plate 226. In some applications, a width of groove 230, measured in a direction from an outer perimeter of the groove toward an inner perimeter of the groove, is greater than 0.05 and/or less than 2 mm greater than thickness t2 of rim 220.

Figure 10A:
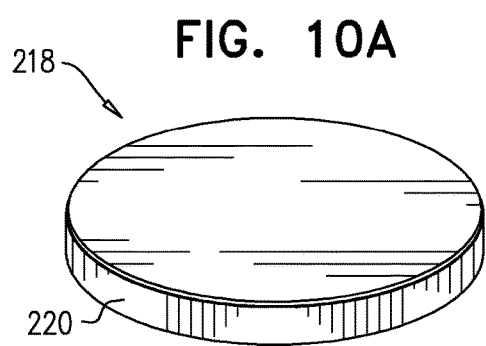
FIGS. 10A-D are schematic illustrations of a sensor-holding plate, in accordance with some applications of the present invention.

Reference is now made to FIGS. 10A-D, which are schematic illustrations of sensor-holding plate 218, in accordance with some applications of the present invention. FIG. 10A shows sensor-holding plate 218 with a continuous rim 220 which appears generally as shown in FIG. 9B. The inventors hypothesize that for some applications, continuous rim 220 facilitates generally isotropic focusing of motion sensor 30, in that continuous rim 220 is generally equally effective at blocking motion from all lateral directions.

Figure 10B:
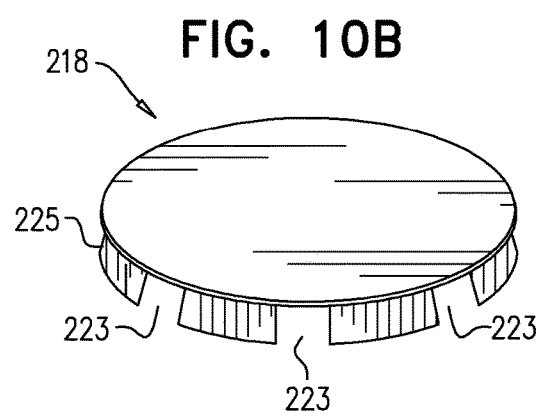

FIG. 10B shows sensor-holding plate 218 with a discontinuous rim 225, shaped to define a plurality of slots (i.e., openings, or gaps) 223 therein, disposed around rim 225. Slots 223 create a "defocusing" effect, i.e., they facilitate the sensing of motion from areas which are not directly above sensor-holding plate 218. By varying the location, number, and size of slots 223, sensor-holding plate 218 can be configured for different beds sizes.

Figure 10C:
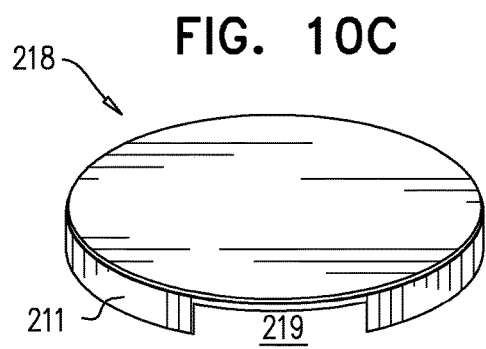

FIG. 10C shows sensor-holding plate 218 with a discontinuous rim 211, shaped to define one or more anisotropically-arranged slots 219 therein. Proper orientation of slots 219 may facilitate the sensing of motion originating from one or more particular areas not directly above sensor-holding plate 218. For example, the sensor-holding plate of FIG. 10C may be placed at the head of the bed, oriented such that slot 219 is directed toward the legs of the subject. In this manner, rim 211 will generally prevent the partner's motion from being sensed, while generally allowing the subject's motion to be sensed.

Although FIGS. 10B-C show the sensor-holding-plate rim shaped to define slots therein, the scope of the present invention includes rims which comprise thinned portions which function in a manner generally similar to slots 223 and 219.

Figure 10D:
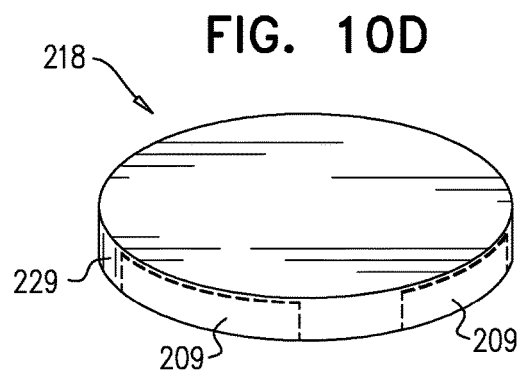

In some applications, as shown in FIG. 10D, the rim 229 of sensor-holding plate 218 may comprise one or more detachable parts 209. The detachment of parts 209 results in the opening of slots such as slots 223 and slots 219. Detachable parts 209 allow for reducing the manufacturing cost of sensor-holding plate 218, since the desired slots can generally be opened post-manufacture. For example, if the subject is sleeping alone and the bed is relatively large, the subject may decide to detach a plurality of small detachable parts 209 to create slots 223, as shown in FIG. 10B, such that motion of the subject is detected even when the subject is not directly over sensor-holding plate 218. In some applications, parts 209 which have been detached may subsequently be re-attached.

When anisotropically-arranged slots, e.g., slots 219, are used, sensor-holding plate 218 may need to be fixed in place, such that its orientation remains generally constant. For example, in the case in which sensor-holding plate FIG. 10C is to be placed under the head of the bed with a slot 219 directed towards the subject's legs, sensor-holding plate 218 may be fixed in place within the subject's pillow, which in general tends to be perpendicular to the subject's longitudinal axis.

In general, the various applications shown in FIGS. 10A-D may be practiced in combination with the applications shown in FIG. 9A-B. For example, the various rims that are shown in FIGS. 10A-D may be more rigid than central portion 221, as described hereinabove.

In some applications, as shown in FIGS. 9A-B, sensor-holding plate 218 is circular; a sensor-holding plate shaped in this manner has been found by the inventors to be generally effective in transmitting mechanical forces to the sensor coupled to the center thereof. In some applications, the sensor element coupled to sensor-holding plate 218, e.g., via sensor receptacle 222, is also circular. It has been found by the inventors that the ratio of sensor element diameter (which is generally similar to diameter D0 of sensor receptacle 222 shown in FIG. 9B) to sensor-holding plate diameter D1 is a relevant factor for effective transmission of mechanical forces to the sensor. In some applications of the present invention, the ratio of sensor element diameter to sensor-holding plate diameter D1 is greater than 0.1 and/or less than 0.6. In other applications, sensor-holding plate 218 is not circular, e.g., it may be square or another shape. In these applications, noise filter plate 226 is shaped accordingly, such that the noise filter is configured to be reversibly culpable to the sensor-holding plate as generally described with respect to FIGS. 9A-B, mutatis mutandis.

In some applications, sensor plate 238 is used in combination with subject identification module 102, described hereinabove with respect to FIG. 4. Although sensor plate 238 reduces the degree to which motion sensor 30 detects motion of the second person, it is possible that the sensor will nonetheless detect some of this motion. Subject identification module 102 therefore identifies components of the motion signal from sensor 30 that were generated by the subject, by distinguishing between components of the motion signal that were generated respectively by the subject and by the second person, e.g., as described hereinabove. In other applications, subject identification module 102 is used without sensor plate 238.

Figure 31:
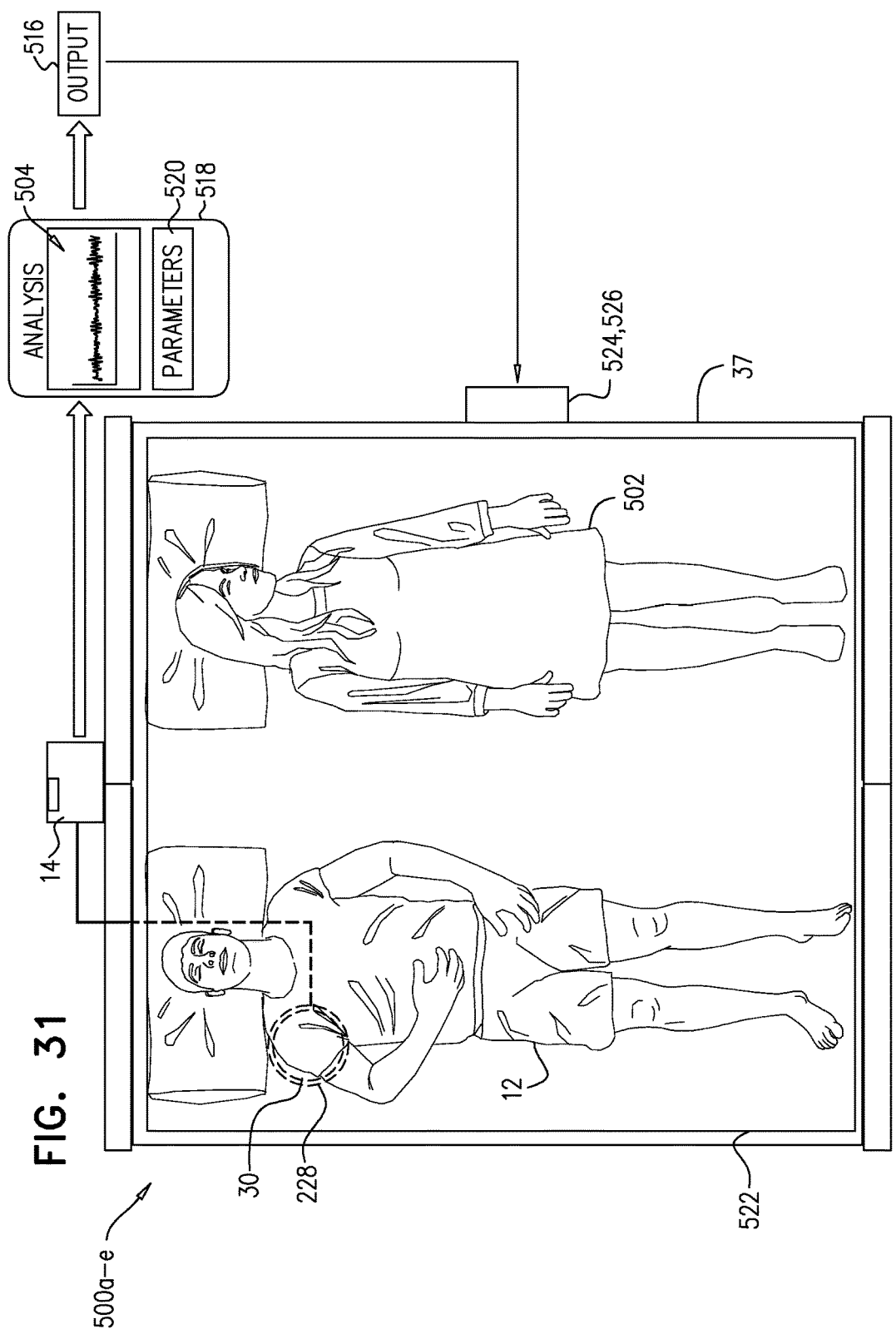
FIG. 31 is a schematic illustration of various apparatus for use with a subject who shares a bed with a second person, in accordance with some applications of the present invention.

Reference is now made to FIG. 31, which is a schematic illustration of various apparatus 500a-e for use with a subject 12 who shares a bed with a second person 502, in accordance with some applications of the present invention. In all of apparatus 500a-e, motion sensor 30 detects motion of subject 12 and motion of second person 502, and generates a motion signal 504 in response thereto. (Motion sensor 30 is typically a single motion sensor that does not contact or view the subject, clothes the subject is wearing, the second person, or clothes the second person is wearing.) Furthermore, another common element in apparatus 500a-e is that control unit 14 (e.g., via subject identification module 102 (FIG. 4)) distinguishes between motion of the subject and motion of the second person, i.e., it may identify a particular portion of motion signal 504 as coming from the subject or from the second person. On the other hand, apparatus 500a-e differ from each other in the technique(s) used to perform the distinguishing/subject-identification, in the analysis that is performed pursuant to the distinguishing/subject-identification, and/or in the output that is generated.

In apparatus 500a, control unit 14 is configured to identify that a portion of the motion signal was generated in response to motion of the second person, and not in response to motion of the subject, by identifying that the portion exhibits ringing. Reference is made to FIG. 32, which is a plot of motion signal 504 that includes a portion 506 thereof that exhibits ringing, as analyzed in accordance with some applications of the present invention. Motion signal 504 includes portions 501a and 501b that, respectively, precede and follow portion 506. Portions 501a and 501b exhibit a generally regular, cyclical pattern that is typically indicative of the cardiac and respiratory motion of the subject. Portion 506, on the other hand, has more of a step-response profile, which is typically indicative of large body-movement. The ringing in portion 506 indicates that the source of the large body-movement is the second person, who is not directly above the sensor.

To identify the ringing, control unit 14 ascertains that portion 506 includes a set of at least three consecutive extrema 508 (i.e., three consecutive maxima, or three consecutive minima), each of which (following the first extremum of the set) is separated from the preceding extremum of the set by a time TO that falls within a given time range (e.g., 0.15-0.45 seconds). (In FIG. 32, two such sets of consecutive extrema are shown.) Typically, to identify the ringing, control unit 14 further ascertains that respective differences between (i) magnitudes of consecutive extrema 508, and (ii) a magnitude of an extremum 510 that precedes the set of consecutive extrema (typically an initial "spike" that precedes the set), fall within a given amplitude range. For example, the control unit may identify that the respective differences are between 10%-150% of the magnitude of extremum 510. Typically, the control unit further ascertains that a difference between (i) a smallest magnitude 512 of the consecutive extrema, and (ii) a largest magnitude 514 of the consecutive extrema, is less than a threshold (e.g., 30% of smallest magnitude 512).

Figure 32:
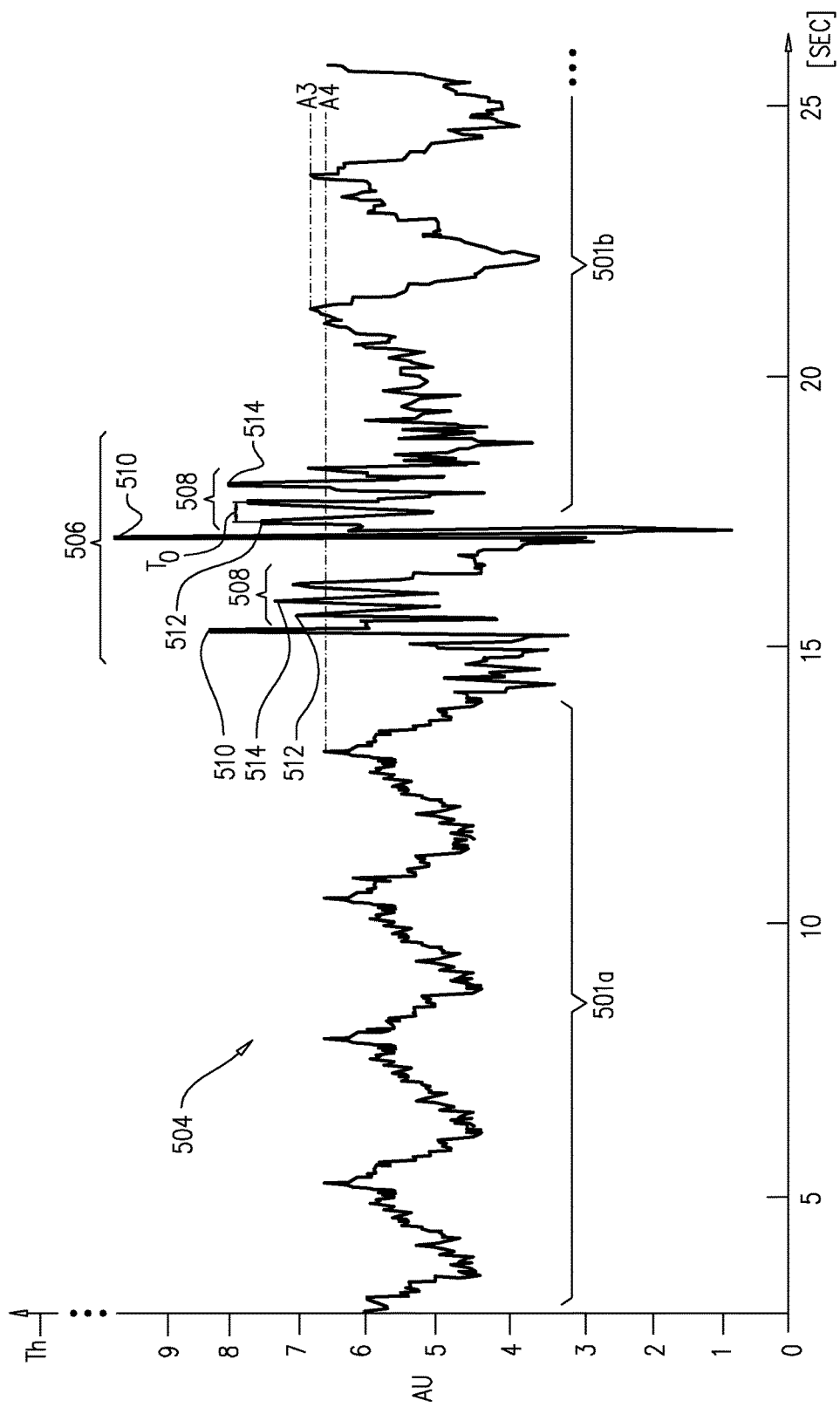
FIG. 32 is a plot of a motion signal that includes a portion thereof that exhibits ringing, as analyzed in accordance with some applications of the present invention.

Although FIG. 32 shows the ringing phenomenon only for large body-movement, ringing may also be exhibited in portions of signal 504 that reflect other types of motion, such as respiratory motion or cardiac motion. Apparatus 500a is configured to identify the second person as the source of these other types of motion, by performing the ringing-identification techniques described hereinabove.

Apparatus 500b uses a different technique to identify that a given portion of the motion signal was generated in response to large body-movement of the second person, and not in response to motion of the subject. In apparatus 500b, control unit 14 is configured to "learn" an amplitude threshold Th by analyzing a portion of the motion signal (e.g., portion 501a) that was generated in response to motion (e.g., cardiac and/or respiratory motion) of the subject, and calculating threshold Th based on the analysis. (For example, Th may be a multiple of amplitude A4 of portion 501a.) If the amplitude of a given portion of the motion signal is less than the amplitude threshold, the control unit identifies that the given portion of the motion signal was generated in response to large body-movement of the second person, and not in response to motion of the subject. For example, in FIG. 32, extremum 510 is less than Th, such that portion 506 is determined to have been generated by large body-movement of the second person.

Apparatus 500c uses yet another technique for distinguishing between motion of the subject and motion of the second person. In apparatus 500c, control unit 14 identifies a subject-motion component of the motion signal that was generated in response to motion of the subject, e.g., portions 501a and 501b of FIG. 32. To identify whether a given portion, e.g., portion 506, of the motion signal was generated in response to large body-movement of the subject, and not in response to motion of the second person, control unit 14 compares the amplitude A3 of the subject-motion component following the given portion, relative to the amplitude A4 before the given portion. If the amplitude has changed by a threshold amount, it is likely the subject moved relative to the sensor, and thus, the large body-movement is likely that of the subject. (FIG. 32 shows A4 being different from A3, but not by more than the threshold amount, such that portion 506 is determined to have been generated by motion of the second person.)

In general, the distinguishing/subject-identification techniques of apparatus 500a-c are typically combined, i.e., the control unit is typically configured to use any of the techniques described hereinabove, separately or in combination.

Apparatus 500d also comprises motion sensor 30 and control unit 14, and also distinguishes between motion of the subject and motion of the second person, e.g., using some or all of the techniques of apparatus 500a-c. In apparatus 500d, control unit 14 is configured to, by analyzing the signal from motion sensor 30 in an analysis step 518, identify an effect of large body-movement of the second person on sleep of the subject, and in response thereto, generate a sleep-disturbance output 516. Output 516 may include a report (e.g., a digital, and/or printed, and/or audio report), which may include alphanumeric and/or graphical content. Alternatively or additionally, as further described hereinbelow, output 516 may include a recommendation to change a parameter, and/or instructions to a device to change a parameter. In general, output 516 facilitates the reduction of the extent to which movement by second person 502 disturbs the sleep of subject 12.

In some applications, output 516 includes an assessment of an effectiveness of a parameter at reducing the effect of the large body-movement of the second person on the sleep of the subject. For example, the control unit may assess one or more parameters 520 such as:

(a) a parameter (e.g., a firmness, or a width) of a mattress 522 on which the subject is sleeping, (b) a parameter (e.g., a tilt angle) of bed 37, (c) a sleeping arrangement of (e.g., a distance between) the subject and the second person, and/or (d) a room-environment parameter (e.g., a level of light or sound, or a temperature, in the room).

Some of parameter types (a)-(d) (e.g., a level of light in the room) may be detected by control unit 14, while other parameter types (e.g., a firmness of mattress 522) are typically received as manual inputs to the control unit.

Typically, in analysis step 518, the control unit analyzes motion signal 504 in light of the parameter(s), and generates the assessment in response to the analysis. For example, the control unit may compare data from several nights of sleep, and/or compare the data from the given pair of sleepers with data from other pairs of sleepers, to ascertain how the parameter(s) affect the level of sleep disturbance. Output 516 may include, for example, an assessment message such as "A temperature between 23-25 C in the room is more effective at reducing sleep disturbance, relative to other temperatures." Alternatively or additionally, output 516 may include a recommendation to reduce the effect of the large body-movement of the second person on the sleep of the subject, by adjusting an adjustable parameter such as any of parameters (a)-(d) listed above. For example, output 516 may include a recommendation message such as "To reduce sleep disturbance, you may wish to reduce the tilt angle of your bed."

In some applications, apparatus 500d is used (e.g., by a mattress provider or consumer) to compare between different types of mattresses. For example, output 516 may include a comparison between (a) the effectiveness of a parameter of one given type of mattress, and (b) the effectiveness of the parameter of a different type of mattress. For example, output 516 may show a consumer that a firmer mattress is more effective than a less-firm mattress at reducing sleep disturbance, and based on this comparison, the consumer may decide to purchase the firmer mattress.

In some applications, output 516 includes instructions to a device 524 to adjust an adjustable parameter, e.g., any of (a)-(d) listed above. For example, FIG. 31 shows output 516 including instructions to a controller 526 to adjust a tilt angle of bed 37.

Apparatus 500e also comprises motion sensor 30 and control unit 14, and also distinguishes between motion of the subject and motion of the second person, e.g., using some or all of the techniques of apparatus 500a-c. In apparatus 500e, motion sensor 30 comprises a mechanical-filtering element, such as noise filter rim 228 (described hereinabove with reference to FIGS. 9A-B), which is configured to reduce a response of the motion sensor to motion of the second person, relative to motion of the subject. Control unit 14 analyzes motion signal 504, assesses an effectiveness of the mechanical-filtering element at reducing the response of the motion sensor to motion of the second person, and generates an output in response thereto. For example, if control unit 14 identifies a relatively large number of portions of the signal coming from motion of the second person, control unit 14 may make an assessment that the mechanical-filtering element is relatively ineffective. In such a case, output 516 may include, for example, a recommendation to replace the current noise filter rim with a thicker noise filter rim.

It is noted that there is a "philosophical" difference between apparatus 500d and apparatus 500e, in that a typical objective in using apparatus 500e is to improve the filtering out of motion from the second person (perhaps to the point of near-complete filtering), whereas apparatus 500d requires that sensor 30 detect at least some of the motion from the second person. Nevertheless, apparatus 500d and 500e may be combined, such that a single control unit 14 is configured to perform both the functions of apparatus 500d and the functions of apparatus 500e.

Figure 15:
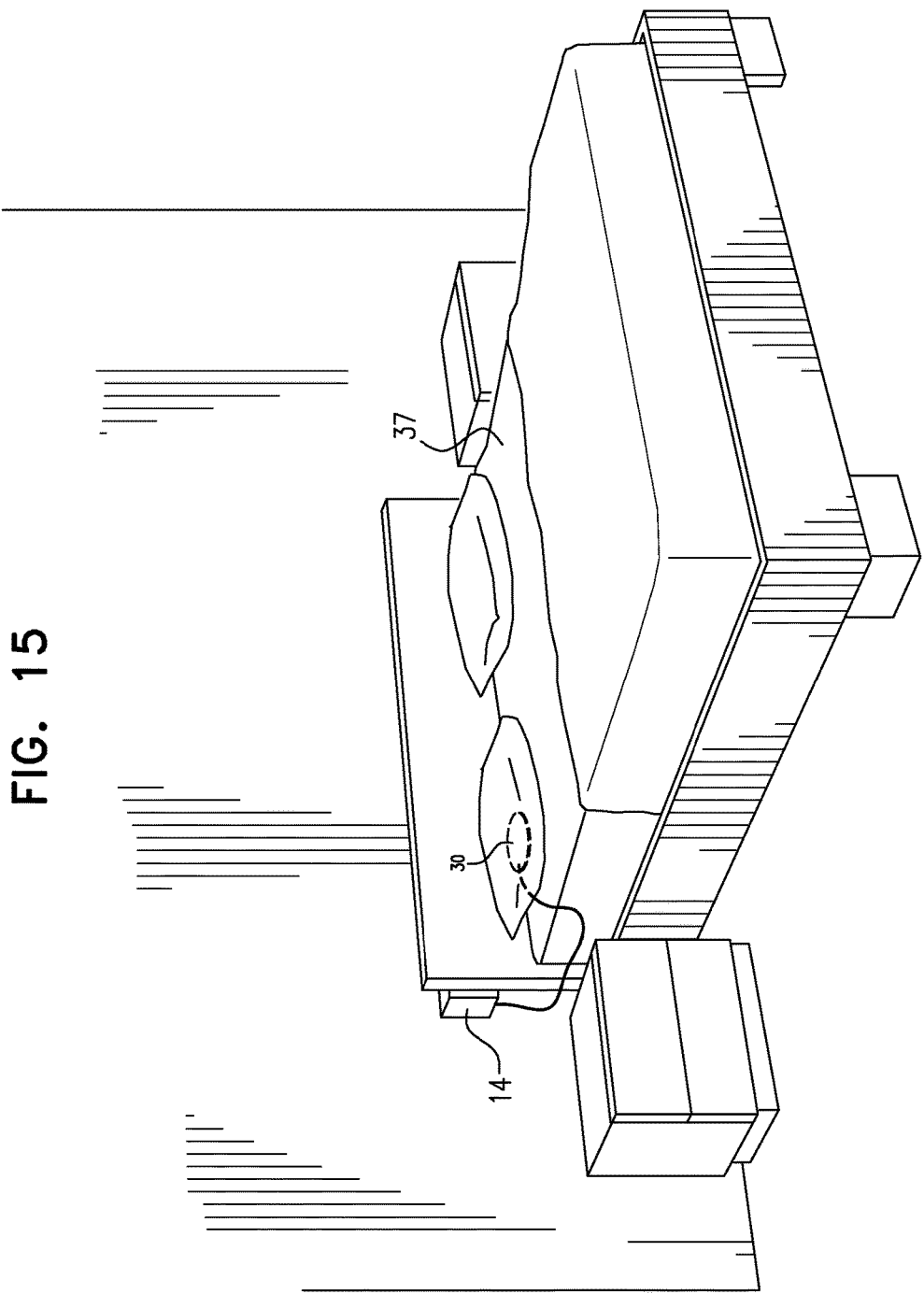
FIG. 15 is a schematic illustration of a sensor configured to be placed within a pillow, in accordance with some applications of the present invention.

Reference is now made to FIG. 15, which is a schematic illustration of a sensor 30 configured to be placed within a pillow 301, in accordance with some applications of the present invention. In some applications, motion sensor 30 is configured to be placed within pillow 301 of subject 12.

Reference is now made to FIG. 11, which is a schematic illustration of apparatus comprising a motion sensor 30, control unit 14, and speaker 232, in accordance with some applications of the present invention. In some applications of the present invention, motion sensor 30 and a speaker 232 are configured to be placed under the head of a subject who shares a bed with another person. (Thus, FIG. 11 depicts resting surface 37 as a double bed.) For example, sensor 30 may be placed within the pillow of the subject. Speaker 232 is configured to play music responsively to output from control unit 14, for example, in order to help the subject fall asleep or use biofeedback techniques to relax. In some applications, sensor plate 238, described hereinabove with respect to FIGS. 9A-B, is used. The use of sensor plate 238, which, as explained above, comprises a more rigid edge region 227 (FIG. 9B), provides that speaker 232 responds largely to the sleep stage and physiological condition of the subject, rather than also to motion from the other person. In some applications, control unit 14 may eliminate artifacts generated by speaker 232 by subtracting the signal generated by the speaker from the motion signal. The signal generated by speaker 232 may be received, for example, from the speaker controlling circuit or from another sensor on the speaker.

Figure 14:
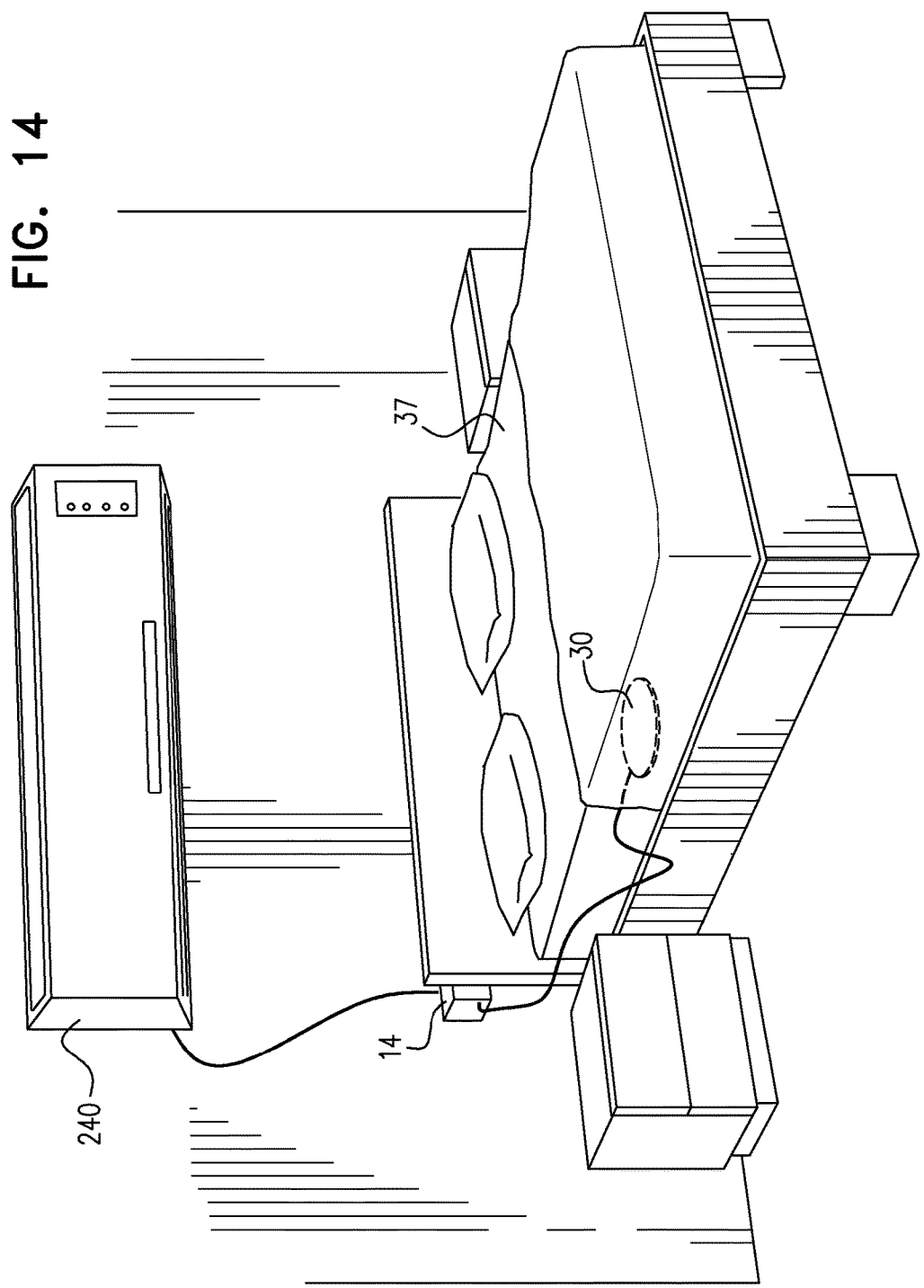
FIG. 14 is a schematic illustration of apparatus for controlling a thermoregulation device, in accordance with some applications of the present invention.

Reference is now made to FIG. 14, which is a schematic illustration of apparatus for controlling a thermoregulation device 240, in accordance with some applications of the present invention. Studies show that dynamically regulating the temperature of a subject's sleep environment may improve the subject's sleep quality. For example, maintaining a steady temperature may increase the deep sleep (SWS) ratio, and cooling the bed during REM may increase the REM sleep share rate. In some applications, control unit 14 is connected to a thermoregulation device 240 located, for example, in the subject's bed or elsewhere in the subject's bedroom. Control unit 14 monitors the subject's sleep stages and controls thermoregulation device 240 accordingly. Examples of thermoregulation devices which may be configured to be controlled by control unit 14 include air-conditioning units, electric heaters, radiators, bed coolers, and electric blankets.

Figure 12:
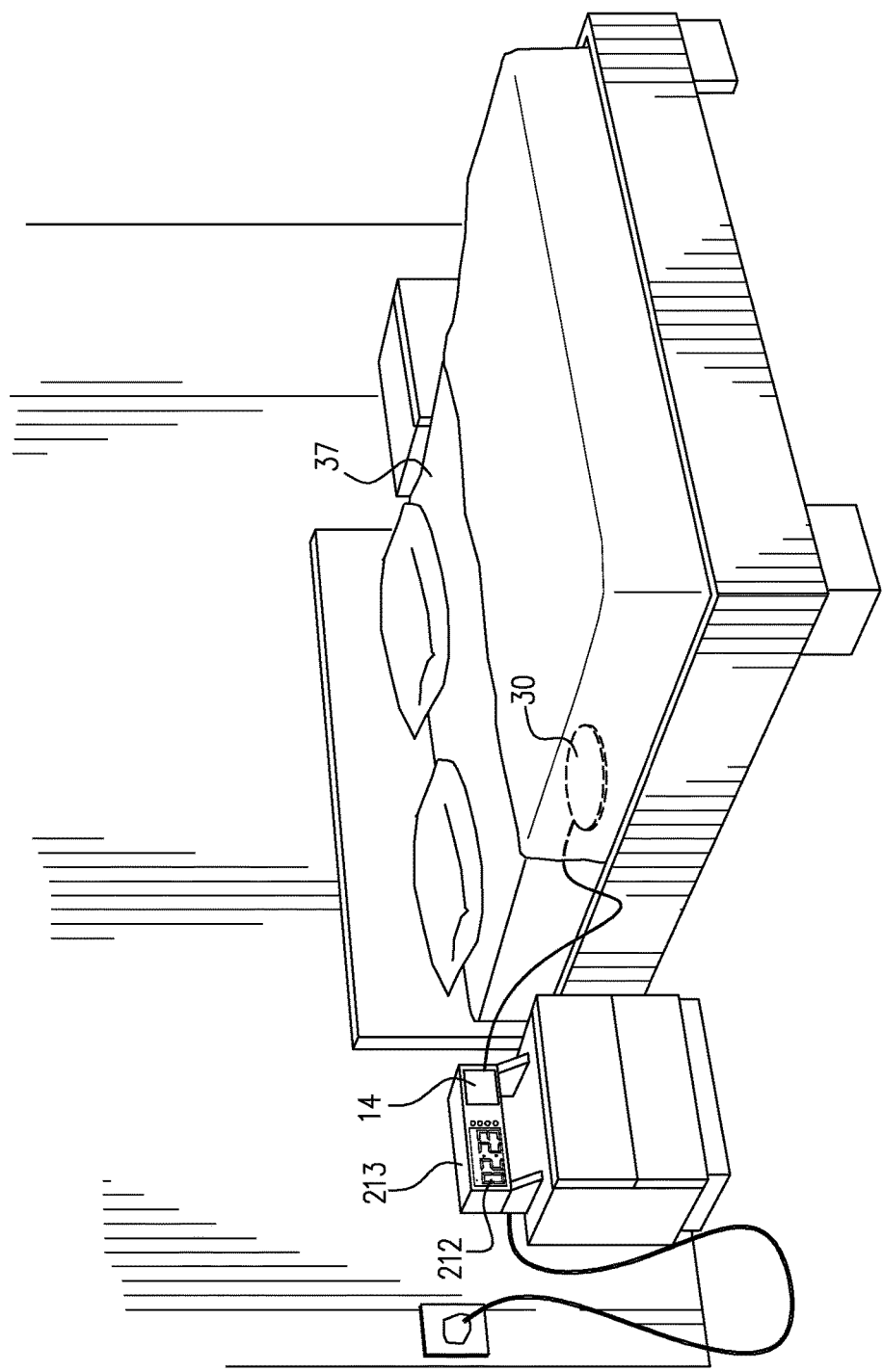
FIG. 12 is a schematic illustration of apparatus comprising a motion sensor, control unit, and alarm clock, in accordance with some applications of the present invention.

Reference is now made to FIG. 12, which is a schematic illustration of apparatus comprising a motion sensor 30, control unit 14, and alarm clock 212, in accordance with some applications of the present invention. For some applications, an alarm clock 212 is configured to receive an output from control unit 14. The output is generated in response to a signal from motion sensor 30, and indicates whether a resting surface 37, e.g., a bed, is occupied by a subject. In response to the output indicating that resting surface 37 is unoccupied, alarm clock 212 inhibits itself from sounding. This reduces the likelihood of an alarm waking other members of the household, in cases where the subject arose from resting surface 37 without taking measures to ensure that the alarm would not subsequently begin or continue to sound. In some applications, as shown in FIG. 12, alarm clock 212 and control unit 14 are integrated into a common unit 213. In other applications, alarm clock 212 is separate from control unit 14, and communicates therewith by wired or wireless communication means.

In some cases, the individual might arise from bed at the sounding of an alarm, but return to bed thereafter. Alternatively, the individual might not arise from bed, even though the alarm has sounded. In some applications, alarm clock 212 is configured to sound after a delay, in response to the output from control unit 14 indicating that the bed is occupied following a previous sounding of the alarm clock.

Figure 13:
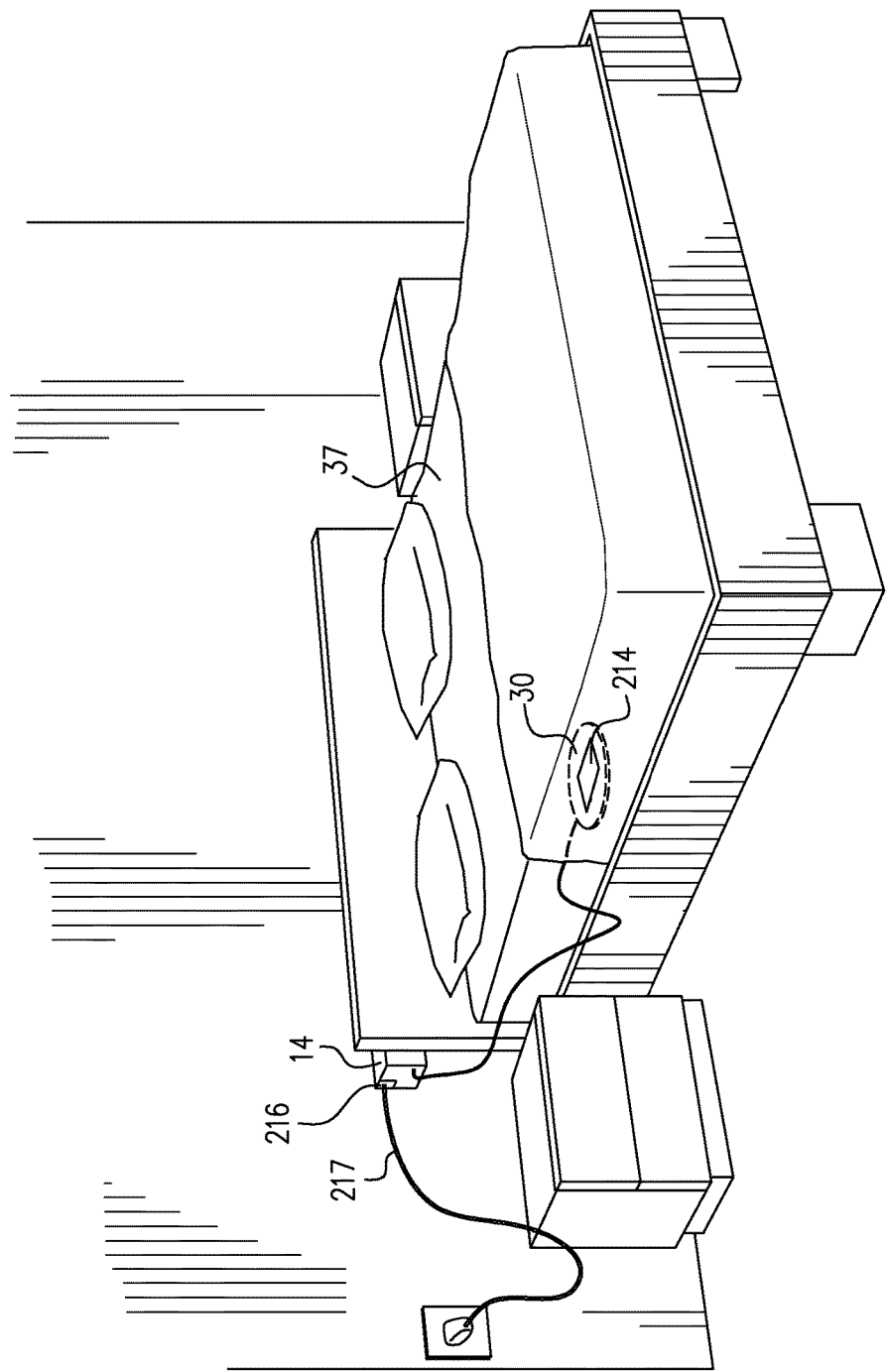
FIG. 13 is a schematic illustration of a motion sensor powered by a power supply and rechargeable battery, in accordance with some applications of the present invention.

Reference is now made to FIG. 13, which is a schematic illustration of a motion sensor 30 powered by an external power supply 216 (i.e., a power supply that is external to the motion sensor), and a rechargeable battery 214, in accordance with some applications of the present invention. In some applications, motion sensor 30 may be powered by an external power supply 216, which draws current via a power cord 217 connected to a wall outlet. Since some subjects are uncomfortable with power being drawn from the wall and conveyed to a device which is underneath them, motion sensor 30 is configured to not draw power from power supply 216, in response to output from control unit 14 indicating that resting surface 37 is occupied by the subject. In some applications, sensor 30 is configured to draw power from a rechargeable battery 214, in response to the output indicating that resting surface 37 is occupied. Rechargeable battery 214 is configured to draw power from a power supply, e.g., power supply 216, in response to the output from the control unit indicating that the resting surface is unoccupied, and to not draw power from the power supply, in response to the output indicating that the resting surface is occupied.

In some applications, system 10 is configured to analyze sleep patterns of a subject and, in response thereto, produce a sleep report which can be used, for example, for clinical sleep-study purposes.

In some applications, system 10 is configured to monitor subjects who are generally healthy, in order to help the subjects maintain or improve their state of well-being. For example, system 10 may be configured to help a healthy subject avoid unhealthful conditions or improve sleep quality.

In some applications, system 10 is configured to be used in combination with home-based appliances. For example, system 10 may be configured to transmit a signal to a coffee-maker, the signal indicating that the subject has woken up and/or has left the bed and might soon wish to drink a cup of coffee.

In some applications, a resting surface, e.g., a mattress, is configured to be used with motion sensor 30, such that motion sensor 30 may be disposed within the mattress. For example, the mattress may have an opening at its side configured to receive motion sensor 30, as well as a receptacle contained within the mattress configured to hold the sensor. Configuring a mattress in this manner allows for the sensor to be disposed closer to the subject, relative to applications in which the sensor is disposed underneath the mattress.

In some applications, control unit 14 is configured to receive mattress-related parameters such as thickness and resilience, and to analyze the signal from motion sensor 30 in light of the parameters. The mattress-related parameters may facilitate the quantification of signal amplitude on more of an absolute scale, thus facilitating a more effective response to the signal. For example, if the signal from sensor 30 indicates a weak heartbeat, but the mattress is relatively thick and resilient, control unit 14 may withhold the output unit from generating an alert.

Figure 16:
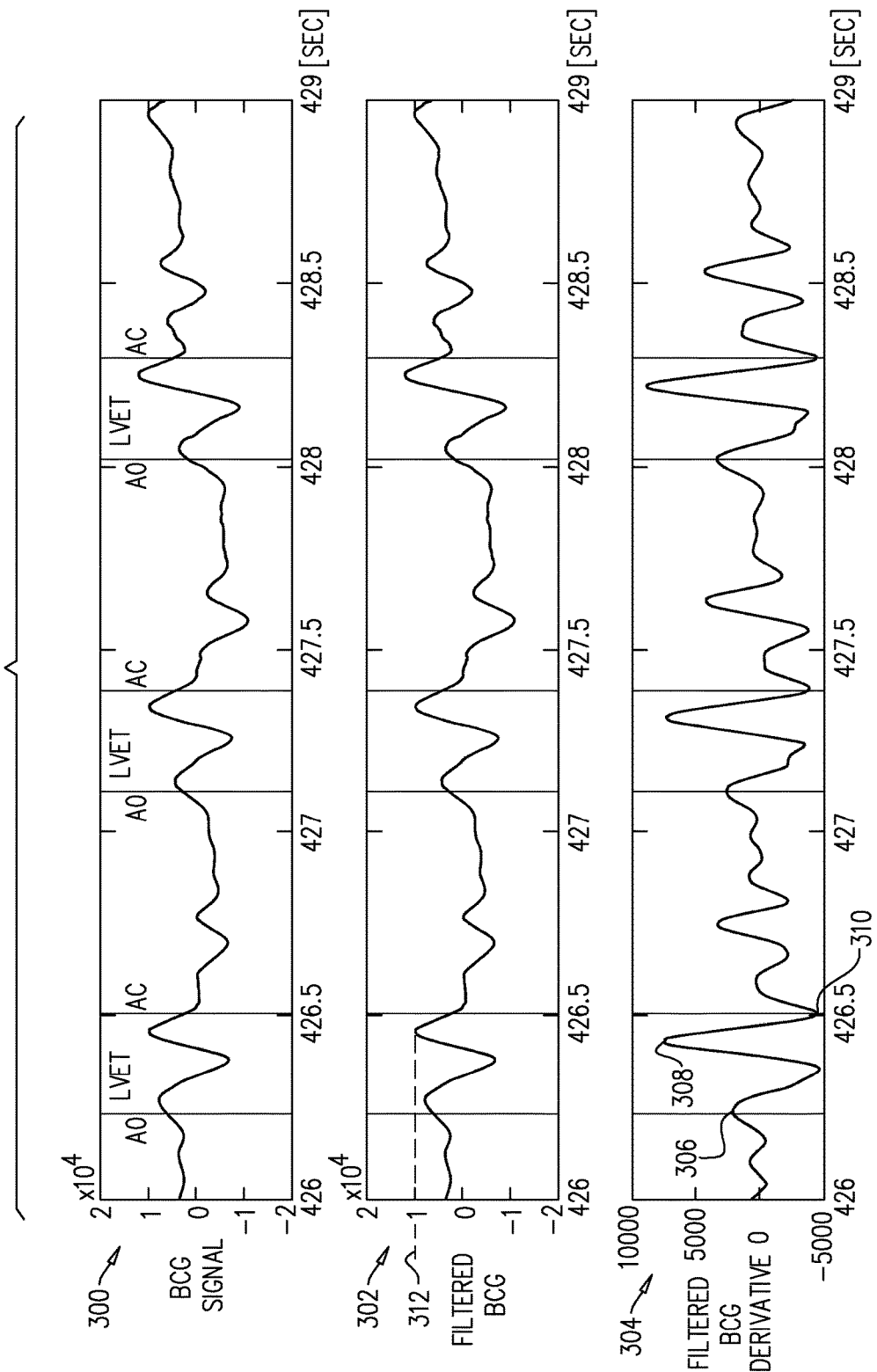
FIG. 16 is a schematic illustration of ballistocardiographic signals used for calculating an indication of a left-ventricular-ejection-time, in accordance with some applications of the present invention.

Reference is made to FIGS. 1, 2, 4, and 16. In some applications, control unit 14 (e.g., via heartbeat pattern analysis module 23) is further configured to calculate an indication of a left-ventricle-ejection-time (LVET) of subject 12. LVET is the time from the opening of the aortic valve during a heartbeat to the closing of the aortic valve during the heartbeat. A decrease in LVET may be indicative of a clinical condition, such as hypovolemia and/or hemorrhaging, that requires immediate medical attention. Reference is made to FIG. 16, which is a schematic illustration of ballistocardiographic (BCG) signals 300, 302, and 304 (in arbitrary units) used for calculating the indication of the LVET, in accordance with some applications of the present invention. Signal 300 is a heartbeat-related signal that is extracted by heartbeat pattern analysis module 23 from the raw motion signal generated by sensor 30. Signal 300 is typically extracted by means of spectral filtering in the range of about 0.8 to about 5.0 Hz, as described hereinabove. (A matched filter may be used to extract signal 302.) Signal 300 is typically smoothed by a low-pass filter to yield signal 302. (In FIG. 16, signal 300 is generally smooth, such that signal 302 appears substantially identical to signal 300.) The derivative of signal 302 is calculated by module 23, after which the derivative is typically smoothed with a low-pass filter, yielding signal 304. Each of signals 300, 302, and 304 is marked in FIG. 16 to show an indication of aortic valve openings (AO) and closings (AC). As described above, the time between these events is the LVET of the subject.

Heartbeat pattern analysis module 23 is configured to calculate an indication of the LVET by analyzing signal 304. (In some applications, the unsmoothed derivative of signal 302, instead of signal 304, is analyzed.) For example, heartbeat pattern analysis module 23 may be configured to identify the most prominent positive peaks 308 in signal 304. Following the identification of peaks 308, module 23 identifies the positive peaks 306 that immediately precede peaks 308, which correspond to AO, and the negative peaks 310 that immediately follow peaks 308, which correspond to AC. As appropriate, techniques described in Alametsa et al, "Ballistocardiogaphic studies with acceleration and electromechanical film sensors", Medical Engineering & Physics, 2009, which is incorporated herein by reference, may be applied to calculating the LVET. The time between peaks 306 and 310, and/or another indication of the LVET, is then calculated by module 23, and control unit 14 drives an output device, e.g., user interface (U/I) 24, to generate an output, such as an audio and/or visual output, in response to the calculated indication. Typically, calculating the indication involves averaging one or more parameters, such as the time between peaks 306 and 310, over several heartbeats.

In some applications, control unit 14 (e.g., via module 23) is further configured to identify a risk of hypovolemia of the subject, in response to the calculated indication of the LVET. For example, module 23 may determine that the LVET has decreased, relative to previously-calculated LVETs and/or to a subject-baseline LVET or a population-baseline LVET, such that the subject is at risk of hypovolemia. For example, the subject may be experiencing hypovolemia and/or hemorrhaging. Control unit 14 drives U/I 24 to generate the output in response to the identified risk of hypovolemia. Typically, the generated output includes an alert to a physician or other caregiver.

In some applications, control unit 14 (e.g., via module 23) is further configured to identify a change in stroke volume of subject 12. Typically, this is done by using the amplitude 312 of heartbeat signal 302 as an indication of the subject's stroke volume, as amplitude 312 is typically positively correlated to stroke volume. Typically, while amplitude 312 is being monitored by module 23, raw signal 300 is also being processed by system 10 to identify any posture changes of the subject. For example, the system may identify a posture change using techniques as described in US 2011/0112442 to Meger, which is incorporated herein by reference. If no posture change has been identified, a change in amplitude 312 is likely indicative of a change in stroke volume, since the change in amplitude cannot be attributed to a posture change of the subject. Control unit 14 drives the output device (e.g., U/I 24) to generate an output, in response to the identified change in stroke volume.

In some applications, the control unit is further configured to identify a risk of hypovolemia of the subject, in response to the identified change in stroke volume. For example, the control unit may identify a risk of hypovolemia (e.g., of hemorrhaging), in response to the stroke volume dropping below a specified absolute or percentage threshold. Control unit 14 drives U/I 24 to generate the output in response to the identified risk of hypovolemia. Typically, the generated output will include an alert to a physician or other caregiver. In some applications, the risk of hypovolemia is identified in response to both the change in stroke volume and a change in LVET. For example, a slight decrease in stroke volume may be cause for alarm only if it is accompanied by a decrease in LVET.

Figure 17:
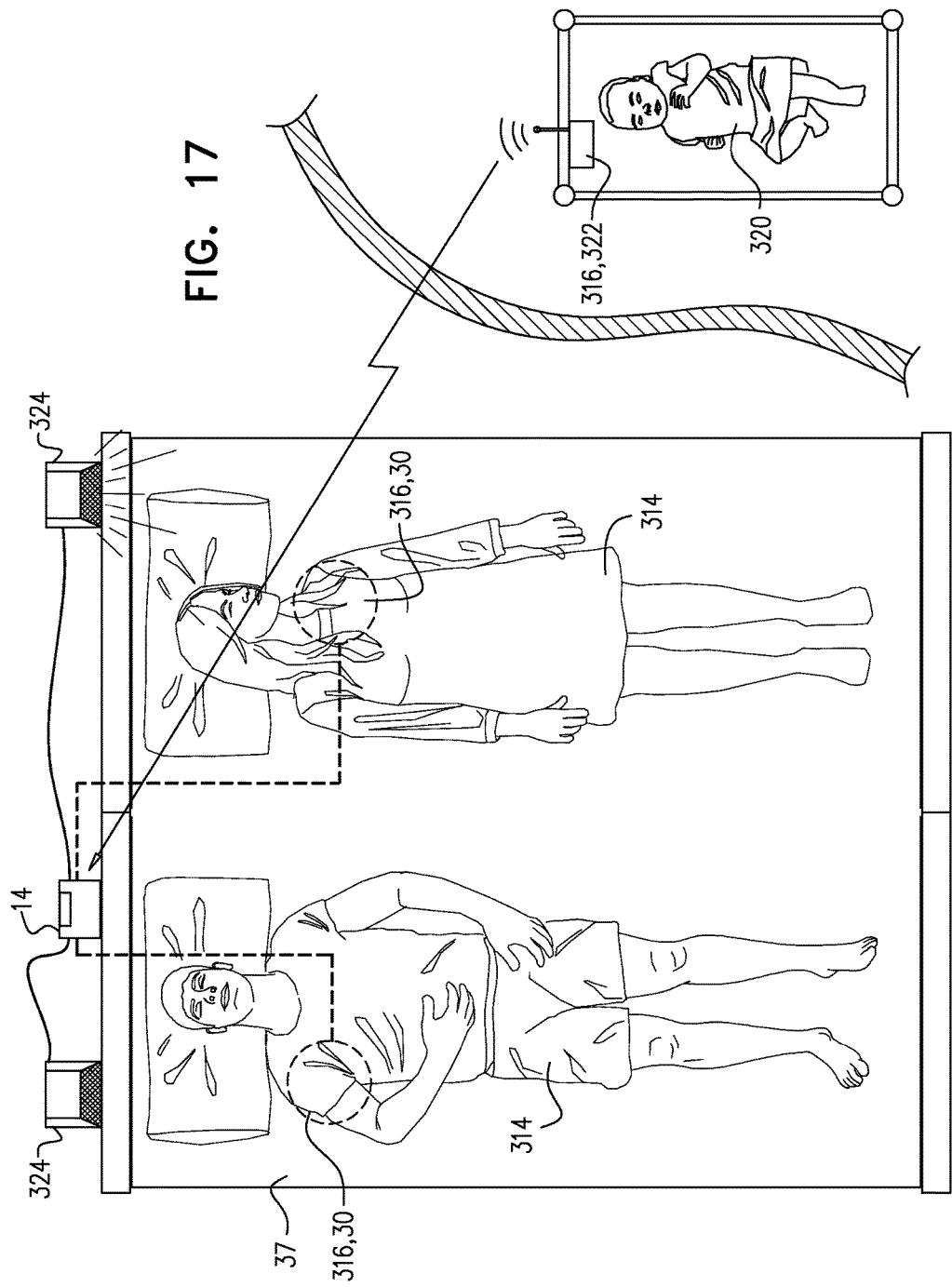
FIG. 17 is a schematic illustration of apparatus for use with a plurality of sleeping subjects, in accordance with some applications of the present invention.

Reference is now made to FIG. 17, which is a schematic illustration of apparatus for use with a plurality of sleeping subjects 314, in accordance with some applications of the present invention. The apparatus comprises at least one sensor 316 (e.g., at least two sensors 316, e.g., exactly two sensors 316) configured to monitor each of subjects 314 while the subjects sleep. For example, as shown in FIG. 17, sensors 316 may comprise non-contact motion sensors 30, configured to sense motion of the subjects while the subjects sleep. (Typically, to help reduce contamination of the motion signal by motion of the other subject, each sensor 30 is placed underneath the outer shoulder of the subject being sensed.) Alternatively or additionally, sensors 316 may comprise at least one sensor of another type, such as an electromyographic sensor and/or an imaging sensor. In response to the monitoring, sensors 316 generate a respective signal for each of the subjects. Control unit 14 is configured to analyze the signals, and, based on the analyzing, identify at least one sleep-related parameter for each of the subjects. For example, for each of the subjects, the control unit may be configured to identify one or more of the following parameters:

(i) A length of time for which the subject has been sleeping, e.g., a length of time for which the subject has been in a deep sleep;

(ii) A number of prior awakenings of the subject, e.g., a number of prior awakenings during the present sleeping period and/or during a previous sleeping period;

(iii) A stage of a sleep cycle of the subject.

In identifying the sleep-related parameter(s), as well as generally, in identifying that a person is sleeping and/or in identifying a sleep stage of the person (e.g., as described below with reference to numerous figures), the control unit may use one or more of the techniques described in (a) US 2007/0118054 to Pinhas (now abandoned), (b) Shinar et al., Computers in Cardiology 2001; Vol. 28: 593-596, and (c) Shinar Z et al., "Identification of arousals using heart rate beat-to-beat variability," Sleep 21(3 Suppl):294 (1998), each of which is incorporated herein by reference.

At least in response to the identified sleep-related parameters, and typically further in response to receiving an input from a second sensor 318, control unit 14 identifies at least one of the subjects for wakening, and at least one of the subjects not for wakening. Typically, the apparatus further comprises a wakening device 324, and the control unit is configured to drive wakening device 324 to wake the subject(s) identified for wakening.

A typical situation in which the described apparatus may be used is shown in FIG. 17. Two parents 314 of a baby 320 are sleeping on a bed 37, while baby 320 sleeps in a different room. Second sensor 318 comprises, for example, an audio sensor 322, configured to communicate (e.g., wirelessly) a signal to control unit 14 in response to sounds made by baby 320. (In other applications, sensor 318 may comprise a different type of sensor, such as non-contact motion sensor 30 and/or an image sensor.) In response to receiving the input from sensor 318, the control unit identifies that baby 320 is crying, such that one of parents 314 should be wakened. Based on the sleep-related parameters, the control unit identifies the parent to be wakened. For example, if one parent is in a deep sleep while the other is not, the latter may be identified for wakening. Similarly, if one parent awoke in response to the previous crying episode, the other parent may be wakened in response to the current episode. In some applications, as shown in FIG. 17, wakening device 324 comprises a separate unit (e.g., a separate alarm-generating mechanism) for each of the sleeping subjects, such that one subject can be woken with minimal disturbance to the other. In other applications, wakening device 324 comprises a single unit. For example, in some applications, wakening device 324 may be integrated with U/I 24 (FIG. 2).

Although FIG. 17 shows two sensors 316, it is noted that the scope of the present invention includes the use of exactly one sensor 316 (e.g., exactly one motion sensor 30) to monitor both subjects 314. It is further noted that the apparatus described with reference to FIG. 17 may be used in combination with subject identification module 102 (FIG. 4), which helps differentiate between the motion of the first subject and the motion of the second subject, and/or in combination with one or more of the mechanical filtering applications described hereinabove. For example, sensor plate 140 with hardened edges 142 (FIG. 5), sensor plate 238 with rigid edge region 227 (FIG. 9A), etc. may be used in order to reduce contamination of one subject's motion signal by the other subject. Similarly, other "two-person" applications described hereinbelow with reference to FIGS. 18, 20, 21, and 22 may be practiced in combination with subject identification module 102 and/or one or more of the mechanical filtering applications described herein.

Other situations in which the described apparatus may be used include a situation in which a plurality (e.g., three or more) doctors or other caregivers are sleeping in a room, e.g., a resting room in a hospital. Sensor 318 senses a physiological parameter of a patient, and communicates the parameter to the control unit. In this situation, sensor 318 typically comprises a "dedicated" physiological sensor, such as an electrocardiograph, blood pressure monitor, etc., although sensor 318 may also comprise a sensor of the type described above, e.g., non-contact motion sensor 30. In response to the input from the sensor, the control unit determines that at least one, but not all, of the doctors should be woken, in order to tend to the patient. Based on the sleep-related parameters, as described above with respect to the parents of baby 320, the control unit identifies at least one of the doctors for wakening, and at least one of the doctors not for wakening. (In this situation, subjects 314 will typically be sleeping on multiple respective beds, and the apparatus may comprise more than one control unit, e.g., one control unit per bed, in communication with each other.)

In some applications, the control unit is further configured to generate a report that shows a history of the at least one sleep-related parameter for each of the subjects. The report may be generated at regular intervals, such as after every night. The generation of such a report may be helpful in avoiding conflicts. For example, in the parenting situation described above, the parent who was woken may feel less resentful if the report shows that despite been woken to tend to the crying baby, he/she slept better and/or longer overall, relative to the other parent.

Figure 18:
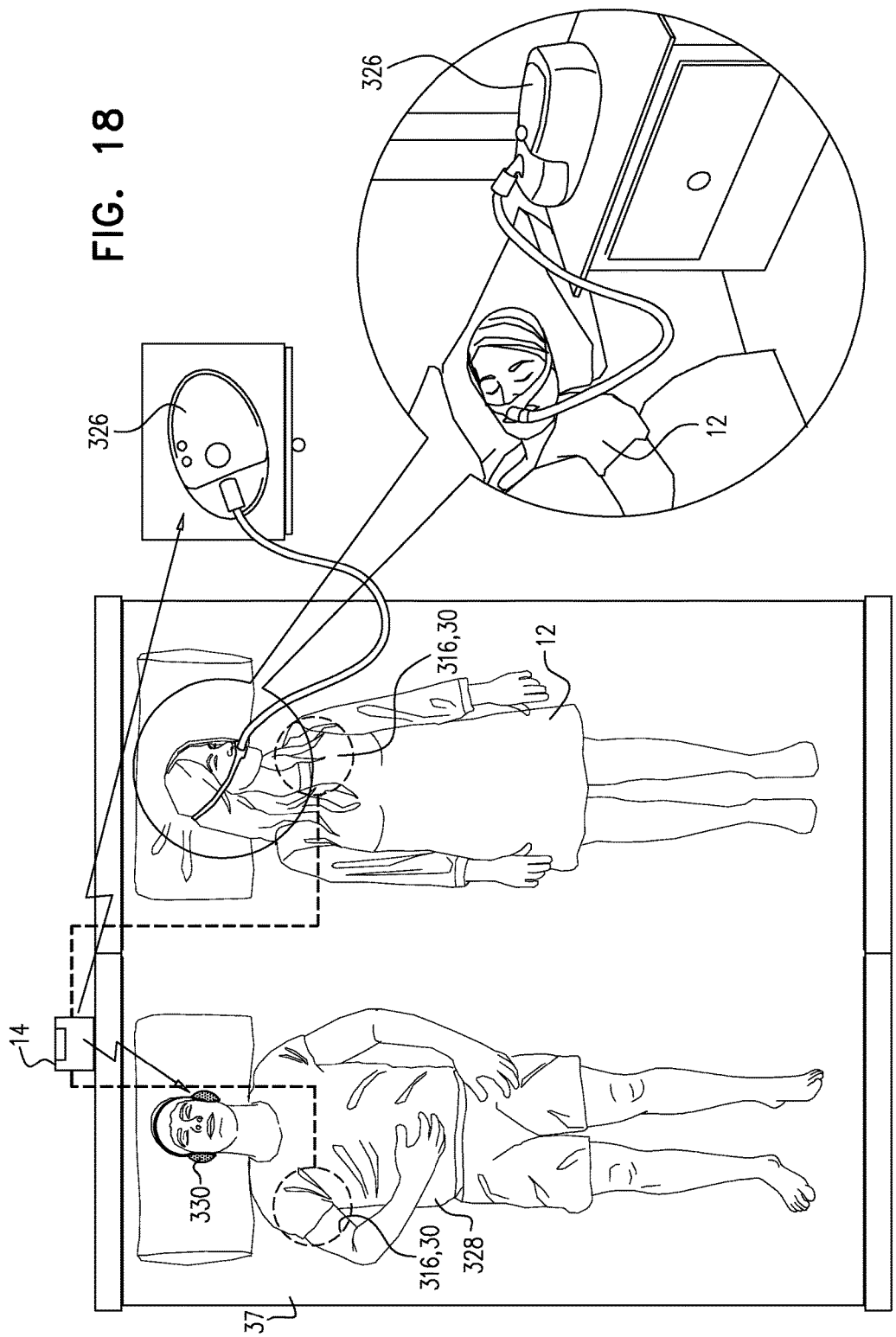
FIG. 18 is a schematic illustration of apparatus for activating a medical device for a subject who is sleeping in proximity to at least one other person, in accordance with some applications of the present invention.

Reference is now made to FIG. 18, which is a schematic illustration of apparatus for activating a medical device 326 (e.g., a continuous positive airway pressure (CPAP) device) for a subject 12 who is sleeping in proximity to at least one other person 328, in accordance with some applications of the present invention. The apparatus comprises at least one sensor 316 (e.g., at least two sensors 316, e.g., exactly two sensors 316) configured to monitor subject 12 and person 328. For example, as shown in FIG. 18, sensors 316 may comprise non-contact motion sensors 30, configured to sense motion of subject 12 and person 328 while they sleep. Alternatively or additionally, sensors 316 may comprise at least one sensor of another type, such as an electromyographic sensor and/or an imaging sensor. In response to the monitoring, sensors 316 generate a respective signal for each of subject 12 and person 328. Control unit 14 analyzes the signal for the subject, and, based on the analyzing, identifies at least one physiological parameter of the subject that relates to whether or not the device should be activated. For example, the control unit may identify a respiration-related parameter of subject 12 that is indicative of an occurring or expected episode of apnea, e.g., as described in US 2013/0281866 to Shinar, which is incorporated herein by reference. Alternatively or additionally, the control unit may identify a sleep-related parameter of subject 12 (e.g., how deeply the subject is sleeping) that relates to whether or not the device should be activated.

If subject 12 were sleeping alone, the identification of the physiological parameter might be sufficient cause to activate medical device 326. For example, if subject 12 were sleeping alone, the respiration-related parameter predictive of an apnea episode might be sufficient cause for the control unit to activate the CPAP device. However, given that subject 12 is not sleeping alone, the control unit also analyzes the signal for the other person, identifies at least one sleep-related parameter of the other person based on the analyzing, and activates the medical device further in response to the sleep-related parameter. For example, the sleep-related parameter may include a stage of sleep of the other person. If the other person is in a deep sleep, for example, the medical device may be activated, since the activation of the device is unlikely to disturb the other person. Conversely, if the other person is awake, the medical device may not be activated, since activation of the device may prevent the person from falling asleep. (If the other person is in a light sleep, the medical device may or may not be activated, depending on the application and possibly also on other factors, as further described immediately hereinbelow.) In some applications, the sleep-related parameter includes an indication of whether the other person is trying to fall asleep, and the control unit is configured to activate (or not activate) the medical device based on the indication. For example, if the parameter indicates that the other person is awake but is not trying to fall asleep (e.g. the other person is sitting in bed, and/or reading while lying in bed), the device may be activated. Conversely, if the parameter indicates that the other person is trying to fall asleep (e.g., the person is lying in a sleeping position) the device may not be activated. In some applications, an override feature is provided, whereby the medical device may be activated regardless of the sleep-related parameter of the other person.

In some applications, the control unit identifies one or more other factors, and in response to those factors, activates (or does not activate) the medical device. For example, in some applications, the control unit is further configured, based on the analyzing of the subject's signal, to identify a likelihood of an upcoming occurrence of a clinical episode of the subject. For example, the control unit may identify that there is high chance that the subject will soon experience an episode of apnea. In response to this likelihood, the control unit may activate the CPAP device, even if the other person is likely to be disturbed. In some applications, the control unit is further configured to, based on the analyzing of the subject's signal, identify an expected severity of the upcoming occurrence, and to activate (or not activate) the medical device in response to the expected severity. For example, if the predicted apnea episode is expected to be severe, the control unit may be configured to activate the medical device, even if the other person is likely to be disturbed.

In some applications, the control unit is configured to activate the medical device, further in response to an input that includes a history of awakenings of the subject and/or of the other person in response to previous activations of the medical device. For example, if the history shows that the other person is typically woken when the device is activated, the control unit may activate the device less readily, e.g., only if the other person is in a deep sleep. In some applications, the control unit is configured to track the history of awakenings of the subject and/or of the other person, thus allowing the control unit to learn the proper threshold to use when determining whether or not to activate the device. In some applications, the control unit is configured to activate the medical device, further in response to an input indicative of a sleep-disturbance tolerance of the subject, and/or an input indicative of a sleep-disturbance tolerance of the at least one other person. This input may be received, for example, via U/I 24 (FIG. 2). If the tolerance is low (i.e., if the input indicates that the subject and/or the other person is a light sleeper), the control unit will activate the device less readily.

In some applications, as shown in FIG. 18, the control unit is further configured to activate a noise-cancellation device 330 (e.g., noise-canceling headphones) for the at least one other person, upon activating the medical device. For example, if the control unit has determined that the medical device should be activated, but the other person is likely to be disturbed by the activation of the device, the control unit may activate the medical device while also activating noise-cancelation device 330.

Although FIG. 18 shows two sensors 316, it is noted that the scope of the present invention includes the use of exactly one sensor 316 (e.g., exactly one motion sensor 30) to monitor both subject 12 and other person 328. In such applications, subject identification module 102 (FIG. 4) may be used to differentiate between the motion of the subject and the motion of the other person.

Figure 19:
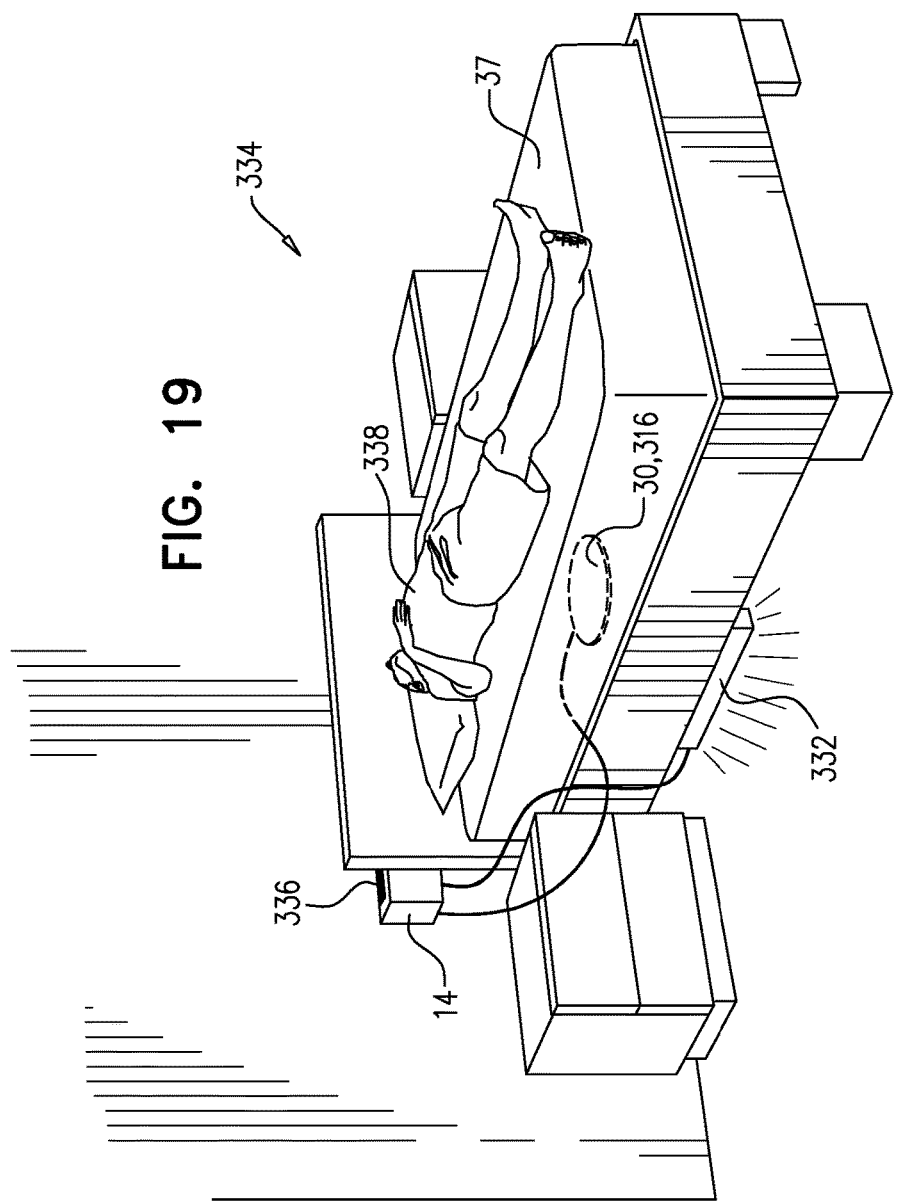
FIGS. 19-20 are schematic illustrations of apparatus for use with a person who is on a resting surface and for use with an illuminator, in accordance with some applications of the present invention.

Reference is now made to FIG. 19, which is a schematic illustration of apparatus 334 for use with a person 338 who is on a resting surface 37 (e.g., a bed) and for use with an illuminator 332, in accordance with some applications of the present invention. (Illuminator 332 may be integrated with resting surface 37, as shown in FIG. 19, or disposed at the side of the resting surface, e.g., on a night table.) Apparatus 334 comprises a sensor 316 configured to monitor person 338 and generate a signal in response thereto. Sensor 316 may comprise, for example, non-contact motion sensor 30, configured to sense motion on resting surface 37 and generate a motion signal in response thereto. Alternatively or additionally, sensor 316 may comprise at least one sensor of another type, such as an electromyographic sensor and/or an imaging sensor.

Control unit 14 is configured to analyze the signal from the sensor, and, in response thereto, calculate a bed-exit likelihood, which is a likelihood that the person has left the resting surface and/or a likelihood that the person is preparing to leave the resting surface. ("Preparing to leave the resting surface" may be defined, for example, as "intending to leave the resting surface within a given period of time, e.g., 2 minutes".) In response to the bed-exit likelihood, control unit 14 selects an illumination intensity value from a set of at least three values, and sets an illumination intensity of illuminator 332 to the selected illumination intensity value. For example, from a set of "high", "low", and "off", control unit may select "high" in response to a relatively high likelihood, "low" in response to a lower likelihood, and "off" in response to a relatively low likelihood. (The set of "high", "low", and "off" is being used here as an example only. In practice, the set of values may contain any number of values that is at least three.) The control unit sets the illumination intensity by sending a wired or wireless signal to the illuminator. (Similarly, with respect to all descriptions herein of the control unit controlling a device, e.g., the communication device, waking mechanism, etc. shown in any of FIGS. 20-23, it is noted that the control unit controls the device by sending a wired or wireless signal to the device.) In calculating the likelihood that the person has left the resting surface, the control unit may, for example, use one or more of the bed-exit-detection techniques described in US 2013/0267791 to Halperin, which is incorporated herein by reference.

Typically, in response to analyzing the signal, control unit 14 calculates a likelihood that the person is awake (e.g., using one or more of the awakening-detection techniques described in US 2013/0267791 to Halperin, which is incorporated herein by reference), and calculates the bed-exit likelihood in response thereto. For example, if the motion signal from motion sensor 30 is indicative of the person being awake, the control unit may calculate a relatively high likelihood that the person is awake, and, in response thereto, a relatively high likelihood that the person is preparing to leave the resting surface. Alternatively or additionally, the control unit calculates a likelihood that the person is sitting (e.g., using one or more of the techniques described in US 2013/0267791 to Halperin, which is incorporated herein by reference), and calculates the bed-exit likelihood in response thereto. For example, the control unit may calculate a relatively high likelihood that the person is sitting, and, in response thereto, a relatively high likelihood that the person is preparing to leave the resting surface. Alternatively or additionally, the control unit calculates a signal-to-noise ratio (SNR) of the signal (e.g., by using a real-time noise estimator, and/or as described in US 2013/0267791 to Halperin, which is incorporated herein by reference), and calculates the bed-exit likelihood in response thereto. Typically, a relatively high signal-to-noise ratio is indicative that the person is in bed, whereas a relatively low signal-to-noise ratio is indicative that the person has left the bed. Therefore, the control unit typically calculates a higher bed-exit likelihood in response to calculating a first signal-to-noise ratio, relative to calculating a second signal-to-noise ratio that is higher than the first signal-to-noise ratio.

In some applications, the control unit calculates both types of bed-exit likelihood, i.e., both the likelihood that the person has left the resting surface, and the likelihood that the person is preparing to leave the resting surface. In response to the likelihood that the person has left the resting surface, the control unit identifies a first illumination intensity value from the set of values, and in response to the likelihood that the person is preparing to leave the resting surface, the control unit identifies a second illumination intensity value from the set of values. The control unit then selects a maximum value of the first illumination intensity value and the second illumination intensity value, and sets the illumination intensity of the illuminator to the maximum value. For example, referring again to the set of "high", "low", and "off", if there is a relatively low likelihood that the person has left the bed, such that the first selected value is "off", but there is a relatively high likelihood that the person is preparing to leave the bed, such that the second selected value is "high", the control unit will set the illuminator to "high". Alternatively, for example, if there is a relatively high likelihood that the person has left the bed, such that the first selected value is "high", the control unit will set the illuminator to "high", regardless of the likelihood that the person is preparing to leave the bed.

Typically, control unit 14 selects the illumination intensity value by applying to the bed-exit likelihood a function that is generally monotonically increasing with respect to the bed-exit likelihood, and selecting the output of the function as the illumination intensity value. (In the context of the present application, a function that is generally monotonically increasing is a function for which at least 90% of the output values are not less than the preceding output value. The same definition applies to generally monotonically decreasing, mutatis mutandis.) Typically, the control unit selects a zero illumination intensity value (i.e., "off"), in response to the bed-exit likelihood being less than a threshold. For example, the control unit may select a "high" intensity in response to likelihoods above 90%, a "low" intensity in response to likelihoods between 30% and 90%, and "off" in response to likelihoods below 30%.

In some applications, the control unit selects the illumination intensity value further in response to a time of day, a date, a geographical location, a sunrise time, and/or a sunset time. For example, if the person usually sleeps between 11 pm and 6 am, the control unit may select a "high" intensity in response to a likelihood of 90% at 7 am, but a "low" intensity in response to a likelihood of 90% at 3 am. Alternatively or additionally, apparatus 334 further comprises an ambient light detector 336 configured to detect a level of ambient light, and the control unit selects the illumination intensity value further in response to the level of ambient light. For example, in response to a likelihood of 90%, the control unit may select a "high" intensity if there is a relatively low level of ambient light, but only a "low" intensity if there is a relatively high level of ambient light.

In some applications, the control unit is further configured to, in response to the bed-exit likelihood and/or a time of day, select an illumination color value from a set of at least two color values, and set an illumination color of the illuminator to the selected illumination color value. For example, the control unit may select a red color in response to a relatively low bed-exit likelihood, and a blue color in response to a relatively high bed-exit likelihood; alternatively or additionally, the control unit may select a red color during typical sleeping hours, and a blue color otherwise. For at least some people, red illumination is more conducive to sleep than is blue illumination. Thus, the selection of the red color during typical sleeping hours, rather than the blue color, helps the person fall asleep upon returning to bed. Furthermore, the selection of the red color in response to a relatively low bed-exit likelihood helps minimize the disturbance to the person in the event of a "false positive", i.e., in the event that the person is not actually preparing to leave the bed.

In some applications, control unit 14 is configured to identify a sleep stage of person 338. In such applications, the control unit may ascertain, in response to analyzing the signal, that person 338 is in a light sleep stage on the resting surface, and in response thereto, drive illuminator 332 to wake the person by illuminating. Waking the person in this manner may be helpful, for example, if the person shares a bed and/or a room with a second person (as described hereinbelow with reference to FIG. 20), since an increase in illumination may be less disturbing to the second person than the sounding of an alarm. Since, however, the increase in illumination may be insufficient to wake person 338 if (s)he is in a relatively deep sleep, illumination is used to wake the person only if the person is in a light sleep stage.

Figure 20:
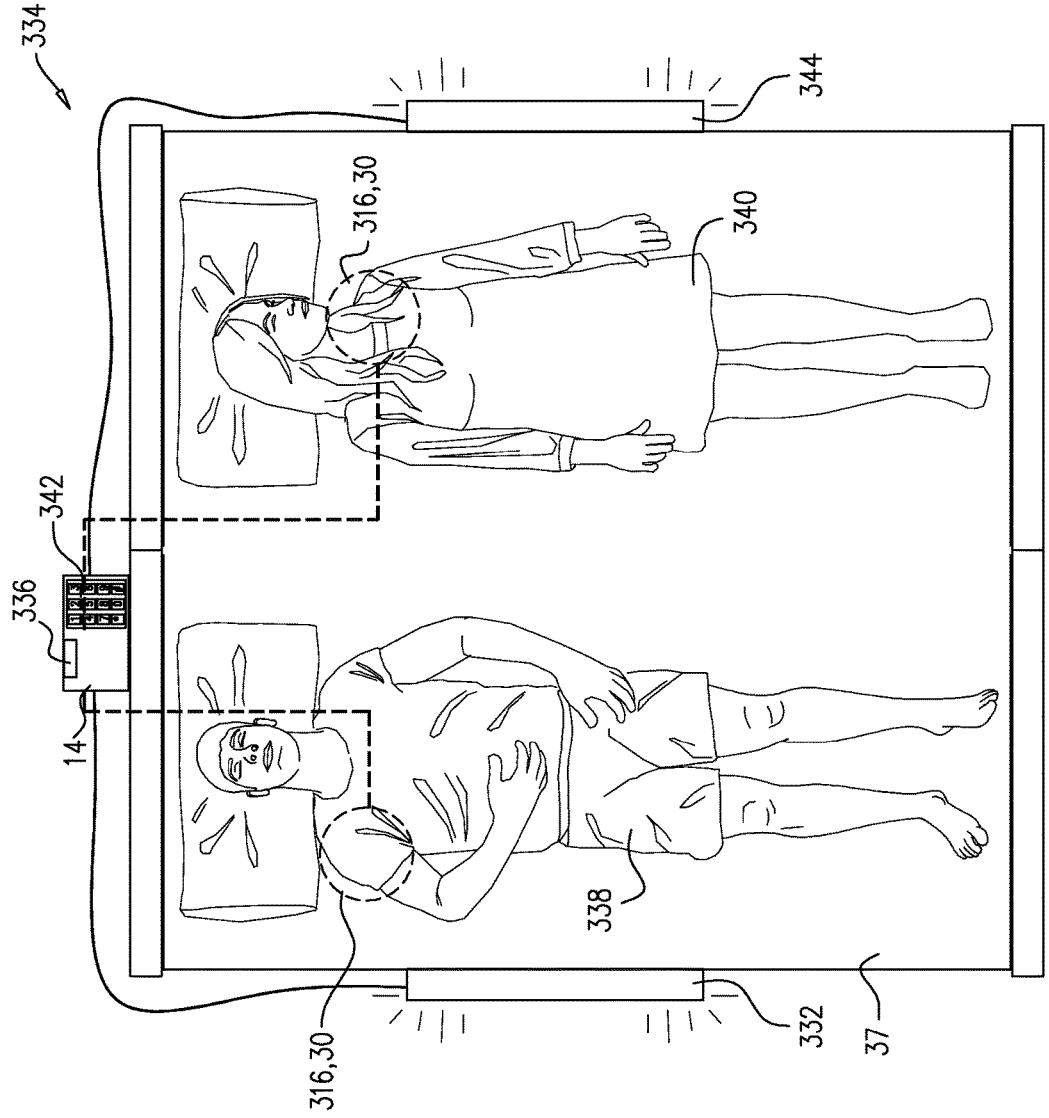

Reference is now made to FIG. 20, which is a schematic illustration of apparatus 334, in accordance with some applications of the present invention. In some applications, first person 338 shares a sleeping area (e.g., a bed, and/or a room) with a second person 340. In such applications, the control unit identifies a second-person-sleeping likelihood, which is a likelihood that the second person is sleeping, and selects the illumination intensity value further in response to the second-person-sleeping likelihood. For example, in response to a bed-exit likelihood of 90%, the control unit may select a "high" intensity if the second-person-sleeping likelihood is relatively low, but only a "low" intensity if the second-person-sleeping likelihood is relatively high. Typically, the control unit applies to the second-person-sleeping likelihood a function that is generally monotonically decreasing with respect to the second-person-sleeping likelihood, and selects the output of the function as the illumination intensity value. The control unit may apply a two-variable function to (a) the bed-exit likelihood and (b) the second-person-sleeping likelihood, where the two-variable function is generally monotonically increasing with respect to the bed-exit likelihood, and generally monotonically decreasing with respect to the second-person-sleeping likelihood. An example of such a function, for each of the two types of bed-exit likelihood, is shown in the tables below. (For simplicity and ease of illustration, the second-person-sleeping likelihood is shown as having one of only two values: "low", and "high", even though, in practice, it can take on any number of values between 0 and 100%.)

TABLE 1

| Likelihood that the first person has exited the bed | Lighting intensity | |
|---|---|---|
| | High second-person-sleeping likelihood | Low second-person-sleeping likelihood |
| 0% | 0% | 0% |
| 10% | 0% | 0% |
| 20% | 0% | 10% |
| 30% | 10% | 20% |
| 40% | 10% | 30% |
| 50% | 20% | 40% |
| 60% | 30% | 40% |
| 70% | 50% | 60% |
| 80% | 60% | 80% |
| 90% | 80% | 100% |
| 99% | 80% | 100% |

TABLE 2

| Likelihood that the first person is preparing to exit the bed | Lighting intensity | |
|---|---|---|
| | High second-person-sleeping likelihood | Low second-person-sleeping likelihood |
| 0% | 0% | 0% |
| 10% | 0% | 0% |
| 20% | 0% | 0% |
| 30% | 0% | 0% |
| 40% | 10% | 0% |
| 50% | 10% | 10% |
| 60% | 20% | 10% |
| 70% | 20% | 10% |
| 80% | 20% | 20% |
| 90% | 20% | 20% |
| 99% | 30% | 20% |

As described hereinabove with reference to FIG. 19, the control unit may select two intensity values in response to, respectively, the two types of bed-exit likelihood, and select the maximum of the two values as the illuminator intensity. For example, if the likelihood that the first person has exited the bed is 30%, the likelihood that the first person is preparing to exit the bed is 60%, and the second-person-sleeping likelihood is "low", the control unit may select (per Tables 2 and 3 above) the maximum of a 20% intensity and a 10% intensity, which is 20%.

In some applications, the control unit selects a zero illumination intensity value (i.e., an "off" value), in response to the second-person-sleeping likelihood exceeding a threshold. This selection may also be in response to other factors, e.g., the bed-exit likelihood. For example, if the bed-exit likelihood is relatively high, the control unit may not select a zero illumination intensity value, even though the second-person-sleeping likelihood exceeds the threshold.

In some applications, a single sensor 316 senses the motion of both persons. This may be the case, for example, when the first and second persons share a bed, and a single motion sensor 30 is used to sense motion on the bed. The control unit analyzes the motion signal from the single sensor, and calculates the second-person-sleeping likelihood in response thereto. (When a single motion sensor 30 is used, subject identification module 102 (FIG. 4) may be used to differentiate between the motion of the first person and the motion of the second person.) In other applications, such as the application shown in FIG. 20, a first sensor 316*a* (e.g., a first motion sensor 30*a*) monitors first person 338, while a second sensor 316*b* (e.g., a second motion sensor 30*b*) monitors second person 340. (The two persons may be on the same bed, or on different beds.) The control unit analyzes the signal (e.g., a motion signal) from second sensor 316*b*, and in response thereto, calculates the second-person-sleeping likelihood.

Alternatively or additionally, the control unit identifies the second-person-sleeping likelihood in response to a time of day. For example, if the second person usually sleeps between 11 pm and 6 am, the control unit may identify a higher second-person-sleeping likelihood between 11 pm and 6 am, relative to other times of the day. Alternatively or additionally, apparatus 334 further comprises an input unit 342, and the control unit identifies the second-person-sleeping likelihood in response to an input thereto. For example, the second person may use input unit 342 to indicate that (s)he is going to sleep, and the control unit will, in response to the input, begin to identify a higher second-person-sleeping likelihood. Input unit 342 may be part of user interface (U/I) 24, described hereinabove with reference to FIG. 1, or may be a separate unit, such as the input unit of a mobile phone that is in communication with the control unit.

In some applications, as shown in FIG. 20, apparatus 334 is for use with both first illuminator 332 and a second illuminator 344, where the illuminators are located such that, when the first and second persons are on resting surface 37 (or on separate resting surfaces 37), first illuminator 332 is closer to the first person than to the second person, and second illuminator 344 is closer to the second person than to the first person. The control unit is configured to set an illumination intensity of the second illuminator to be different from the illumination intensity of the first illuminator, in response to (a) a likelihood that the second person has left resting surface 37, and/or a likelihood that the second person is preparing to leave resting surface 37 (i.e., the bed-exit likelihood for the second person), and (b) a likelihood that the first person is sleeping (i.e., a first-person-sleeping likelihood).

Reference is now made to FIG. 21, which is a schematic illustration of apparatus 346 for use with a waking mechanism 348 (e.g., an alarm clock, a mobile phone, an illuminator, and/or a vibrating element) that executes a waking routine to wake a subject 12 (e.g., first person 338) who is sleeping near second person 340, in accordance with some applications of the present invention. Apparatus 346 comprises a sensor 316, configured to monitor second person 340 and generate a signal in response thereto. Sensor 316 may comprise, for example, motion sensor 30, configured to sense motion on the resting surface 37 on which the second person is resting and generate a motion signal in response thereto. Alternatively or additionally, sensor 316 may comprise at least one sensor of another type, such as an electromyographic sensor and/or an imaging sensor.

Prior to execution of the waking routine, control unit 14 analyzes the signal from sensor 316. In response to analyzing the signal, the control unit identifies a likelihood that the second person is sleeping, and in response to the likelihood, sets an intensity of the waking routine by sending a signal to the waking mechanism. For example, in response to a relatively high likelihood, the control unit will set the intensity of the waking routine (e.g., the volume of an alarm) to be relatively low, so as to reduce disturbance to the second person. Following the beginning of the execution of the waking routine, the control unit analyzes the signal. If, in response to analyzing the signal, the control unit identifies that the subject has not woken, the control unit increases the intensity of the waking routine, e.g., increases the volume of an alarm. These steps may be repeated several times, until the control unit identifies that the subject has woken. In this manner, the chances of waking the second person are reduced. Alternatively or additionally, in response to a relatively high likelihood that the second person is sleeping, the control unit may activate an alternate waking mechanism that is less potentially disturbing to the second person, such as an illuminator (FIG. 20).

In some applications, control unit 14 further identifies a sleep stage of the second person, and sets the intensity of the waking routine in response to the identified sleep stage. For example, if the second person is in a deep sleep, and therefore less likely to be disturbed by the waking routine, the control unit may set the waking routine to a relatively high intensity.

FIG. 21 also shows apparatus 376 for use with a communication device 378 belonging to a first person 338, in accordance with some applications of the present invention. (It is noted that communication device 378 may be identical to waking mechanism 348.) Communication device 378 generates an alert upon receiving an incoming communication; for example, communication device 378 may include a mobile phone that rings upon receiving an incoming call.

In response to analyzing the signal from sensor 316, the control unit identifies a likelihood that the second person is sleeping, and controls an intensity of the alert in response to the identified likelihood. For example, in response to identifying that there is a relatively high likelihood that the second person is sleeping, the control unit may lower the intensity of the alert (e.g., lower the volume of the ring), or inhibit the communication device from activating the alert (e.g., mute the phone). In some applications, the control unit continually identifies the likelihood that the second person is sleeping, and continually controls the communication device in response thereto. (For example, the control unit may continually adjust the volume of the ringer of the phone, regardless of whether there is an incoming call.) In other applications, the control unit controls the intensity of the alert further in response to the communication device receiving the incoming communication, e.g., the control unit adjusts the volume of the ringer only upon the phone receiving an incoming call.

In some applications, the control unit controls the intensity of the alert in response to the identified sleep stage of second person 340. For example, if the second person is sleeping lightly (and is therefore relatively likely to be disturbed by the alert), the control unit may lower the volume of the ring more than if the second person were sleeping deeply or were awake.

FIG. 21 also shows apparatus 386 for use with a mechanism 388 (e.g., a toilet-flushing mechanism a window-opening mechanism) that is activated by a first person 338, in accordance with some applications of the present invention. In response to analyzing the signal from sensor 316 (e.g., motion sensor 30), the control unit identifies a likelihood that the second person is sleeping, and delays the activation of the mechanism, and/or inhibits (e.g., prevents) the activation of the mechanism, in response to the identified likelihood. For example, if the control unit identifies a high likelihood that second person 340 is sleeping, the control unit may delay the flushing of the toilet until the likelihood is reduced. (This may be effected, for example, by communicating a signal to a "smart" toilet flusher of the toilet.) In some applications, the control unit further identifies a sleep stage of the second person, and delays the activation of the mechanism in response to the identified sleep stage. For example, the flushing of the toilet may be delayed if the second person is sleeping lightly, but not if the second person is sleeping deeply or is awake.

In order to reduce contamination of the motion signal from second person 340, the applications shown in FIG. 21 may be practiced in combination with subject identification module 102 (FIG. 4), and/or in combination with mechanical filtering provided by, for example, sensor plate 140 with hardened edges 142 (FIG. 5), sensor plate 238 with rigid edge region 227 (FIG. 9A), etc., as described hereinabove.

Figure 22:
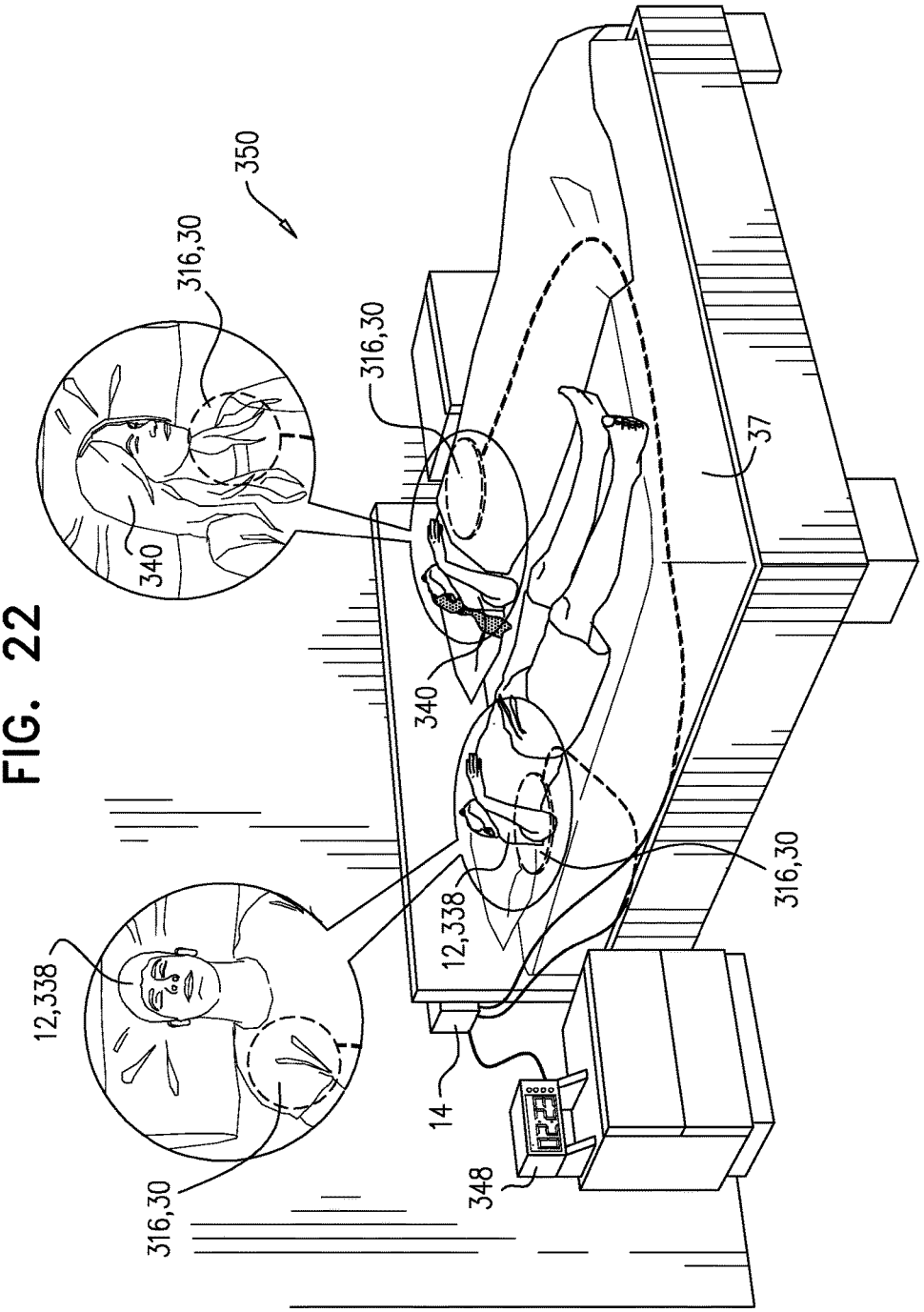
FIG. 22 is a schematic illustration of apparatus for use with a waking mechanism that executes a waking routine to wake a subject who is on a resting surface, in accordance with some applications of the present invention.

Reference is now made to FIG. 22, which is a schematic illustration of apparatus 350 for use with a waking mechanism 348 (e.g., an alarm clock, a mobile phone, an illuminator, and/or a vibrating element) that executes a waking routine to wake a subject 12 (e.g., a first person 338) who is on a resting surface 37, in accordance with some applications of the present invention. Apparatus 350 comprises a sensor 316, configured to monitor subject 12 and generate a signal in response thereto. Sensor 316 may comprise, for example, non-contact motion sensor 30, configured to sense motion on the resting surface 37 on which the subject is resting and generate a motion signal in response thereto. Alternatively or additionally, sensor 316 may comprise at least one sensor of another type, such as an electromyographic sensor and/or an imaging sensor. Prior to execution of the waking routine, control unit 14 analyzes the signal from the sensor. If the control unit identifies, in response to the analyzing, that the subject is not on the resting surface, the control unit inhibits waking mechanism 348 from executing the waking routine.

In some applications, control unit 14 is further configured to identify a likelihood that a second person 340 is sleeping near the subject, and set an intensity of the waking routine in response to the likelihood by sending a signal to the waking mechanism. Generally, this is done as described hereinabove with reference to FIG. 21; for example, the control unit may increase the intensity of the waking routine one or more times, until the subject is woken. Furthermore, in some applications, the control unit changes an angle of the resting surface (e.g., as described in US 2013/0267791 to Halperin, which is incorporated herein by reference), in response to identifying that the waking routine has not woken the subject. The change in angle of the resting surface may facilitate the waking of the subject, while causing only a relatively small disturbance to other individuals in the area, e.g., second person 340. In some applications, the control unit identifies a sleep stage of the subject, and changes the angle of the resting surface in response to the identified sleep stage. For example, if the subject is in a deep sleep, the control unit may change the angle by a relatively large amount, such as to increase the probability that the subject will wake up.

In some applications, if control unit 14 identifies, in response to analyzing the signal following the beginning of execution of the waking routine, that the subject has woken, the control unit changes the angle of the resting surface. For example, the control unit may move the upper portion of the bed to a more upright position, in order to facilitate the subject's exit from bed.

Although FIG. 22 shows two sensors 316, it is noted that the scope of the present invention includes the use of exactly one sensor 316 (e.g., exactly one motion sensor 30) to monitor both first person 338 and second person 340. In such applications, subject identification module 102 (FIG. 4) may be used to differentiate between the motion of the first person and the motion of the second person.

Figure 23:
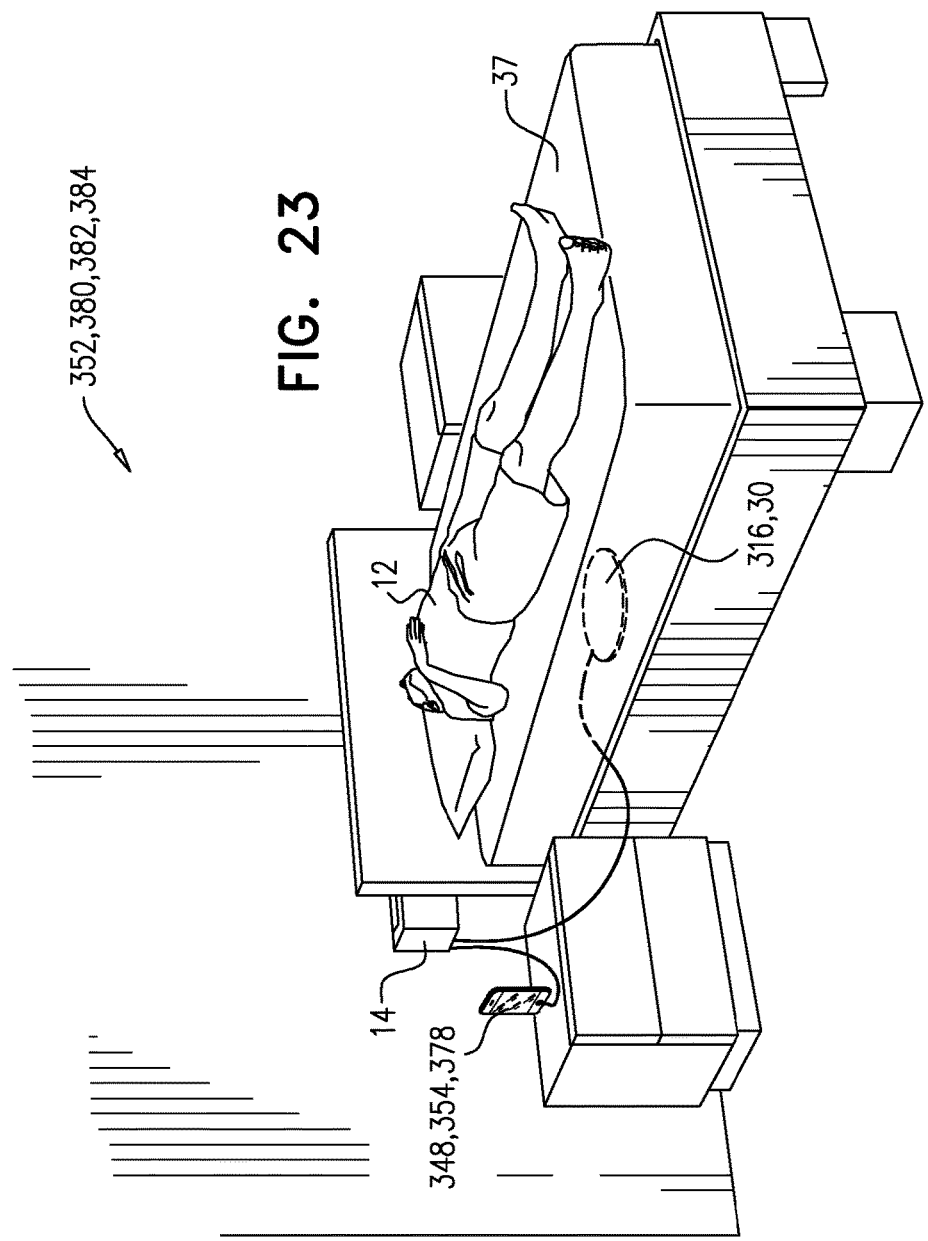
FIG. 23 is a schematic illustration of apparatus for use with (i) a waking mechanism that executes a waking routine to wake a subject who is on a resting surface, and (ii) an output unit, in accordance with some applications of the present invention.

Reference is now made to FIG. 23, which is a schematic illustration of apparatus 352 for use with (i) a waking mechanism 348 that executes a waking routine to wake a subject 12 who is on a resting surface 37, and (ii) an output unit 354, in accordance with some applications of the present invention. (In some applications, as shown in FIG. 23, a single device, such as a mobile phone, may include both waking mechanism 348 and output unit 354.) Apparatus 350 comprises a sensor 316, configured to monitor subject 12 and generate a signal in response thereto. Sensor 316 may comprise, for example, motion sensor 30, configured to sense motion on the resting surface 37 on which the subject is resting and generate a motion signal in response thereto. Alternatively or additionally, sensor 316 may comprise at least one sensor of another type, such as an electromyographic sensor and/or an imaging sensor.

Prior to execution of the waking routine, control unit 14 analyzes the signal from sensor 316, and, in response to analyzing the signal, identifies a sleep stage of the subject. Upon the subject waking, the control unit drives output unit 354 to output the identified sleep stage to the subject, only if the identified sleep stage is a slow-wave (i.e., deep) sleep stage. (The output may include a technical description of the sleep stage, e.g., "NREM stage 3", and/or a non-technical description, e.g., "deep sleep".) Alternatively or additionally, the control unit drives output unit 354 to output a recommendation to the subject to perform a wakefulness-inducing activity, only if the identified sleep stage is a slow-wave sleep stage. For example, the control unit may drive the output unit to output an audio and/or visual message such as "You were just woken from a deep sleep. Consider doing some light exercise, or drinking a coffee." Alternatively or additionally, the control unit drives the output unit to output a recommendation to the subject to refrain from operating a vehicle for a specific period of time, only if the identified sleep stage is a slow-wave sleep stage.

In some applications, in response to analyzing the signal prior to the execution of the waking routine, the control unit identifies at least one physiological parameter of the subject, such as the subject's heart rate, heart rate variability, respiration rate, respiration rate variability, and/or blood pressure. The control unit then drives the output unit to output the physiological parameter, upon the subject waking. In some applications, the control unit drives the output unit to output the physiological parameter, only if the physiological parameter deviates from a baseline value. The output of the physiological parameter may help the subject manage his/her post-waking activities. For example, if the subject sees that his/her heart rate is relatively high, the subject may refrain from drinking coffee. In some applications, in response to the physiological parameter deviating from the baseline value, the control unit drives the output unit to output a recommendation to the subject to perform a specific activity (e.g., exercise), and/or a recommendation to refrain from performing a specific activity (e.g., drinking coffee).

FIG. 23 also shows apparatus 380 for use with communication device 378 (e.g., a mobile phone). In response to analyzing the signal from sensor 316 (e.g., motion sensor 30), control unit 14 identifies a sleep stage of subject 12, and controls an intensity of the alert that is generated by communication device 378 in response to the identified sleep stage. In some applications, the control unit lowers the intensity of the alert in response to a relatively light sleep stage, relative to a deeper sleep stage. For example, the subject may indicate before going to sleep that (s)he wishes to be woken upon receiving a call, but in a manner that generally minimizes potential disturbances to others. By providing for an alert intensity that is generally increasing with the deepness of the subject's sleep, the control unit generally provides for the ring volume to be loud enough to wake the subject up, but not significantly louder than necessary. In other applications, the control unit controls the intensity in the opposite manner, i.e., it raises the intensity of the alert in response to a relatively light sleep stage, relative to a deeper sleep stage. (For example, the control unit may inhibit the communication device from activating the alert, in response to the identified sleep stage being a slow-wave sleep stage, but allow the alert to be activated in response to a light sleep stage.) This behavior may be in response to the subject indicating before going to sleep that (s)he does not wish to be woken from a deep sleep, but does not mind being woken from a light sleep.

In some applications, as described hereinabove with reference to FIG. 21, the control unit controls the intensity of the alert further in response to the communication device receiving the incoming communication. In some applications, apparatus 380 further includes elements of apparatus 376, described hereinabove with reference to FIG. 21. For example, the control unit may be further configured to identify a likelihood that a second person 340 (FIG. 21) is sleeping near the subject, and control the intensity of the alert, further in response to the likelihood.

FIG. 23 also shows apparatus 382 for inhibiting outgoing communication from communication device 378 (e.g., a mobile phone). In response to analyzing the signal from sensor 316 (e.g., motion sensor 30), control unit 14 identifies that the subject is sleeping, and, in response thereto, inhibits (e.g., prevents) outgoing communication from the communication device. By doing so, the control unit may at least partially prevent "sleeptexting" by subject 12, and/or may at least partially prevent another user (e.g., a mischievous child) from using the subject's device without the subject's permission. In inhibiting the outgoing communication, the control unit may at least partially disable the communication device (e.g., disable the texting and/or calling functionality of a mobile phone). In some applications, the control unit drives the communication device to prompt the user to input an answer to an objective question (e.g., "What is the capital of Kansas?"), and allows outgoing communication from the communication device only if the answer is correct. In this manner, outgoing communication from a sleeping subject 12 (e.g., "sleeptexting") may be at least partially prevented.

FIG. 23 also shows apparatus 384 for use with a subject 12 who is on a resting surface 37, in accordance with some applications of the present invention. In response to analyzing the signal from sensor 316 (e.g., motion sensor 30), the control unit identifies a likelihood that the subject has left the resting surface, and/or a likelihood that the subject is preparing to leave the resting surface. In response to the likelihood(s), and in response to the control unit further identifying that the subject is sleeping, the control unit generates a "sleepwalking" alert. For example, if the signal gave no indication that the subject woke prior to the indication that the subject left the bed, an alert will be generated. In response to the alert, a caregiver may come to the subject's aid.

Figure 24:
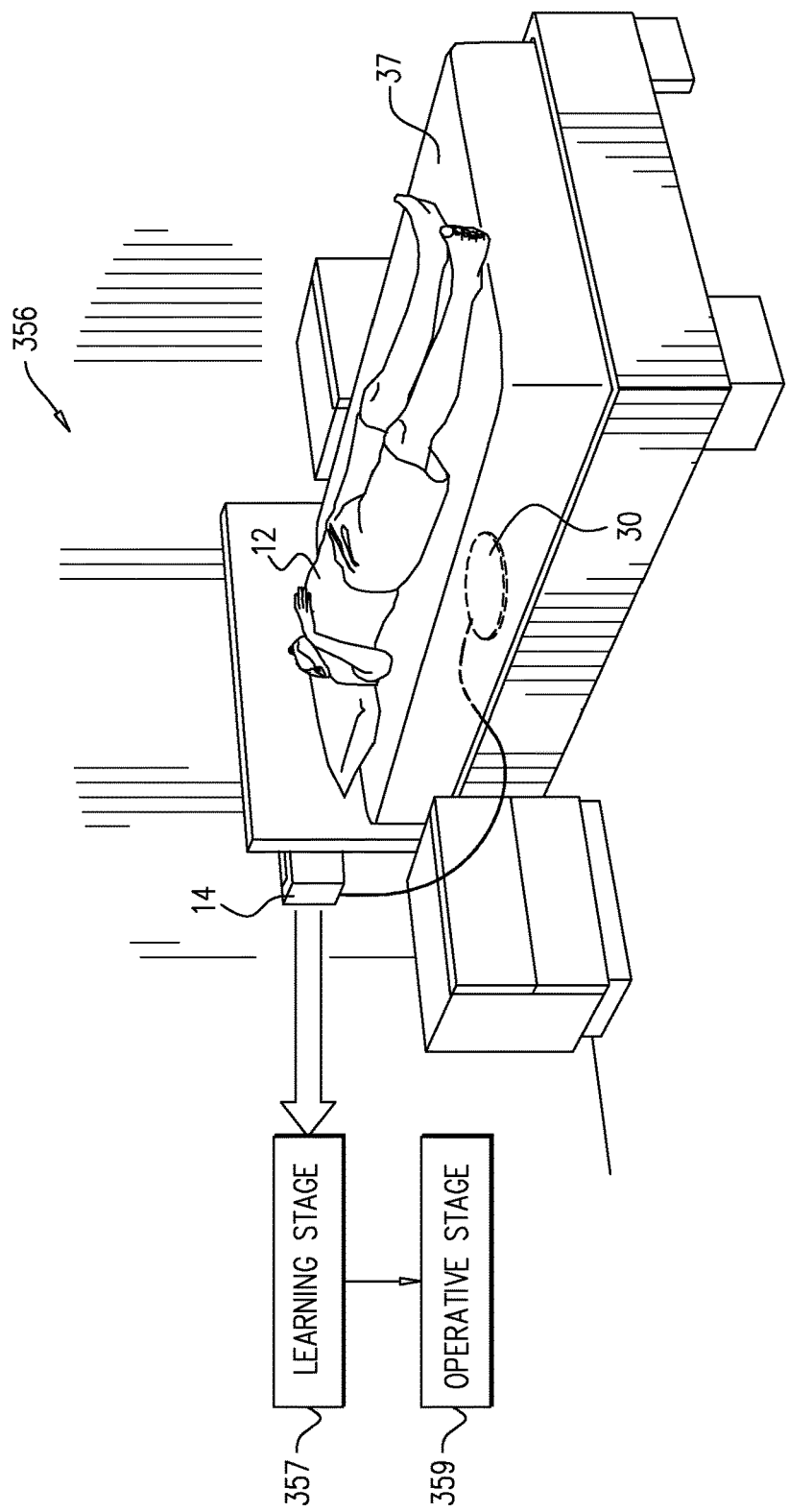
FIG. 24 is a schematic illustration of apparatus for identifying a posture of a subject, in accordance with some applications of the present invention.

Reference is now made to FIG. 24, which is a schematic illustration of apparatus 356 for identifying a posture of a subject 12, in accordance with some applications of the present invention. Apparatus 356 comprises a single motion sensor 30, configured to sense motion of a person (e.g., the subject, or any other person) without contacting or viewing the person or clothes the person is wearing, and generate a motion signal in response thereto.

During a learning stage 357, a person adopts a number of different lying postures at respective times, while being monitored by motion sensor 30. Control unit 14 receives a plurality of inputs indicative of postures of the person at the respective times. For example, for each posture that the person adopts, the control unit may receive an input that describes (or "classifies") the posture, e.g., "supine", "prone", etc. By using the plurality of inputs and by analyzing the motion signal at the respective times, the control unit learns a posture-identification technique. For example, the control unit may identify various features of the motion signal, such as amplitude, dominant frequencies, etc. that discriminate between the various postures. Then, during an operative stage 359 that follows learning stage 357, when the subject is lying on resting surface 37 (e.g., a hospital bed) and being monitored by sensor 30, the control unit uses the learned posture-identification technique to identify the posture of the subject. For example, by analyzing the motion signal, the control unit may identify particular features of the signal that, during the learning stage, were found to be indicative of a particular posture. The control unit then identifies that particular posture as being the posture of the subject.

Preferably, in order to improve the efficacy of the learned posture-identification technique, learning stage 357 is performed with the subject lying on resting surface 37, rather than with a different person and/or a different resting surface. However, in some applications (e.g., when the physical condition of subject 12 does not allow for the subject to participate in the learning stage), control unit 14 uses a more "generic" posture-identification technique that was learned (e.g., by the control unit) from one or more other persons lying on the same, or a different, resting surface. In using this technique, the control unit may make use of parameters relating to the subject's physical condition (e.g., the subject's body mass index), and/or the resting surface (e.g., a thickness of a mattress), in order to more effectively perform the posture identification.

In some applications, the control unit is further configured to verify compliance of a healthcare provider for the subject with a pressure-ulcer-prevention protocol, in response to identifying the posture.

Figure 25:
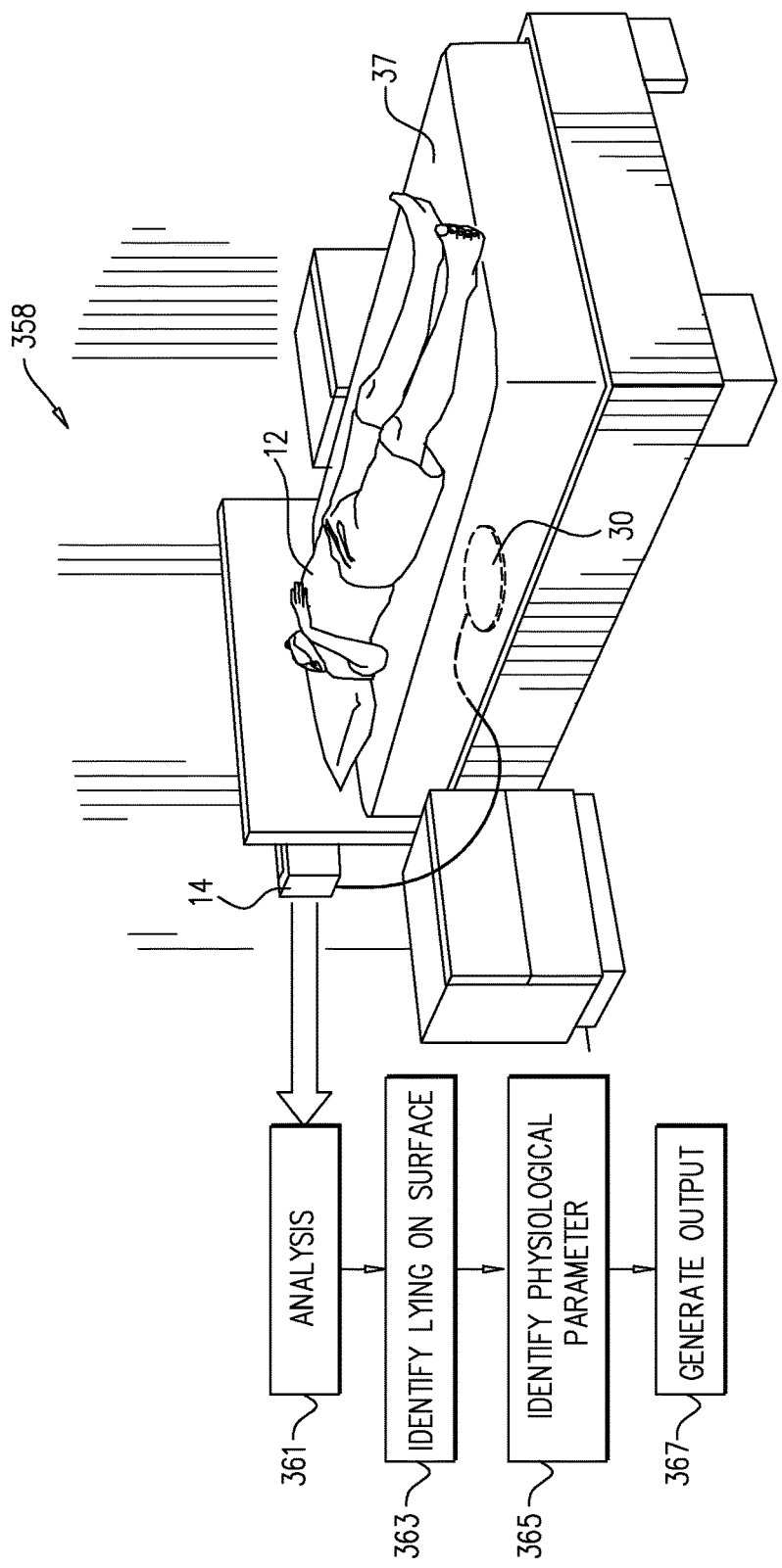
FIG. 25 is a schematic illustration of apparatus for monitoring a subject, in accordance with some applications of the present invention.

Reference is now made to FIG. 25, which is a schematic illustration of apparatus 358 for monitoring a subject 12, in accordance with some applications of the present invention. Apparatus 358 comprises a motion sensor 30, configured to sense motion of the subject on resting surface 37 and generate a motion signal in response thereto. Control unit 14 analyzes the motion signal (analysis step 361), and, in response thereto, identifies that the subject has lain on the resting surface (first identification step 363). Subsequently to the subject lying on the resting surface, the control unit identifies a physiological parameter relating to a physiological slowing time of the subject (second identification step 365). For example, the control unit may identify a parameter relating to a slowing of a heart rate of the subject, such as the time for the heart rate to slow to a normal resting value. Alternatively or additionally, the control unit may identify a parameter relating to a slowing of a respiratory rate of the subject, such as the time for the respiratory rate to slow to a normal resting value. If the control unit identifies that the physiological parameter may be indicative of a physiological deterioration of the subject, the control unit generates an output (output generation step 367).

In some applications, the control unit identifies that the physiological parameter may be indicative of a physiological deterioration of the subject by identifying that the physiological parameter deviates from a baseline value. For example, if, in a healthy person, the heart rate generally slows to a normal resting value within 1-5 minutes, but the subject's heart rate slowed to a normal resting value within more than 10 minutes (or did not slow to a normal resting value at all, within a given period of time), the control unit generates an output, e.g., a warning to a physician. The baseline may be with reference to the subject, rather than with reference to a healthy person. For example, the baseline heart-rate slowing time may be the average slowing time for the subject during the previous 7 days. In some applications, the control unit is further configured to calculate the baseline value by analyzing the motion signal following each of a plurality of instances of a person (e.g., any healthy person, or the subject) lying on a resting surface.

Alternatively or additionally, the control unit identifies that the physiological parameter may be indicative of a physiological deterioration of the subject by identifying a deteriorating trend in the physiological parameter. For example, if, over the last several days, the heart-rate slowing time of the subject has been steadily increasing, the control unit may identify this as a deteriorating trend, and may generate an output, e.g., a warning, in response thereto.

In some applications, the control unit identifies a possible physiological condition of the subject, in response to identifying that the physiological parameter may be indicative of a physiological deterioration of the subject, and generates an output in response thereto. For example, (a) in response to a deteriorating (e.g., increasing) trend in heart-rate slowing time, and/or a heart-rate slowing time that deviates from (e.g., is greater than) a baseline value, the control unit may identify that the subject possibly suffers from clinical anxiety, or (b) in response to a deteriorating (e.g., increasing) trend in respiratory-rate slowing time, and/or a respiratory-rate slowing time that deviates from (e.g., is greater than) a baseline value, the control unit may identify that the subject possibly suffers from asthma. In some applications, the control unit identifies an activity level of the subject, in response to analyzing the motion signal, and regulates the output in response to the identified activity level. Typically, the control unit regulates the output by generating the output only if an adjusted physiological parameter deviates from the baseline value, or if the physiological parameter deviates from an adjusted baseline value. For example, in response to identifying a relatively high activity level, the control unit may adjust a baseline heart-rate slowing time of 5 minutes to 7 minutes, and hence, may not generate the output unless the heart-rate slowing time of the subject exceeds 7 minutes. Alternatively or additionally, the control unit withholds generating the output if the identified activity level is greater than a threshold, and/or does not begin measuring the slowing time until the activity level of the subject falls below a threshold. By regulating the output in this manner, the control unit may at least partially avoid generating false alarms.

Figure 26:
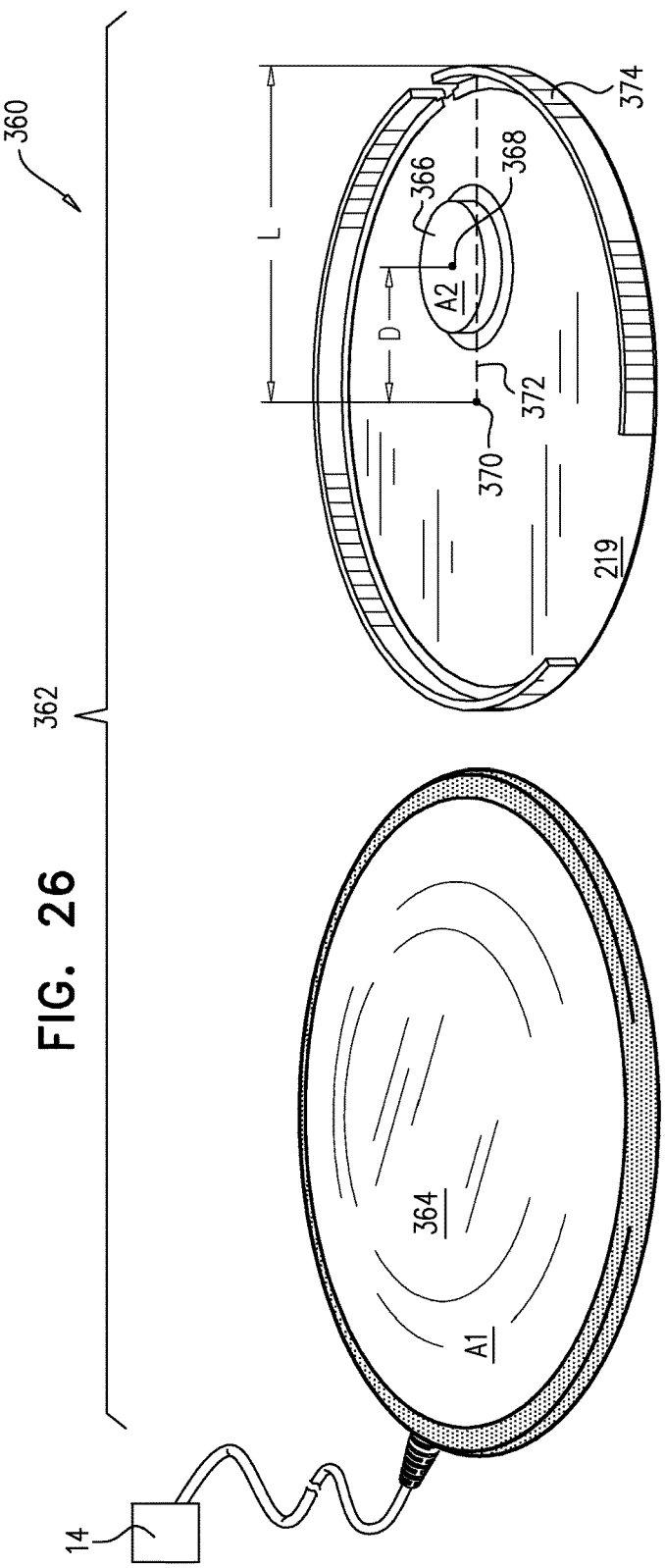
FIG. 26 is a schematic illustration of apparatus for monitoring a subject, in accordance with some applications of the present invention.

Reference is now made to FIG. 26, which is a schematic illustration of apparatus 360 for monitoring a subject (e.g., subject 12), in accordance with some applications of the present invention. Apparatus 360 comprises a sensor plate 362 comprising an upper surface 364 that is configured to deflect in response to motion of the subject. Apparatus 360 also comprises a sensor 366, such as a ceramic piezoelectric sensor, vibration sensor, pressure sensor, or strain sensor disposed underneath upper surface 364. Sensor 366 generates a motion signal in response to the deflection of upper surface 364, and control unit 14 analyzes the motion signal and generates an output indicative of a condition of the subject, in response thereto. Motion sensor 30, described throughout the present application, may comprise sensor plate 362 and sensor 366.

Center 368 of sensor 366 is typically disposed at a distance D from a center 370 of sensor plate 362 that is at least 30% and/or less than 70%, e.g., between 30% and 70%, of a length L of a line 372 drawn from center 370 of the sensor plate to a perimeter 374 of the sensor plate, through center 368 of the sensor. (In this context, the "center" of the sensor is the centroid of a surface of the sensor, and similarly, the "center" of the sensor plate is the centroid of a surface of the sensor plate.) Generally, the disposition of sensor 366 in this manner is advantageous in at least two ways:

(i) The sensor is more sensitive to deflections of the sensor plate at frequencies between 1 and 100 Hz, relative to if the sensor were disposed more toward the center or the perimeter of the sensor plate. The range of 1-100 Hz is significant, at least in that heartbeat-related signals and, to a lesser extent, respiratory-related signals from the subject include harmonic frequencies of interest that are within this range. (These harmonic frequencies may be used, for example, to predict a physiological condition of the subject, as described in U.S. Pat. No. 8,679,034, which is incorporated herein by reference.) The greater sensitivity to the aforementioned range of frequencies is due at least to (a) the asymmetric configuration of the sensor and sensor plate, and (b) the relative stiffness of upper surface 364 at the location at which sensor 366 is disposed.

(ii) For cases in which subject 12 shares a bed with a partner, sensor plate 362 may be placed underneath the subject such that sensor 366 faces toward the near edge of the bed, i.e., away from the partner. In this manner, sensor 366 will be less affected by signals from the partner, relative to if it were disposed closer to the center of the sensor plate. In this regard, it is noted that sensor plate 362 may also include elements of sensor plate 238, described hereinabove with reference to FIGS. 9A-B and 10A-D. For example, sensor plate 362 may include noise filter plate 226 (FIG. 9B), which, as described hereinabove, allows for mechanical filtering of signals coming from the partner. Alternatively or additionally, for example, sensor plate 362 may include a slot 219 (as shown in FIG. 26), for improved sensing of the subject's signal and filtering of the partner's signal, as described hereinabove with reference to FIG. 10C.

Typically, the upper surface area A2 of the sensor is between 0.2 and 30 cm2. (FIG. 25 shows the lower surface area of the sensor, which is typically very close or identical to the upper surface area.) Further typically, the upper surface area A1 of the sensor plate is between 20 and 200 cm2 or between 200 and 710 cm2. In some applications, upper surface area A1 of the sensor plate is between 2 and 8 times greater, or between 8 and 30 times greater, than upper surface area A2 of the sensor.

Figure 27B:
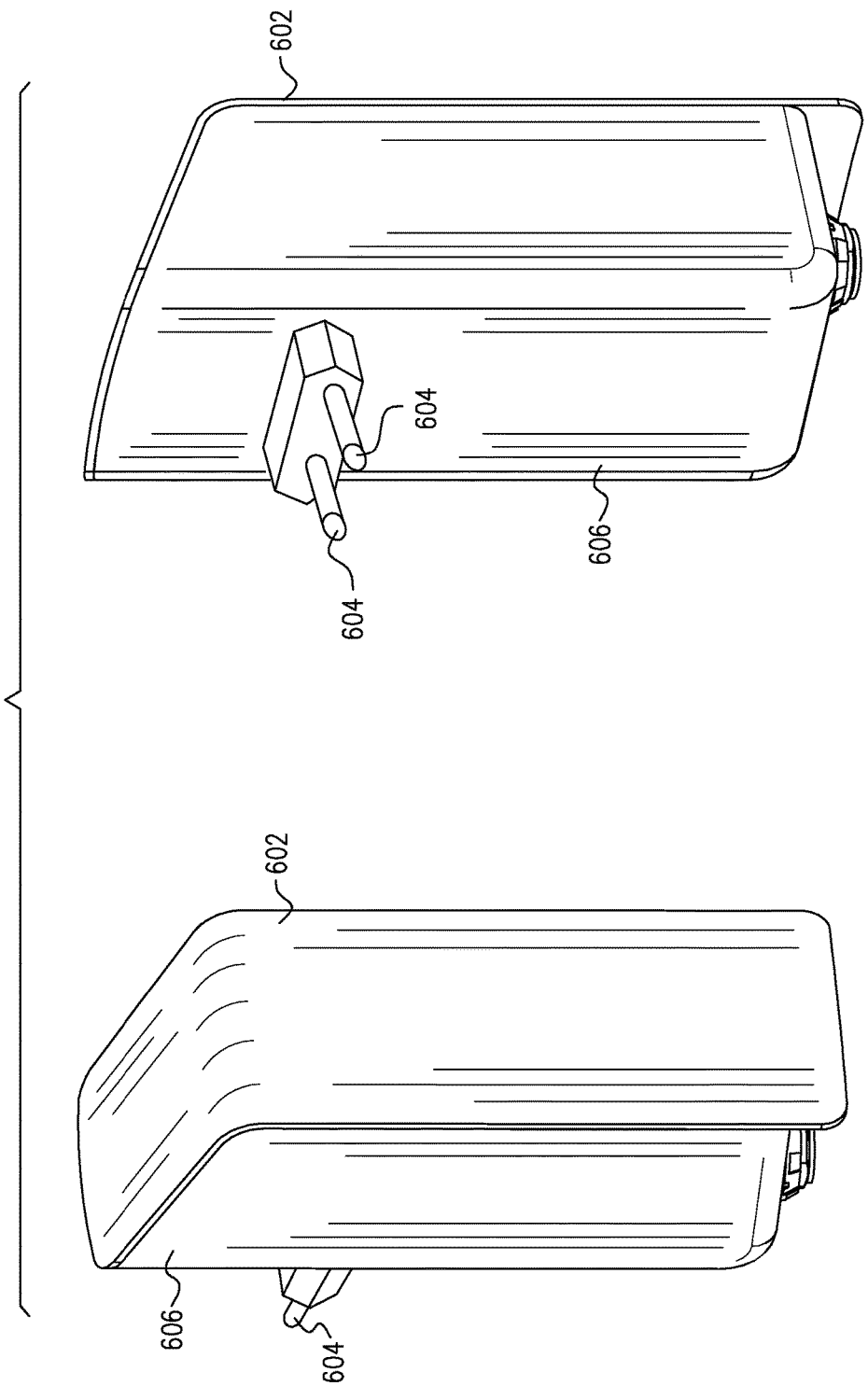
FIG. 27B is a schematic illustration of a mains-power-connection device, in accordance with some applications of the present invention.

Reference is now made to (a) FIG. 27A, which is a schematic illustration of apparatus 600 comprising motion sensor 30, a mains-power-connection device 602, and control unit 14, and (b) FIG. 27B, which is a schematic illustration of mains-power-connection device 602, in accordance with some applications of the present invention. Mains-power-connection device 602 comprises electrically-conductive protrusions (e.g., prongs) 604 that are configured to fit into holes in an electric socket. The mains-power-connection device receives electricity through electrically-conductive protrusions 604, and uses the electricity to deliver power to motion sensor 30. Control unit 14 is disposed within the mains-power-connection device such that, whenever the protrusions are placed inside the holes, the control unit is at least partially within 20 cm of the electric socket. For example, the control unit may be at least partially within 10 cm of the electric socket, i.e., distance D2 in FIG. 27A is less than 10 cm. As shown in FIG. 27B, mains-power-connection device 602 typically comprises a rigid housing 606, from which the electrically-conductive protrusions protrude, and inside of which the control unit is disposed. In general, the disposition of control unit 14 within mains-power-connection device 602 is advantageous, especially in a home setting, in that it is less noticeable to an observer that the patient/subject is being monitored. Typically, control unit 14 communicates wirelessly with a server, and/or with a mobile electronic device. For example, output from the control unit may be communicated to a physician's mobile electronic device.

Figure 28:
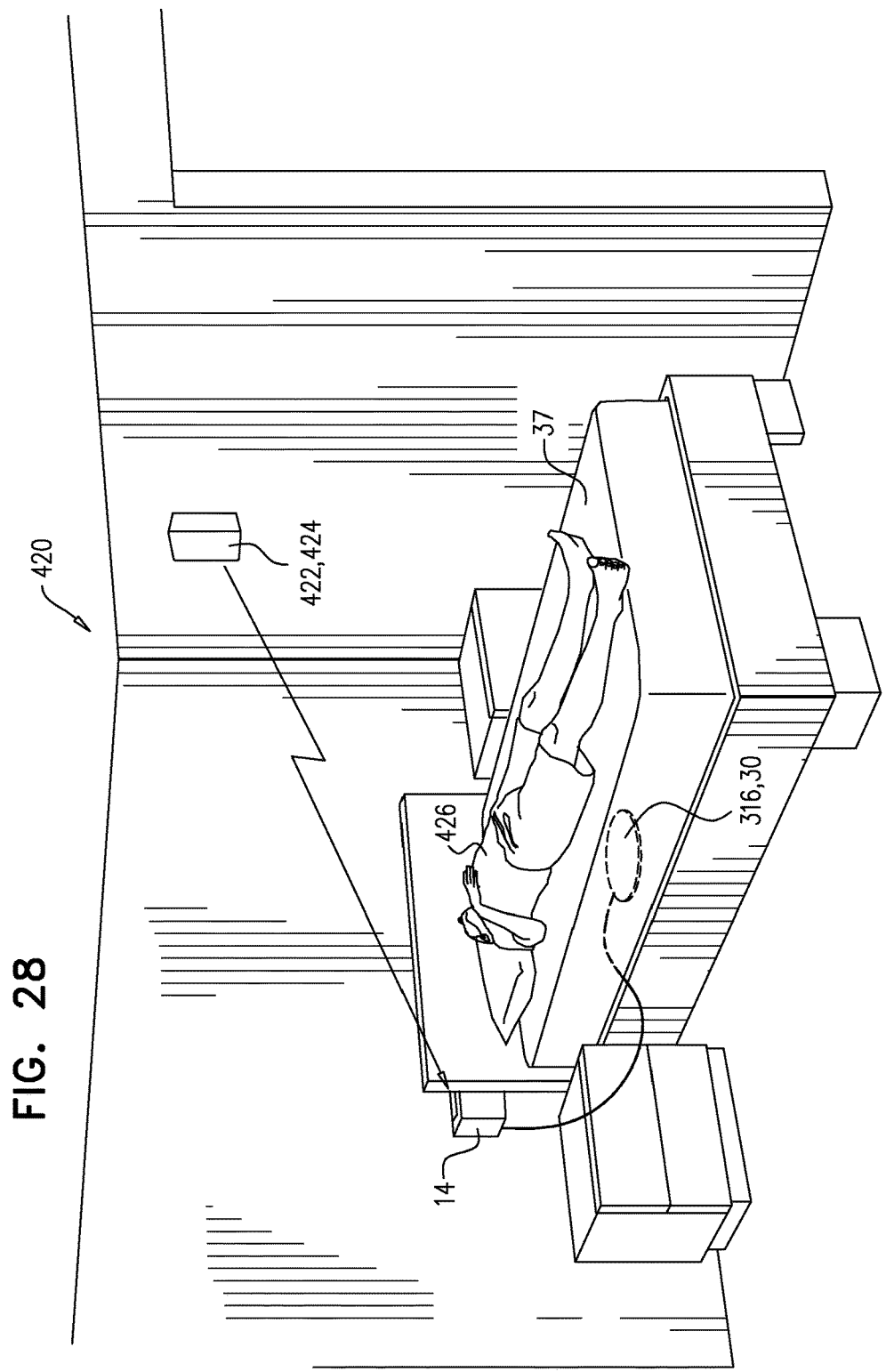
FIGS. 28 and 29 are schematic illustrations of apparatus for use with a burglar alarm, in accordance with some applications of the present invention.
Figure 29:
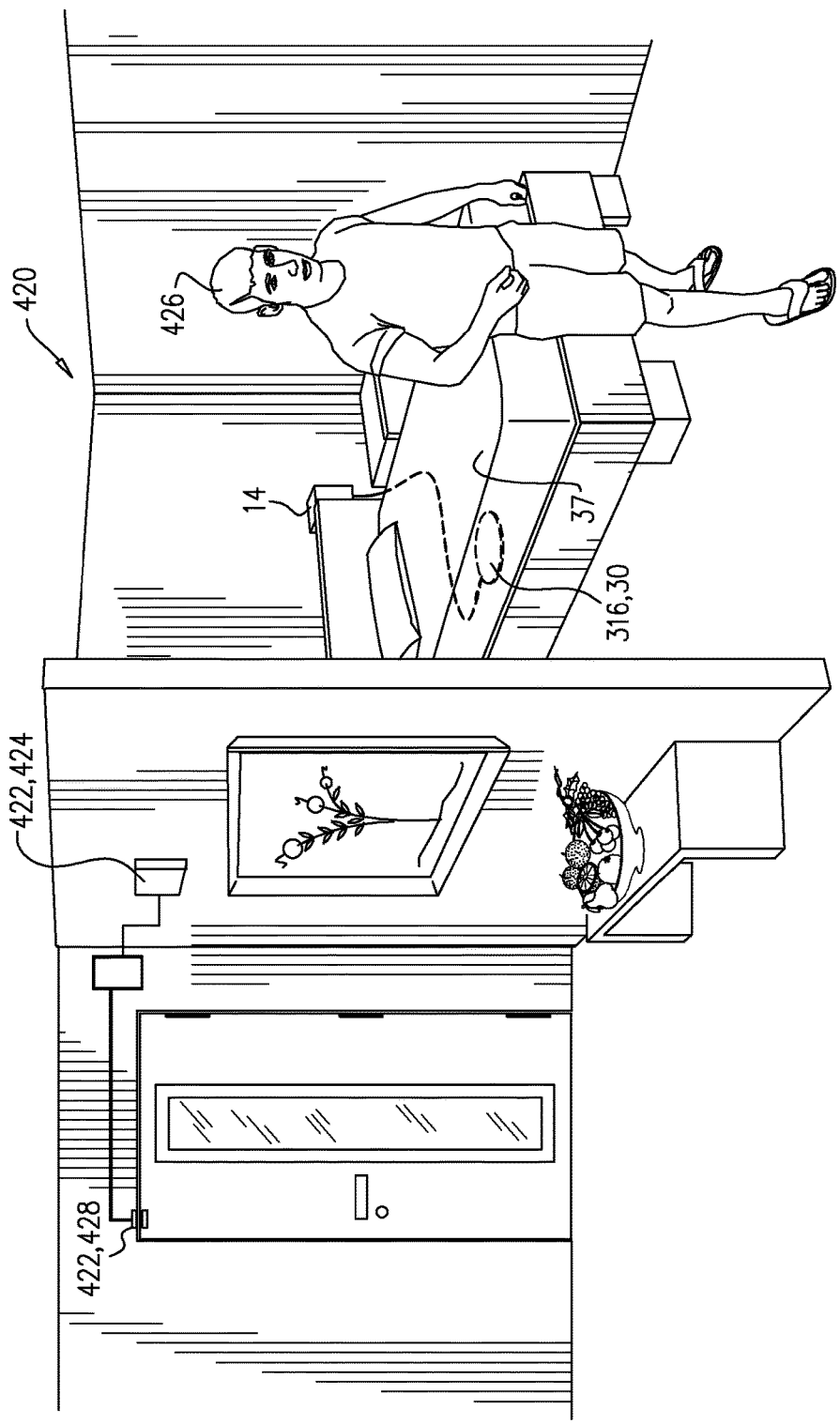

Reference is now made to FIGS. 28 and 29, which are schematic illustrations of apparatus 420 for use with a burglar alarm 422, in accordance with some applications of the present invention. Burglar alarm 422 includes a detector 424 (e.g., a motion detector) configured to detect activity (e.g., motion) and to generate an activity-detection signal in response thereto. Apparatus 420 comprises a sensor 316 (e.g., motion sensor 30), and control unit 14. Control unit 14 identifies a correspondence between (a) the activity-detection signal, and (b) the signal that is generated by sensor 30, and inhibits burglar alarm 422 from being triggered, in response to the correspondence. For example, if a person 426 is moving on resting surface 37, sensor 30 will generate a signal indicative of the movement. If this signal corresponds to the activity-detection signal of detector 424, e.g., detector 424 detects activity on resting surface 37, control unit 14 inhibits the burglar alarm from being triggered. On the other hand, the burglar alarm will not be inhibited if the two signals don't correspond, e.g., it can be inferred that detector 424 is detecting activity outside of resting surface 37. Another example is shown in FIG. 28. In FIG. 28, person 426 is shown as having left resting surface 37. In response to analyzing the signal from sensor 30, the control unit ascertains that the person has left the resting surface, and in response thereto, inhibits the burglar alarm from being triggered, since it is likely that the detector is detecting activity of person 426.

In some applications, the control unit inhibits the burglar alarm from being triggered at a given time only if the person left the resting surface more than a threshold amount of time prior to the given time. For example, as shown in FIG. 29, detector 424 may be disposed outside of the bedroom, e.g., near the entrance to the house, and it typically takes a threshold amount of time for the person to walk from the bedroom to the area in which the detector is disposed. If the threshold amount of time has not passed, it is likely that detector 424 is detecting activity of an entity other than person 426. The threshold amount of time is typically an input to the control unit, and is typically a function of the speed at which person 426 typically moves. In some applications, burglar alarm 422 includes a motion-detection-based alarm, i.e., burglar alarm 422 includes motion detector 424, and the control unit inhibits the motion-detection-based alarm. In some applications, burglar alarm 422 also includes a perimeter alarm 428, and the control unit is configured to not inhibit perimeter alarm 428 from being triggered, while inhibiting the motion-detection-based alarm from being triggered.

Figure 30:
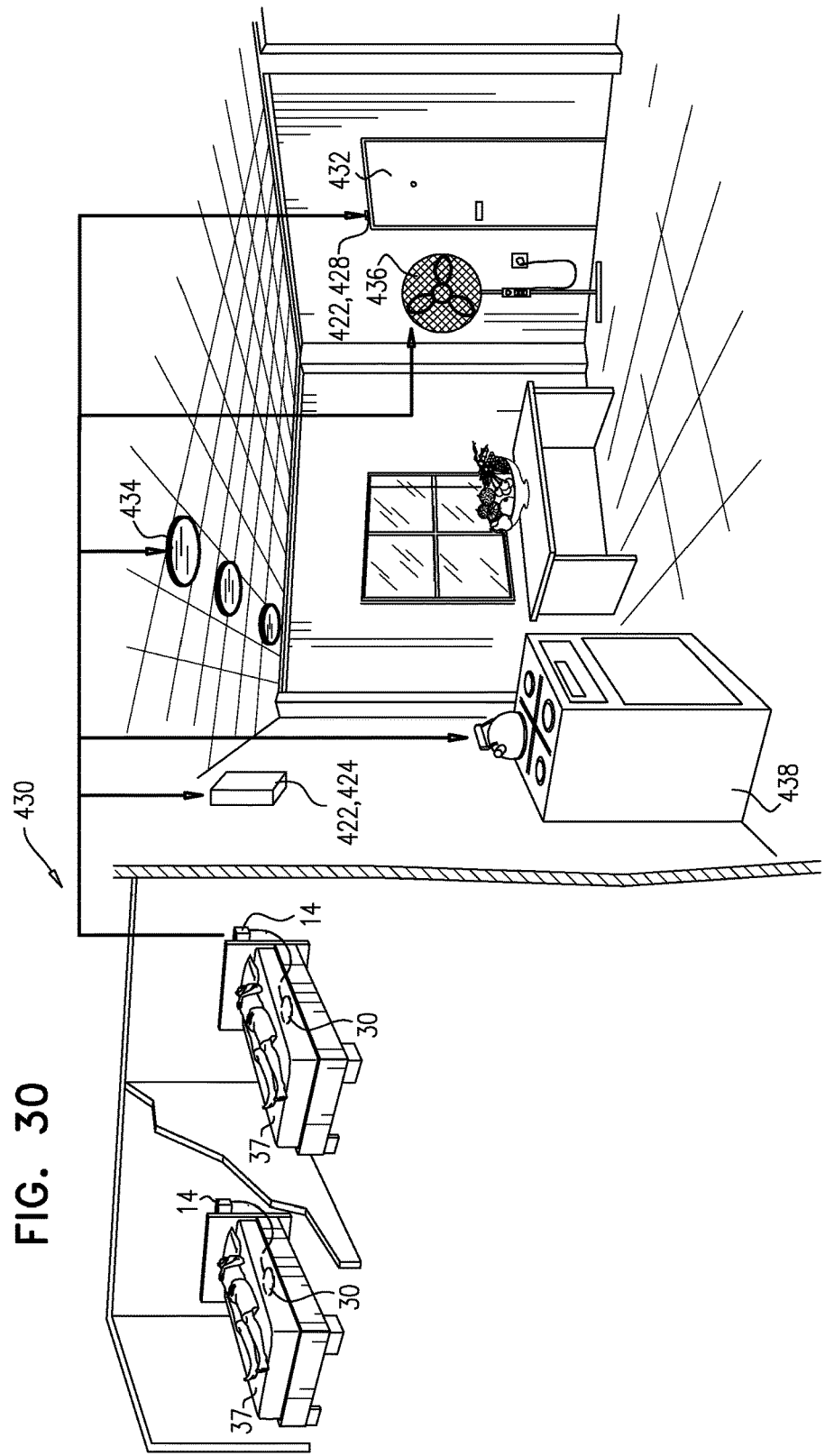
FIG. 30 is a schematic illustration of apparatus for use with a burglar alarm, in accordance with some applications of the present invention.

Reference is now made to FIG. 30, which is a schematic illustration of apparatus 430 for use with burglar alarm 422, in accordance with some applications of the present invention. Apparatus 430 comprises sensor 316 (e.g., motion sensor 30), and control unit 14. Control unit 14 analyzes the signal from sensor 316. In response to the analyzing, the control unit ascertains that person 426 is on the resting surface, and in response thereto, places burglar alarm 422 in an armed state. In general, apparatus 430 may comprise more than one sensor, and/or more than one control unit. For example, FIG. 30 shows an application in which respective sensors and control units are disposed in respective rooms. In response to the control units ascertaining that all of the resting surfaces are occupied, burglar alarm 422 is placed in an armed state.

The arming of burglar alarm 422, as described hereinabove, is but an example of many related actions that control unit 14 can perform (e.g., via wireless communication), upon ascertaining that a person, or all of the persons in the household, is/are likely to be going to sleep. For example, control unit 14 may lock a door 432, reduce an intensity of (e.g., turn off) a light 434, turn off a device 436, and/or turn off an appliance 438. Alternatively or additionally, control unit 14 may generate a notification that (a) door 432 is unlocked, (b) light 434 is on, (c) device 436 is on, and/or (d) appliance 438 is on.

In general, control unit 14 may be embodied as a single control unit 14, or a cooperatively networked or clustered set of control units. Control unit 14 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, control unit 14 is connected to one or more sensors via one or more wired or wireless connections. Control unit 14 is typically configured to receive signals (e.g., motions signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Techniques described herein may be practiced in combination with techniques described in one or more of the following patents and patent applications, which are incorporated herein by reference. In some applications, techniques and apparatus described in one or more of the following applications are combined with techniques and apparatus described herein:

U.S. patent application Ser. No. 11/048,100, filed Jan. 31, 2005, which issued as U.S. Pat. No. 7,077,810;

U.S. patent application Ser. No. 11/197,786, filed Aug. 3, 2005, which issued as U.S. Pat. No. 7,314,451;

U.S. patent application Ser. No. 11/446,281, filed Jun. 2, 2006, which issued as U.S. Pat. No. 8,376,954;

U.S. patent application Ser. No. 11/552,872, filed Oct. 25, 2006, now abandoned, which published as US 2007/0118054;

U.S. patent application Ser. No. 11/755,066, filed May 30, 2007, now abandoned, which published as US 2008/0114260;

U.S. patent application Ser. No. 11/782,750, filed Jul. 25, 2007, which issued as U.S. Pat. No. 8,403,865;

U.S. patent application Ser. No. 12/113,680, filed May 1, 2008, which published as US 2008/0275349;

U.S. patent application Ser. No. 12/842,634, filed Jul. 23, 2010, which issued as U.S. Pat. No. 8,517,953;

U.S. patent application Ser. No. 12/938,421, filed Nov. 3, 2010, which issued as U.S. Pat. No. 8,585,607;

U.S. patent application Ser. No. 12/991,749, filed Nov. 9, 2010, which published as US 2011/0112442;

U.S. patent application Ser. No. 13/107,772, filed May 13, 2011, which issued as U.S. Pat. No. 8,491,492;

U.S. patent application Ser. No. 13/305,618, filed Nov. 28, 2011, which published as US 2012/0132211;

U.S. patent application Ser. No. 13/389,200, filed Jun. 13, 2012, which published as US 2012/0253142;

U.S. patent application Ser. No. 13/750,957, filed Jan. 25, 2013, which issued as U.S. Pat. No. 8,603,010

U.S. patent application Ser. No. 13/750,962, filed Jan. 25, 2013, which issued as U.S. Pat. No. 8,679,034;

U.S. patent application Ser. No. 13/863,293, filed Mar. 15, 2013, now abandoned, which published as US 2013/0245502;

U.S. patent application Ser. No. 13/906,325, filed May 30, 2013, which published as US 2013/0267791;

U.S. patent application Ser. No. 13/921,915, filed Jun. 19, 2013, which issued as U.S. Pat. No. 8,679,030;

U.S. patent application Ser. No. 14/019,371, filed Sep. 5, 2013, which published as US 2014/0005502;

U.S. patent application Ser. No. 14/020,574, filed Sep. 6, 2013, which issued as U.S. Pat. No. 8,731,646;

U.S. patent application Ser. No. 14/054,280, filed Oct. 15, 2013, which issued as U.S. Pat. No. 8,734,360;

U.S. patent application Ser. No. 14/150,115, filed Jan. 8, 2014, which published as US 2014/0171816;

International Patent Application PCT/IL2005/000113, which published as WO 2005/074361;

International Patent Application PCT/IL2006/000727, which published as WO 2006/137067;

International Patent Application PCT/IL2009/000473, which published as WO 2009/138976;

International Patent Application PCT/IL2011/050045, which published as WO 2012/077113;

International Patent Application PCT/IL2013/050283, which published as WO 2013/150523;

International Patent Application PCT/IB2006/002998, which published as WO 2007/052108; and International Patent Application PCT/IL2008/000601, which published as WO 2008/135985.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a subject who is a first person, who shares a bed with a second person, the apparatus comprising:

a thin, flat motion sensor configured to be placed underneath a portion of the bed, and, while disposed underneath the portion of the bed, to:
  detect motion of the subject without contacting the subject, without contacting clothes the subject is wearing, without viewing the subject, and without viewing clothes the subject is wearing,
  detect motion of the second person without contacting the second person, without contacting clothes the second person is wearing, without viewing the second person, and without viewing clothes the second person is wearing, and
  generate a motion signal in response to detecting motion of the subject and motion of the second person; and
a control unit configured to:
  identify components of the motion signal that were generated in response to motion of the subject, by distinguishing between components of the motion signal that were generated in response to motion of the subject, and components of the motion signal that were generated in response to motion of the second person,
  analyze the components of the motion signal that were generated in response to motion of the subject, and generate an output in response thereto,
    wherein the motion sensor comprises a mechanical-filtering element configured to reduce a response of the motion sensor to motion of the second person, relative to motion of the subject.

2. The apparatus according to claim 1, wherein the control unit is configured to identify components of the motion signal that were generated in response to motion of the subject, by identifying components of the motion signal that have a signal strength that is a characteristic signal strength of a motion signal of the subject.

3. The apparatus according to claim 1, wherein the control unit is configured to identify components of the motion signal that were generated in response to motion of the subject by identifying components of the motion signal that have a pattern that is a characteristic pattern of motion of the subject.

4. The apparatus according to claim 1, further comprising a weight sensor that is configured to detect when the subject is lying above the motion sensor, wherein the control unit is configured to identify the components of the motion signal that were generated in response to motion of the subject, in response to a signal that is generated by the weight sensor.

5. The apparatus according to claim 1, wherein the motion sensor is configured to facilitate the identification of components of the motion signal that were generated in response to motion of the subject, by strengthening a signal strength of the components of the motion signal that are generated in response to motion of the subject.

6. The apparatus according to claim 5, wherein the apparatus is for use with a subject who lies on a mattress, and wherein the sensor is configured to be placed at a position selected from the group consisting of: underneath the mattress at a position that is higher than a head of the subject is typically placed, and adjacent to and in contact with a side of the mattress.

7. The apparatus according to claim 6, wherein the sensor is configured such as to facilitate identification, by the control unit, of components of the motion signal that were generated in response to a longitudinal cardio-ballistic effect of the subject.

8. The apparatus according to claim 1, wherein the control unit is configured to identify components of the motion signal that were generated in response to respiratory motion of the subject.

9. The apparatus according to claim 1, wherein the control unit is configured to identify components of the motion signal that were generated in response to cardiac motion of the subject.

10. The apparatus according to claim 1, wherein the control unit is configured to identify components of the motion signal that were generated in response to large body-movement of the subject.

11. The apparatus according to claim 1, wherein the control unit is further configured to:
  analyze the motion signal,
  in response thereto, identify an effect of large body-movement of the second person on sleep of the subject, and
  in response thereto, generate a sleep-disturbance output.

12. The apparatus according to claim 11, wherein the sleep-disturbance output includes an assessment of an effectiveness of a parameter at reducing the effect of the large body-movement of the second person on the sleep of the subject, the control unit being configured to generate the assessment of the effectiveness of the parameter.

13. The apparatus according to claim 12, wherein the parameter is selected from the group consisting of: a parameter of a mattress on which the subject is sleeping, a parameter of the bed, a sleeping arrangement of the subject and the second person, and a room-environment parameter, the control unit being configured to generate the assessment of the effectiveness of the selected parameter.

14. The apparatus according to claim 11, wherein the sleep-disturbance output includes a recommendation to reduce the effect of the large body-movement of the second person on the sleep of the subject by adjusting an adjustable parameter, the control unit being configured to generate the recommendation.

15. The apparatus according to claim 14, wherein the adjustable parameter is selected from the group consisting of: a parameter of a mattress on which the subject is sleeping, a parameter of the bed, a sleeping arrangement of the subject and the second person, and a room-environment parameter, the control unit being configured to generate the recommendation to adjust the selected parameter.

16. The apparatus according to claim 11, wherein the sleep-disturbance output includes instructions to a device to adjust an adjustable parameter, the control unit being configured to generate the instructions.

17. The apparatus according to claim 16, wherein the adjustable parameter is selected from the group consisting of: a parameter of a mattress on which the subject is sleeping, a parameter of the bed, a sleeping arrangement of the subject and the second person, and a room-environment parameter, the control unit being configured to generate the instructions to the device to adjust the selected parameter.

18. The apparatus according to claim 1, wherein the motion sensor consists of a single motion sensor.

19. The apparatus according to claim 1, wherein the control unit is further configured to:
  by analyzing the motion signal, assess an effectiveness of the mechanical-filtering element at reducing the response of the motion sensor to motion of the second person, and
  generate an output in response thereto.

20. The apparatus according to claim 1, wherein the mechanical filtering element comprises an edge region of the motion sensor that is more rigid than a central portion of the motion sensor.

21. The apparatus according to claim 1, wherein the control unit is configured to (a) analyze a portion of the motion signal that was generated in response to motion of the subject, (b) calculate an amplitude threshold based on the analysis, and (c) identify that a given portion of the motion signal was generated in response to motion of the second person, and not in response to motion of the subject, by identifying that the amplitude of the given portion of the motion signal is less than the amplitude threshold.

22. The apparatus according to claim 21, wherein the control unit is configured to calculate the amplitude threshold as a multiple of the amplitude of the components of the motion signal that were generated in response to motion of the subject.

23. The apparatus according to claim 1, wherein the control unit is configured to identify that a portion of the motion signal was generated in response to motion of the second person, and not in response to motion of the subject, by (i) comparing (a) an amplitude of a component of the motion signal generated in response to motion of the subject following the portion to (b) an amplitude of a component of the motion signal generated in response to motion of the subject before the portion, and (ii) determining that the portion of the motion signal was generated in response to motion of the second person, and not in response to motion of the subject, if the amplitude of the component of the motion signal following the portion has changed by less than a threshold amount relative to the amplitude of the component of the motion signal before the portion.

24. The apparatus according to claim 1, wherein the control unit is configured to identify that a portion of the motion signal was generated in response to motion of the second person, and not in response to motion of the subject, by identifying that the portion exhibits ringing.

25. The apparatus according to claim 24, wherein the control unit is configured to identify that the portion of the motion signal generated in response to motion of the second person exhibits ringing by ascertaining that the portion includes a set of at least three consecutive extrema each of which is separated from the preceding extremum of the set by a time that falls within a given time range.

26. The apparatus according to claim 25, wherein the time range is 0.15-0.45 seconds.

27. The apparatus according to claim 24, wherein the control unit is configured to identify that the portion of the motion signal generated in response to motion of the second person exhibits ringing by:

ascertaining that the portion includes a set of at least three consecutive extrema each of which is separated from the preceding extremum of the set by a time that falls within a given time range, and further ascertaining that respective differences between (i) magnitudes of the set of consecutive extrema, and (ii) a magnitude of an extremum that precedes the set of consecutive extrema, fall within a given amplitude range.

28. The apparatus according to claim 27, wherein the given amplitude range is 10%-150% of the magnitude of the extremum that precedes the set of consecutive extrema.

* * * * *